US008242109B2

(12) United States Patent
Glick

(10) Patent No.: US 8,242,109 B2
(45) Date of Patent: Aug. 14, 2012

(54) COMPOSITIONS AND METHODS RELATING TO NOVEL COMPOUNDS AND TARGETS THEREOF

(75) Inventor: Gary D. Glick, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/962,225

(22) Filed: Dec. 7, 2010

(65) Prior Publication Data

US 2011/0195959 A1 Aug. 11, 2011

Related U.S. Application Data

(63) Continuation of application No. 12/044,589, filed on Mar. 7, 2008, now Pat. No. 7,851,465.

(60) Provisional application No. 60/906,016, filed on Mar. 9, 2007.

(51) Int. Cl.
*A61P 17/06* (2006.01)
*A61P 35/02* (2006.01)
*A61P 37/00* (2006.01)

(52) U.S. Cl. .................................................. 514/221
(58) Field of Classification Search ............ 514/221
See application file for complete search history.

(56) References Cited

U.S. PATENT DOCUMENTS

| | | | |
|---|---|---|---|
| 3,261,828 A | 7/1966 | Uskokovic |
| 3,374,264 A | 3/1968 | Uskokovic |
| 3,384,635 A | 5/1968 | Calabateas |
| 3,415,814 A | 12/1968 | Calabeteas |
| 3,847,905 A | 11/1974 | Bub |
| 4,076,823 A | 2/1978 | Wade |
| 4,088,756 A | 5/1978 | Voorhees |
| 4,108,852 A | 8/1978 | Bub |
| 4,110,337 A | 8/1978 | Szarvasi |
| RE30,293 E | 6/1980 | Bub |
| 4,495,101 A | 1/1985 | Klaubert |
| 4,551,480 A | 11/1985 | Stiefel |
| 4,623,646 A | 11/1986 | Casals-Stenzel |
| 4,751,223 A | 6/1988 | Glarnkowski |
| 4,820,834 A | 4/1989 | Evans |
| 4,894,366 A | 1/1990 | Okuhara |
| 4,898,861 A | 2/1990 | Morgan |
| 4,916,138 A | 4/1990 | Ueda |
| 4,929,611 A | 5/1990 | Okuhara |
| 4,946,778 A | 8/1990 | Ladner |
| 5,004,741 A | 4/1991 | Evans |
| 5,041,438 A | 8/1991 | Hsu |
| 5,141,930 A | 8/1992 | Nakao |
| 5,147,872 A | 9/1992 | Golwyn |
| 5,216,148 A | 6/1993 | Klaus |
| 5,288,514 A | 2/1994 | Ellman |
| 5,324,726 A | 6/1994 | Bock |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa |
| 5,591,227 A | 1/1997 | Dinh |
| 5,597,915 A | 1/1997 | Chambers |
| 5,599,352 A | 2/1997 | Dinh |
| 5,633,251 A | 5/1997 | Claremon |
| 5,677,282 A | 10/1997 | Oleksyszyn |
| 5,697,967 A | 12/1997 | Dinh |
| 5,763,437 A | 6/1998 | Sato |
| 5,776,946 A | 7/1998 | McGeer |
| 5,861,380 A | 1/1999 | Gyorkos |
| 5,962,337 A | 10/1999 | Ohimeyer |
| 6,004,942 A | 12/1999 | Firestein |
| 6,074,859 A | 6/2000 | Hirokawa |
| 6,080,568 A | 6/2000 | Day et al. |
| 6,100,254 A | 8/2000 | Budde |
| 6,239,131 B1 | 5/2001 | Shinozaki |
| 6,277,844 B1 | 8/2001 | Spector |
| 6,319,931 B1 | 11/2001 | Kroemer |
| 6,506,744 B1 | 1/2003 | Alig |
| 6,524,623 B1 | 2/2003 | Hodosh |
| 6,524,832 B1 | 2/2003 | Kufe |
| 2,457,405 A1 | 3/2003 | Glick |
| 6,579,854 B1 | 6/2003 | Mitchell |
| 6,605,593 B1 | 8/2003 | Naicker |
| 6,613,739 B1 | 9/2003 | Naicker |
| 6,767,533 B1 | 7/2004 | Casellas |
| 6,824,561 B2 | 11/2004 | Soykan |
| 6,916,813 B2 | 7/2005 | Atwal |
| 7,125,866 B1 | 10/2006 | Glick |
| 7,144,880 B2 | 12/2006 | Glick |

(Continued)

FOREIGN PATENT DOCUMENTS

CA 2372150 11/2000

(Continued)

OTHER PUBLICATIONS

Elz et al., 1989 Eur. J. Med Chem. 259-262.
Atwal et al., Tet Lett. 30, 1989, 7313.
Johnson, K.M., et al., Chemistry & Biology, 2005, 12:486-496.
Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.
Akssira, M., et al., "New Routes to 1,4-benzodiazepin-2,5-diones," Tetrahedron (1994), vol. 50, No. 30, pp. 9051-9060.
Mohiuddin, G., et al., "A Versatile Synthesis of 3H-1(H), 4(H)-Benzodiazepin-2,5-diones," Indian Journal of Chenmistry, 1985, vol. 24B, pp. 905-907.

(Continued)

*Primary Examiner* — Bruck Kifle
(74) *Attorney, Agent, or Firm* — Casimir Jones SC

(57) ABSTRACT

The present invention relates to novel chemical compounds, methods for their discovery, and their therapeutic use. In particular, the present invention provides benzodiazepine compounds, and structurally and functionally related compounds, and methods of using such compounds as therapeutic agents to treat a number of conditions associated with the faulty regulation of the processes of programmed cell death, autoimmunity, inflammation, hyperproliferation, vascular abnormalities, and the like.

15 Claims, No Drawings

U.S. PATENT DOCUMENTS

| | | |
|---|---|---|
| 7,150,433 B2 | 12/2006 | Healy |
| 7,175,953 B2 | 2/2007 | Licha |
| 7,220,739 B2 | 5/2007 | Glick |
| 7,250,410 B2 | 7/2007 | Bourguignon |
| 7,276,348 B2 | 10/2007 | Glick |
| 7,351,421 B2 | 4/2008 | Sung |
| 7,572,788 B2 | 8/2009 | Glick |
| 7,638,624 B2 | 12/2009 | Glick |
| 7,683,046 B2 | 3/2010 | Glick |
| 2002/0025946 A1 | 2/2002 | Buchanan |
| 2002/0048566 A1 | 4/2002 | El-Deiry |
| 2002/0128208 A1 | 9/2002 | Snyder |
| 2003/0044776 A1 | 3/2003 | Dykens |
| 2003/0119029 A1 | 6/2003 | Glick |
| 2004/0009972 A1 | 1/2004 | Ding |
| 2004/0087489 A1 | 5/2004 | Ruiz |
| 2004/0157833 A1 | 8/2004 | Harris |
| 2004/0176358 A1 | 9/2004 | Glick |
| 2005/0113460 A1 | 5/2005 | Glick |
| 2005/0261176 A1 | 11/2005 | Glick |
| 2005/0272723 A1 | 12/2005 | Glick |
| 2006/0025388 A1 | 2/2006 | Glick |
| 2006/0052369 A1 | 3/2006 | Glick |
| 2006/0166975 A1 | 7/2006 | Glick |
| 2007/0036854 A1 | 2/2007 | Glick |
| 2007/0043033 A1 | 2/2007 | Glick |
| 2007/0105844 A1 | 5/2007 | Glick |
| 2007/0111994 A1 | 5/2007 | Glick |
| 2007/0135418 A1 | 6/2007 | Glick |
| 2007/0299059 A1 | 12/2007 | Glick |
| 2008/0064686 A1 | 3/2008 | Durrani |
| 2008/0269194 A1 | 10/2008 | Glick |

FOREIGN PATENT DOCUMENTS

| | | |
|---|---|---|
| CA | 2457405 | 2/2003 |
| DE | 1810423 | 10/1969 |
| EP | 0349949 | 1/1990 |
| EP | 0227539 | 5/1990 |
| EP | 0349949 | 10/1990 |
| EP | 0 906 907 | 7/1999 |
| EP | 1143946 | 10/2001 |
| EP | 1423122 | 2/2003 |
| EP | 1398033 | 3/2004 |
| EP | 1398033 | 6/2004 |
| EP | 1622684 | 2/2006 |
| EP | 1742460 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 11/1990 |
| WO | 91/12779 | 9/1991 |
| WO | 92/01683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | 01/51922 | 7/2001 |
| WO | 02/67988 | 9/2002 |
| WO | 02/098865 | 12/2002 |
| WO | 03/015703 | 2/2003 |
| WO | 03/041658 | 5/2003 |
| WO | 03/045901 | 6/2003 |
| WO | 03/050261 | 6/2003 |
| WO | 03/106628 | 12/2003 |
| WO | 2004/050610 | 6/2004 |
| WO | 2005/004988 | 1/2005 |
| WO | 2006/007532 | 1/2006 |
| WO | 2006/014526 | 2/2006 |
| WO | 2006/029245 | 3/2006 |
| WO | 2006/073448 | 7/2006 |
| WO | 2006/074358 | 7/2006 |
| WO | 2006/053193 | 5/2007 |
| WO | 2007/050587 | 5/2007 |
| WO | 2007/053725 | 5/2007 |
| WO | 2007/146167 | 12/2007 |
| WO | 2008/012553 | 9/2008 |
| WO | 2008/116156 | 9/2008 |
| WO | 2008/133635 | 11/2008 |
| WO | 2009/036175 | 3/2009 |
| WO | 2009/061916 | 5/2009 |

OTHER PUBLICATIONS

Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.

Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.

Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, Mar. 26, 1999, vol. 64, No. 8, pp. 2914-2918.

Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.

Bolli, M.H., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.

Cunha, 2006, "The first bismuth(III)-catalyzed guanylation of thioureas", Tetrahedron Letters 47:6955-56.

Cunha, 2002, "Bismuth nitrate pentahydrate: a new and environmentally benign reagent for guanidylation of N-benzoylthioureas", Tetrahedron Letters 43: 49-52.

Tarpley, et al., J. Chroni Diseases (1965), 18 (abstract only).

Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.

Otto, Michael W., Ph.D., et al., "Benzodiazepine Use, Cognitive Impairment, and Cognitive-Behavioral Therapy for Anxiety Disorders: Issues in the Treatment of a Patient in Need," J. Clin. Psychiatry, 2005, 66 (supp 2).

Yoshi, M., et al., (2005) Nippon Yakurigaku Zasshi 125(1):33-36 (English Abstract attached).

Yasuda, K., (2004) Nippon Rinsho. 62 Suppl. 12:360-363. Abstract not available.

Decaudin, Didier, "Peripheral benzodiazepine receptor and its clinical targeting," Anti-Cancer Drugs, 2004, vol. 15, No. 8.

Bonnot, O., et al., "Exposition in utero au lorazepam et atresie anale: signal epidemiologique," (2003) Encephale. 29 (6):553-559.

Lacapere, Jean-Jacques, Vassilios Papadopoulos, "Peripheral-type benzodiazepine receptor: structure and function of a cholesterol-binding protein in steroid and bile acid biosynthesis," Steroids, 68 (2003) 569-585.

Galiegue, S., et al., "The Peripheral Benzodiazepine Receptor: A Promising Therapeutic Drug Target," (2003) Curr. Med. Chem (10(16):1563-1572.

Papadopoulo, V. (2003), Lecture: Peripheral benzodiazepine receptor: structure and function in health and disease, Ann. Pharm. Fr. 61(1):30-50.

Goethals, Ingeborg, et al., "Is central benzodiazepine receptor imaging useful for the identification of epileptogenic foci in localization-related epilepsies?" European Journal of Nuclear Medicine and Molecular Imaging vol. 30, No. 2, Feb. 2003.

Castedo, Marian, et al., "Mitochondrial Apoptosis and the Peripheral Benzodiazepine Receptor: a Novel Target for Viral and Pharmacological Manipulation," The Journal of Experimental Medicine, vol. 196, No. 9, Nov. 4, 2002.

Buffett-Jerrott S.E. et al., "Cognitive and Sedative Effects of Benzodiazepine Use," Current Pharmaceutical Design, 2002, 8, 45-48.

Smyth, W.F., et al. (1998), "A critical evaluation of the application of capillary electrophoresis to the detection and determination of 1,4-benzodiazepine tranquilizers in formulations and body materials," Electrophoresis 19 (16-17):2870-2882.

Yoshii, M., et al., (1998) Nihon Shinkeo Seishin Yakurigaku Zasshi, 18(2):49-54.

Varani, et al., (1994), "All-trans Retinoic Acid (RA) Stimulates Events in Organ-cultured Human Skin that Underlie Repair," J. Clin. Invest., 94:1747-1753.

Griffith, C.E., "Editorial Comment: Ascomycin: an advance in the management of atopic dermatitis," Br. J. Dermatol., Apr. 2001; 144(4):679-81.

Stern, R.S. (1995), "Epidemiology of Psoriasis," Dermatologic Clinics, 13:717-722.

Fry, L (1988), "Psoriasis," Brit. J. Dermatol., 119:445-461.

Krueger GC, et al., (1984), "Psoriasis," J. Am. Acad. Dermatol., 11:937-947.

Varani, J., et al. (2001), "Heparin-Binding Epidermal-Growth-Factor-Like Growth Factor Activation of Keratinocyte ErbB . . . ", J. Invest. Dermatol., 117:1335-1341.

Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.

International Search Report and Written Opinion, PCT/US2008/082629, mailed Jun. 1, 2009.

Bisaha, S.N., et al., A switch in enantiomer preference between mitochondrial F1F0-ATPase chemotypes, Bioorganic & Medicinal Chemistry Letters, 2005 15(11), pp. 2749-2751.

International Search Report and Written Opinion dated Mar. 27, 2009, PCT/US2008/076021.

EP Supplementary Search Report, EP Application No. 02794914.8 dated Nov. 6, 2008.

EP Patent Application No. 05 80 4417 Supplementary European Search Report dated Mar. 26, 2009.

Algarra, et al., "Application of the Photo-Fries Rearrangement of Aryl N-Chloroacetylanthranylates as Key Step in the . . . ", Heterocycles, vol. 36 1993, pp. 2335-2344.

EP Patent Application No. 06 717616 Supplementary Search Report dated Mar. 26, 2009.

Levitzki, Alexander, "Protein Tyrosine Kinase Inhibitors as Novel Therapeutic Agents," Pharmacol. Ther. vol. 82, Nos. 2-3, pp. 231-239 (1999).

Sanchez, et al., "Tumorigenic activity of the BCR-ABL oncogenes is mediated by BCL2" Proc Natl Acad Sci U S A (Jun. 6, 1995) 92(12) 5287-5291.

Ji Yang, et al., "Prevention of Apoptosis by BCL-2; Release of Cytochrome c from Mitochondria Blocked" Science 275, 1129 (1997).

Prindull, "Apoptosis in the embryo and tumorigenesis" European Journal of Cancer, vol. 31, Issue 1 (1995) pp. 116-123.

Chinese Office Action, CN Patent Application No. 200580029827.4, dated Apr. 17, 2009.

Lowe, "Systemic treatment of severe psoriasis," The New England Journal of Medicine, 324 (5), Feb. 7, 1991, pp. 333-334.

Laupacis, et al., "Cyclosporin A: a powerful immunosuppressant", CMA Journal, May 1, 1982, vol. 126, pp. 1041-1046.

Lee, et al., J. Org. Chem. 1999, 64, 3060-3065.

Solomko, et al., Chemistry of Heterocyclic Compounds, vol. 11, No. 11, Nov. 1975, pp. 1231-1248.

Adachi, M., et al., "Aberrant Transcription Caused by the Insertion an Early Transposable Element . . . ," PNAS. USA-90:1756-1760 (1993).

Adelman, N.E., et al., Treatment of (NZB X NZW)F1 Disease with Anti-I-A Monoclonal Antibodies; J. Exp. Med.-158:1350.1355 (1983).

Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).

Atwal, K.S., et al., "Small Molecule Mitochondrial F1F0 ATPase Huydrolase Inhibitors as Cardioprotective Agents" J. Med. Chem. 47, pp. 1081-1084 (2004).

Baader, S.L., et al., Uptake and Cytotoxicity of Ascorbic Acid and Dehydroascorbic Acid . . . Anticancer Research-14:221-228 (1994).

Beale, P.J., et al., "BCL-2 Family Protein Expression and Platinum Drug Resistance in Ovarian Carcinoma," British Journal of Cancer—82 (2) :436-440 (2000).

Beurdeley-Thomas, et al., "The peripheral benzodiazepine receptors: a review," Journal of Neuro-Oncology 46 (2000) 45-56.

Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.

Blum, P., et al., "Stiff-Person Syndrome: An Autoimmune Disease," Movement Disorders 6(1):12-20 (1991).

Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

Bono et al., "Peripheral benzodiazepine receptor agonists exhibit potent antiapoptotic activities," Biochemical and Biophysical Research Communications, 1999, 265, pp. 457-461.

Boojamra, C.G., et al., "Solid-Phase Synthesis of 1,4. Benzodiazepine-2,5-Diones. Library Prep. and Demonstration of Synthesis Generality," J. Org. Chem.-62:1240-1256 (1997).

Bunin et al., "Synthesis and evaluation of 1,4-benzodiazepine libraries", Methods in Enzymology, 1996, 267, pp. 448-465.

Bunin, B.A., et al., "The Combinatorial Synthesis and Chemical and Biological Evaluation of a 1,4-Benzodiazepine Libra ," PNAS USA-91:4708-4712 (1994).

Bunin, BA., et al., "A General and Expedient Method for the Solid-Phase Synthesis of 1,4-Benzodlazepine Derivatives," J. Am. Chem. Soc.—114:10997-10998 (1992).

Chumakov,A.M., et al., "Analysis of p53 Transactivation Through High-Affinity Binding Sites," Oncogene-8:3005o3011 (1993).

Churcher et al., "A new series of potent benzodiazepine y-Secretase inhibitors," Bioorganic & Medicinal Chemistry Letters 13 (2003) 179-.

Cohen, P.L., et al., "Lpr and gld: Single Gen• Models of Systemic Autoimmunity and Lymphoproliferative Disease,"Annu. Rev. Immunol. 9:243-269 (1991).

Cole et al., "The EBV-Hybridoma Technique and its Application to Human Lung Cancer", Monoclonal Antibodies and Cancer Therapy, Alan R. Liss, Inc., pp. 77-96 [1985].

Colosi, et al,"Mutational analysis of the intracellular domain of the human growth hormone recetor", J. Biol. Chem., 268:12617 [1993].

Crabtree, R.H., "A New Type of Hydrogen Bond," Science 282:2000-2001 1998.

Darrow et al., "Structurally similar small molecule photoaffinity CCK-A Agonists and Antagonists as Novel Tools . . . ", Bioorganic & Medicinal Chemistry Letters 8 (1998) 3127-3132.

Desoize, B., "Anticancer Drug Resistance and Inhibition of Apoptosis," Anicancer Research—14:2291-2294 1994.

Dichek, David A., et al., "Seeding of intravascular stents with genetically engineered endothelial cells," Laboratory Investigation, 80:5 pp. 1347-1353 (1989).

Doble, A., et al., "Labelling of Peripheral-Type Benzodiazepine B Human Brain with [aH]I 1195: Anatomical and Subcellular Distribution," Brain Research Bulletin,18:49-61 1987.

Don, A. et al., Cancer Cell, vol. 3, May(2003) 497-509.

Donadio, J.V., et al., Immunosuppressive Drug Therapy in Lupus Nephritis, American Journal of Kidney Diseases 21 (3):239-250 1993.

Ermak, T.H., et al., "Treatment of Murine Lupus with Monoclonal Antibody to L3T4," Laboratory Investigation 61(4):447-456 1989.

Fuh et al, "Rational design of potent antagonists to the human growth hormone receptor", Science, 256:1677 [1992].

Gallant, J.E., et al.,"Incidence and Natural History of Cytomegalovirus Disease in Patients with Advanced Human . . . " The Journal of Infect. Disease, 166: 1223-122 (1992).

Garcia-Calvo, M., et al. "Inhibition of Human Caspases by Peptide-Based and Macromolecular Inhibitors," The Journal of Biological Chemistry 273(49):32608-32613 1998.

Gorczyca, W., et al., "Induction of DNA Strand Breaks Associated with Apoptosis During Treatment of Leukemias," Leukemia 7(5):659-670 1993.

Gordon, C., et al.. "Chronic Therapy with Recombinant Tumor Necrosis Factor-or in Autoimmune NZB/NZW Fi Mice,"Clinical Immunology and Immunopatholoy—52:421-434 (1989).

Gordon, E.M., et al., Applications of Combinatorial Technologies to Drug Discovery. 2. Combinatorial Organic 52 Synthesis, Library Screening . . . Journal of Med. Chem. 37(10): (1994).

Grasberger, Bruce L., "Discovery and cocrystal structure of benzodiazepinedione HDM2 antagonists that activate p53 in cells", J. Med. Chem., 48, (2005), 909-912.

Gupta et al., "Psychitripic drugs in dermatology . . . " Database:EMbase (AN:86111413), Journal of the American Academy of Dermatology, 1986, vol. 14, No. 4, pp. 633-645.

Hahn, B.H., et al.; "Influence of Cyclophosphamide and Other Immunosuppressive Drugs on Immune Disorders . . . ," Arthritis and Rheumatism—18(2):145-152 (1975).

Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).

Hang, L., et al., "A Spontaneous Rheumatoid Arthritis-Like Disease in MR/1 Mice," J. Exp. Mod.—155:1690-1701 1982.

Herranz, R., "Cholesystokinin Antagonists: Pharmacological and Therapeutic Potential", Medicinal Research Reviews 23 (2003) 559-603.

Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).

Horowitz, R.E., et al., "Cyclophosphamide Treatment of Mouse Systemic Lupus Erythematosus," Laboratory Investigation 21 (3): 199-206 1969.

Hulme, C. J. "Improved procedure for the solution phase preparation of 1,4-benzodiazepine-2,5-dione libraries . . . ", Org. Chem., 63,(1998), 8021-8023.

Huse et al., "Generation of a Large Combinatorial Library of the Immunoglobulin Repertoire in Phage Lambda", Science, 246:1275-1281 [1989].

International Search Report and Written Opinion of PCT/US2008/057827 dated Oct. 6, 2008.

IPER and ISR for PCT/us02/31942 mailed Feb. 2, 2007.

Itoh, N., et al., "The Polypeptide Encoded by the cDNA for Human Cell Surface Antigen Fas Can Mediate Apoptosis," Cell 66:233-243 (1991).

Jones, The non-conalent interaction of pyrrolo[2, 1-c][benzodiazepines-5, 11-diones with DNA, Anti-Cancer Drug Design, 5:249-264 (1990).

Kamal, A., "Synthesis of DNA-interactive Pyrrolo[2,1-c][1,4] benzodiazepines by employing polymer-supported reagents . . . ," Synlett, 14,(2004), 2533-35.

Karle Jesper et al., "Diazepam protects against rat hippocampal neuronal cell death induced by antisense oligodeoxnynucleotide to GABA-A receptor gamma-2 subunit" Brain Research, vol. 765, No. 1, 1997, pp. 21-29.

Kerver et al, "In situ detection of spontaneous superoxide anion and singlet oxygen production by mitochondria in . . . ", Histochem. J., 29:229-237 [1997] (Abstract only).

Kim et al., "Synthesis of 3-substituted 1,4-benzodiazepin-2-ones," J. Braz. Chem. Soc. 9:375-379 (1998).

Kohler and Milstein, "Continuous cultures of fused cells . . . ", Nature, 256:495-497 [1975].

Koopman, W.J., et al., "The MRL-Ipr/Ipr Mouse. A Model for the Study of Rheumatoid Arthritis," Scan& J. Rheumatolo Suppl 75:284-o289 (1988).

Korsmeyer, S.J., "Bcl-2 Initiates a New Category of Oncogenes: Regulators of Cell Death," Blood 80(4):879-886 1992.

Kozbor, et al.• "The production of monoclonal antibodies from human lymphocytes", Immunol. Today, 4:72 [1983].

Lee, Sunwoo et al., "Improved Catalysts for the Palladium-Catalyzed Synthesis of Oxindoles by . . . ", J. Org. Chem. 2001, 66, pp. 3402-3415.

Lewis et al., "Editors' view: Cancer pharmacotherapy: 21st century 'magic bullets' and changing paradigms", British Journal of Clinical Pharmacology, 2006, 62:1,pp. 1-4.

Liu, J.R., et al., "Bclox•. is Expressed in Ovarian Carcinoma and Modulates Chemotherapy-induced Apoptosis," Gynecologic Oncology 70:398-403 (1998).

Los, M., et al., The Role of Caspases in Development, Immunity, and Apoptotic Signal Transduction: Immunity-10:629-639 (1999).

Lowman, et al., "Mutational analysis and protein engineering of receptor-binding determinants in human placental lactogen", J. Biol. Chem. 266:10982 [1991].

Luria,et al., "Tumor Viruses", General Viology 3rd edition,. 436-446 (1978)- Eds. John Wile & Sons, New York.

Malgrange, B., et al., "I•-Carbolines Induce Apoptotic Death of Cerebellar Granule Neurones in Cultures," NeuroReport 7(18):3041-3045 (1996).

Marino, M., et al., "Prevention of Systemic Lupus Erythematosus in MRL/Ipr Mice by Administration of an Immunoglobulin . . . ," Nature Biotechnology—18:735-739 (2000).

MCDonnell'—349:254-256T'J et al., Progression from Lymphoid Hyperplasia to High-Grade . . . Nature-349:254-256 (1991).

Miccoli, et al., "Potentiation of Lonidamine and Diazepam . . . ", Journal of the National Cancer Institute, vol. 90, No. 18, pp. 1400-1406, Sep. 1998.

Miernik et al., "The antimitotic activities of some benzodiazepines", Experientia, 1986, 42, pp. 956-958.

Miller, K.A., et al., "Benzodiazepines Prevent Neuronal Death by Apoptosis & Necrosis . . . ,"Society for Neuroscience Abstracts—24(1-2):979 (1998).

Monks, A., et., "Feasibility of High-Flux Anticancer Drug Screen Using a Diverse Panel of Cultured Human Tumor Cell Lines, Journal of the National Cancer Institute, 83:757-766 (1991).

Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).

Okuyama, H., et al., "Analysis of Defective Delayed-Type Hypersensitivity in Autoimmune Mice Bearing Ipr Gene," Clln. Ex p. ImmunoL 63:87-94 1986.

Okuyama, H., et al., "Effect of Cyclophosphamide Pretreatment on Defective Delayed-Type Hypersensitivity . . . ," Int Arch. Allergy Appl. Immunol. 88:394-40 (1989).

Ozols, R.F., "Paclitaxel Plus Carboplatin in the Treatment of Ovarian Cancer," Seminars in Oncology 26(1) (Supp.2:84-89 (1999).

Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042. (2000).

Parks, Daniel J. "1,4-benzodiazepine-2,5-diones as small molecule antagonists of the HDM2-p53 interaction . . . " Bioorg Med Chem. Ltrs,. 15,(2005), 765-770.

Paull, K.D., et al., "Display and analysis of patterns of differential activity of drugs against human tumor . . . ", J. Natl. Cancer Inst., 81:1088-1092 [1989] (Abstract only).

Pestell, K.E., et al., "Charactehsation of the P53 Status, BCL-2 Expression and Radiation and Platinum Drug Sensitivity of . . . ," Int J. Cancer -77:913-918 (1998).

Raboisson, P. "Structure-based design, synthesis and biological evaluative of novel 1,4-diazepines as HDM2 antagonists," Bioorg Med Chem. Ltrs., 15,(2005), 1857-1861.

Ramdas et al., "Benzodiazepine compounds as inhibitors of the Src protein tyrosine kinase . . . " Archives of Biochemistry and Biophysics 368 (1999) 394-400.

Raynaud, F.I., et al., "Intracellular Metabolism of the Orally Active Platinum Drug JM216: Influence of Glutathione Levels," Br. J. Cancer 74(3) :380-?386 (1996).

Russell, J.H., et al., "Mature T Cells of Autoimmune Ipr/Ipr Mice have a Defect in Antigen-Stimulated Suicide,"Proc. Nat. Acad. Sci. USA 90:4409-4413 (1993).

Sakata, K., et al., "Role of Fas/FasL Interaction in Physiology and Pathology: The Good and the Bad," Clinical Immunology and Immunopathology 87(1):1-7 (1998).

Sandstrom, P.A., et al., Autocrine Production of Extracellular Catalase Prevents Apoptosis.. Proc. Natl. Acad. Sci. USA-90:4708-4712 (1993).

Schlumpf, M., et al., "Delayed Developmental Immunotoxicity of Prenatal Benzodiazepines," Toxic. In Vitro—8 (5):1061-1065(1994).
Schoemaker, H., et al., "Specific High-Affinity Binding Sites for [3H]Ro5—4864 in Rat Brain and Kidney," The J. of Pharm and Experimental Therapeutics -225(1)61-69 (1983).
Schwab, M., et al., "Amplified DNA with Limited Homology to myc Cellular Oncogene is Shared by Human Neuroblastoma Cell Lines and . . . ," Nature -305:245-248 (1983).
Scott, C.F., et al., "Comparison of Antigen-Specific T Cell Responses in Autoimmune MRL/mp-Ipr/Ipr and MRUMp-++ Mice," The Journal of Immunology- 1322:633-639 (1994_.
Sentman, C.L., et al., "bcl-2 Inhibits Multiple Forms of Apoptosis but not Negative Selection in Thymocytes," Cell 67:879-886 (1991).
Shaughnessy, Kevin, H., et al., "Palladium-Catalyzed Inter- and Intramolecular . . . " J. Org. Chem. 1998, 63, pp. 6546-6553.
Sheppard, R.C., et al., "Acid-Labile Resin Linkage Agents for Use in Solid Phase Peptide Synthesis;" Int J. Peptide Protein Res. 20:451-454 (1982).
Snyder, Jane R., et al, "Dissection of melanogenesis with small molecules identifies prohibition as a regulator", Chemistry & Biol. 12:477-484, 4(2005).
Stevens, S.Y., et al., "Non Nucleic Acid Inhibitors of Protein-DNA Interactions Identified Through Combinatorial Chemistry," J. Am. Chem.Soc. -118:10650-10651 (1996).
Sugimoto, T., et al., Determination of Cell Surface Membrane Antigens . . . JNCI-73: (1):51-57 (1984).
Swanson et al, "Ligand recognition by anti-DNA Autoantibodies," Biochemistry, 35:1624-1633 [1996] (Abstract only).
Swanson, P.C., et al., "Ligand Recognition by Murine Anti-DNA Autoantibodies," J. Clin. Invest 97(7):1748-1760 (1996).
Swanson, P.C.,et al., "High Resolution Ephope Mapping of an Anti-DNA Autoantibody Using Model DNA Ligands," J. Immunology 71 152(5):2601-2612 (1994).
Takahashi, T., et al., "Generalized Lymphoproliferative Disease in Mice, Caused by a Point Mutation in the Fas Ligand;" Cell 76:969-976 (1994).
Tanimoto, Y., et al., Benzodiazepine Receptor Agonists Modulate Thymocyte Apoptosis Through Reduction of the Mitochondrial . . . Jpn. J. Pharmacol. 79:177-183 (1999).
Taupin, V., et al., Endogenous Anxiogenic peptide, ODN-Diazepam-Binding Inhibitor, and Benzodiazepines.. Lymphokine and Cytoklne Research 10(1):7-13 (1991).
Theoffopoulous, AN, et al., "Murine Models of Systemic Lupus Erythematosus," Advances in Immunology 37:269-390 (1985).
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosia,"Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y., et al., "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
International Search Report, International Patent Application No. PCT/US05/24060, dated Dec. 13, 2006.
International Search Report, International Patent Application No. PCT/US02/26171 dated Aug. 8, 2003.
International Search Report, International Patent Application No. PCT/US01/11599 dated Mar. 6, 2001.
International Search Report, International Patent Application No. PCT/US005/031942 dated Sep. 21, 2006.
International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/U52006/042753, dated May 6, 2008.
Wrtten Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiner's Report, AU Patent App. No. 2005323519 dated Nov. 27, 2007.
EP Search, EP Patent App. No. 03 027 484.9-2117, dated Jan. 31, 2005.
Canadian Patent Search, CA Patent Application No. 2,457,405, dated Feb. 6, 2007.
Wolvetang, et al., FEBS Letters (1994), 339, 40-44.
Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
Godic, "New approaches to psoriasis treatment. A review." 2004, Acta Dermatoven APA, vol. 13, No. 2, pp. 50-57.
International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
AU Patent Application No. 2006203946 Examiner's Report dated Sep. 10, 2008.
EP Search, EP Patent Application No. 05856659.7 mailed Dec. 9, 2008.
Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivey-conferring Protein (OSCP) of Mitochondrial ATP Synthase," The Journal of Biological Chemistry, vol. 267, No. 18,m Issue of Jun. 25, pp. 12860-12867, 1992.
Piedimonte, et al., "Association of Tyrosine Protein Kinase Activity With Mitochondria in Human Fibroblasts," Journal of Cellular Biochemistry 32:113-123 (1986).
EP Search, EP Patent Application No. 04 775 923.8, dated Dec. 15, 2008.
Appleby, et al., "Murine chronic graft-versus-host disease as a model of osystemic lupus erythematosus: effect of immunosuppressive drugs on disease development," Clin. Exp. Immunol. (1989) 78, 449-453.

Bastian, et al., "Casein Interference in Bovine Plasmin Assays Using a Synthetic Substrate," (1991) J Dairy Sci 74:4119-4124.

Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.

Bhagavathula, Narasimharao, et al., "7-Chloro-t-(4-hydroxyphenyl_-1-methyl-3-(naphthalen-2-ylmethyl) . . . ", J. Pharmacol & Exp Ther 324: 938-947 (2008).

Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.

Mahrle, et al., Br. J. Bermatol. 1974, 91, 529-540.

Mui et al. Br. J. Dermatol. 1975, 92, 255-262.

EP Search Report dated Nov. 26, 2009, EP Patent Application No. 09003224.4.

Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.

Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.

Bossu, et al., "IL-18 cDNA vaccination protects mice from spontaneous lupus-like autoimmune disease," PNAS 2003, 100: 14181-14186.

De Bandt, et al., "Systemic lupus erythematosus induced by anti-tumour necrosis factor alpha therapy: a French national survey," Arthritis Res. & Ther., 2005, 7: R545-R551.

Abunasser, et al., "Etanercept-Induced Lupus Erythematosus Presenting as a Unilateral Pleural Effusion," Chest 2008, 134: 850-853.

Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.

Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).

Kluge, et al., "Kinetics of Inactivation of the F1F0 ATPase of *Propionigenium modestum* by Dicyclohexylcarbodiimide in Relationship to H+ and Na+ Concentration: Probing the Binding Site for the Coupling Ions," Biochemistry 1993, 32, 10378-10386.

Covelli, Vito, "Stress, Neuropsychiatric Disorders and Immunological Effects Exerted by Benzodiazepines," Immunopharmacology and Immunotoxicology, 20(2), 199-209 (1998).

EP Search Report dated Jun. 23, 2010, EP Patent Application No. 10 003 823.1.

EP Search Report dated Aug. 10, 2010, EP Patent Application No. 08731682.4.

Office Action Mailed Apr. 3, 2009, U.S. Appl. No. 11/176,719, filed Jul. 6, 2005.

Office Action Mailed Aug. 19, 2009, U.S. Appl. No. 11/176,719, filed Jul. 6, 2005.

Office Action Mailed May 24, 2010, U.S. Appl. No. 11/176,719, filed Jul. 6, 2005.

EP Supplementary Search Report mailed Nov. 6, 2008, EP Patent Application No. 02794914.8.

Yano, Masafumi, et al., "Effect of Milrinone on Left Ventricular Relaxation and Ca2+ Uptake Function of Cardiac Sarcoplasmic Reticulum," Am. J. Physiol. Heart Circ. Physiol, 279: H1898-H1905 (2000).

Gatza, et al., "Manipulating the Bioenergetics of Alloreactive T Cells Causes Their Selective Apoptosis and Arrests Graft-Versus-Host Disease," Sci. Transl. Med. 3(67ra8): 1-8 (2011).

Shoemaker, et al., "The NC160 Human Tumour Cell Line Anticancer Drug Screen," Nat. Rev. Cancer 6:813-823 (2006).

COMPOSITIONS AND METHODS RELATING TO NOVEL COMPOUNDS AND TARGETS THEREOF

CROSS-REFERENCE TO RELATED APPLICATIONS

The present application is a continuation of U.S. patent application Ser. No. 12/044,589, filed Mar. 7, 2008 which will issue on Dec. 14, 2010 as U.S. Pat. No. 7,851,465, which claims priority to expired U.S. Provisional Patent Application No. 60/906,016, filed on Mar. 9, 2007, the contents of which are hereby incorporated by reference in their entireties.

FIELD OF THE INVENTION

The present invention relates to novel chemical compounds, methods for their discovery, and their therapeutic use. In particular, the present invention provides benzodiazepine compounds, and structurally and functionally related compounds, and methods of using such compounds as therapeutic agents to treat a number of conditions associated with the faulty regulation of the processes of programmed cell death, autoimmunity, inflammation, hyperproliferation, vascular abnormalities, and the like.

BACKGROUND OF THE INVENTION

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also the primary defense against cells and invaders (e.g., viruses) which threaten the well being of the organism.

Not surprisingly many diseases are associated with dysregulation of the process of cell death. Experimental models have established a cause-effect relationship between aberrant apoptotic regulation and the pathenogenicity of various neoplastic, autoimmune and viral diseases. For instance, in the cell mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of autoimmune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, the destruction of the immune system in individuals infected with the human immunodeficiency virus (HIV) is thought to progress through infected $CD4^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL-mediated clearance of aberrant cells. Faulty regulation of the apoptotic machinery has also been implicated in various degenerative conditions and vascular diseases.

It is apparent that the controlled regulation of the apoptotic process and its cellular machinery is vital to the survival of multicellular organisms. Typically, the biochemical changes that occur in a cell instructed to undergo apoptosis occur in an orderly procession. However, as shown above, flawed regulation of apoptosis can cause serious deleterious effects in the organism.

There have been various attempts to control and restore regulation of the apoptotic machinery in aberrant cells (e.g., cancer cells). For example, much work has been done to develop cytotoxic agents to destroy aberrant cells before they proliferate. As such, cytotoxic agents have widespread utility in both human and animal health and represent the first line of treatment for nearly all forms of cancer and hyperproliferative autoimmune disorders like lupus erythematosus and rheumatoid arthritis.

Many cytotoxic agents in clinical use exert their effect by damaging DNA (e.g., cis-diaminodichroplatanim(II) cross-links DNA, whereas bleomycin induces strand cleavage). The result of this nuclear damage, if recognized by cellular factors like the p53 system, is to initiate an apoptotic cascade leading to the death of the damaged cell.

However, existing cytotoxic chemotherapeutic agents have serious drawbacks. For example, many known cytotoxic agents show little discrimination between healthy and diseased cells. This lack of specificity often results in severe side effects that can limit efficacy and/or result in early mortality. Moreover, prolonged administration of many existing cytotoxic agents results in the expression of resistance genes (e.g., bcl-2 family or multi-drug resistance (MDR) proteins) that render further dosing either less effective or useless. Some cytotoxic agents induce mutations into p53 and related proteins. Based on these considerations, ideal cytotoxic drugs should only kill diseased cells and not be susceptible to chemo-resistance.

One strategy to selectively kill diseased cells or block their growth is to develop drugs that selectively recognize molecules expressed in diseased cells. Thus, effective cytotoxic chemotherapeutic agents, would recognize disease indicative molecules and induce (e.g., either directly or indirectly) the death of the diseased cell. Although markers on some types of cancer cells have been identified and targeted with therapeutic antibodies and small molecules, unique traits for diagnostic and therapeutic exploitation are not known for most cancers. Moreover, for diseases like lupus, specific molecular targets for drug development have not been identified.

What are needed are improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers).

SUMMARY

The present invention provides novel compounds that find use in treating a number of diseases and conditions in humans and animals and that find use in research, compound screening, and diagnostic applications. In addition, the present invention also provides uses of these novel compounds, as well as the use of known compounds, that elicit particular biological responses (e.g., compounds that bind to particular target molecules and/or cause particular cellular events). Such compounds and uses are described throughout the present application and represent a diverse collection of compositions and applications.

Certain preferred compositions and uses are described below. The present invention is not limited to these particular compositions and uses. The present invention provides a number of useful compositions as described throughout the present application.

In certain embodiments, the present invention provides compounds described by the following formulas:

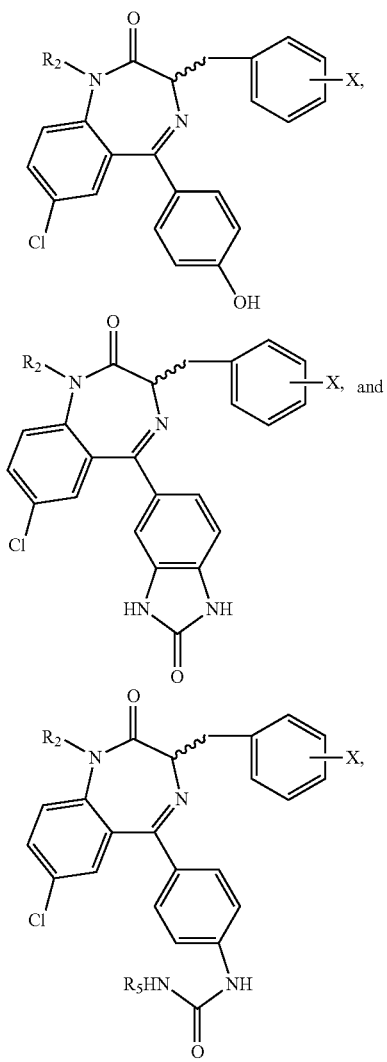

including salts, esters, and prodrugs thereof; and
including both R and S enantiomeric forms and racemic mixtures thereof;

wherein
X is halogen (e.g., Br, Cl, F), alkyl (e.g., methyl, ethyl, propyl (e.g., isopropyl), butyl (e.g., isobutyl, sec-butyl, tert-butyl), pentyl, isoamyl, neopentyl, 1-ethylpropyl, 3-methylpentyl, 2,2-dimethylbutyl, heptyl, hexyl, octyl, 3-ethylbutyl, cyclopropyl, cyclobutyl, cyclopentyl, cyclohexyl), or substituted alkyl;

$R_2$ is hydrogen or a linear or branched alkyl (e.g., methyl, ethyl, propyl (e.g., isopropyl), butyl (e.g., isobutyl, sec-butyl, tert-butyl), pentyl, isoamyl, neopentyl, 1-ethylpropyl, 3-methylpentyl, 2,2-dimethylbutyl, heptyl, hexyl, octyl, 3-ethylbutyl, cyclopropyl, cyclobutyl, cyclopentyl, cyclohexyl); and $R_5$ is alkyl (e.g., methyl, ethyl, propyl (e.g., isopropyl), butyl (e.g., isobutyl, sec-butyl, tert-butyl), pentyl, isoamyl, neopentyl, 1-ethylpropyl, 3-methylpentyl, 2,2-dimethylbutyl, heptyl, hexyl, octyl, 3-ethylbutyl, cyclopropyl, cyclobutyl, cyclopentyl, cyclohexyl) or substituted alkyl.

In certain embodiments, the present invention provides the following compounds:

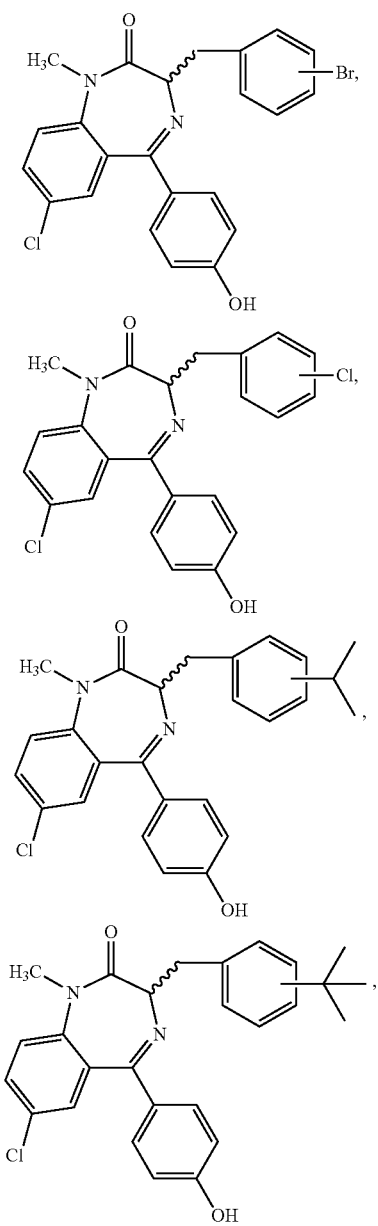

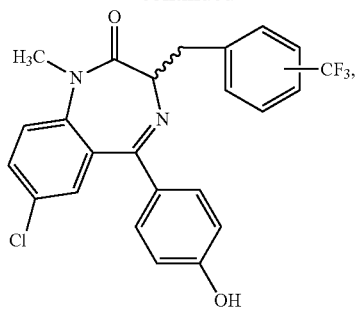
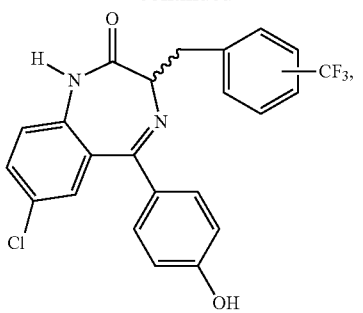
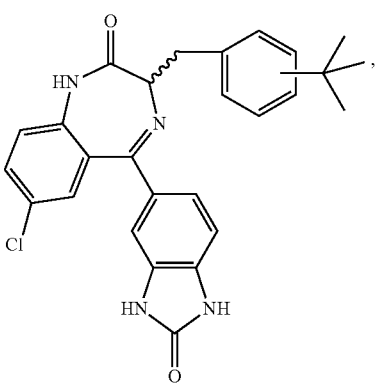
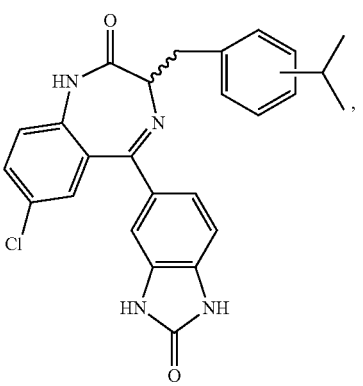
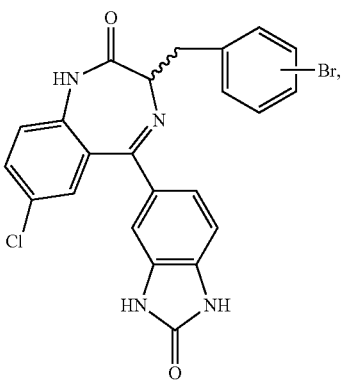

-continued
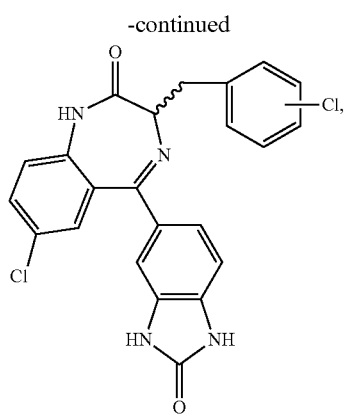
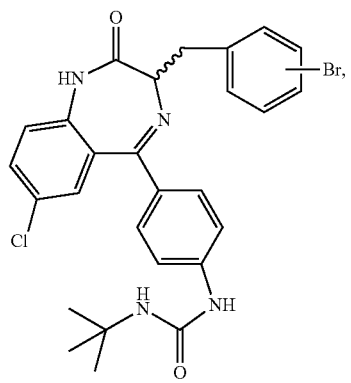
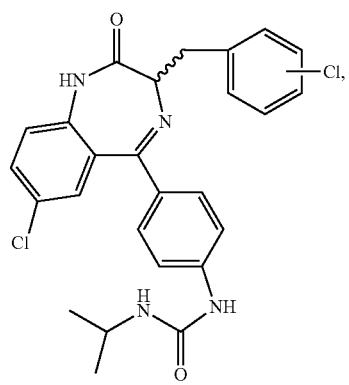
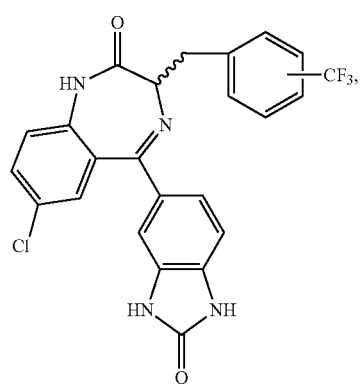
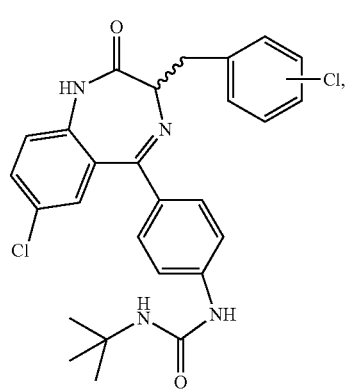
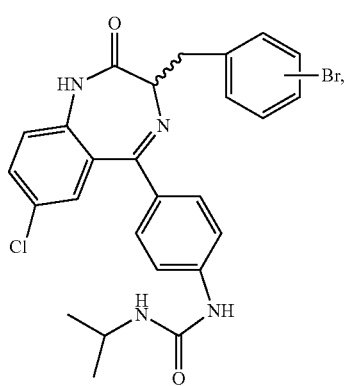
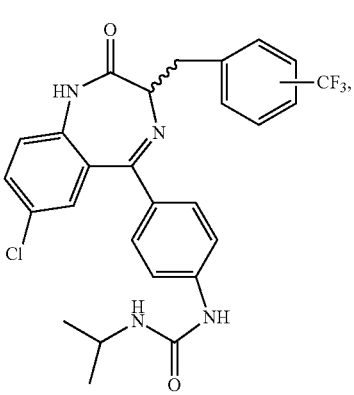

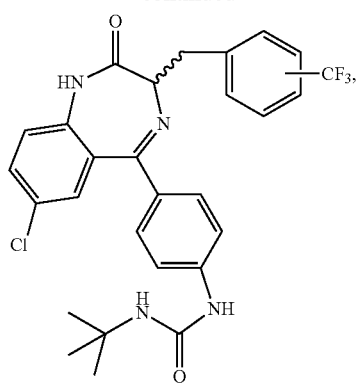
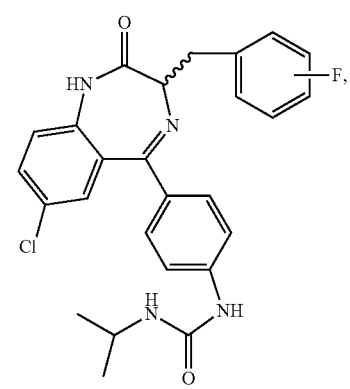
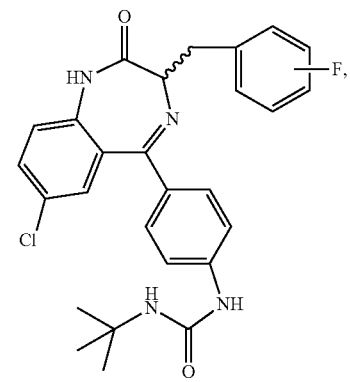
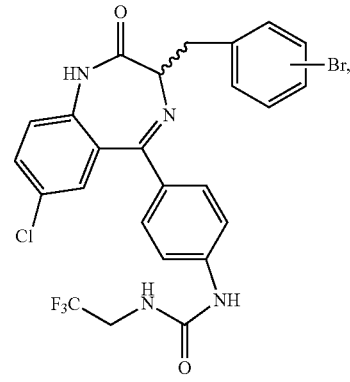
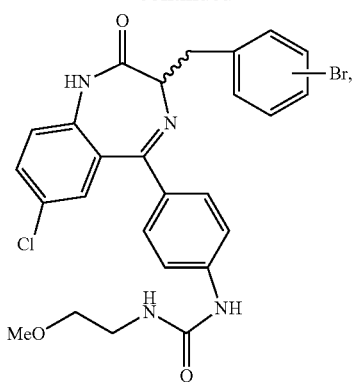
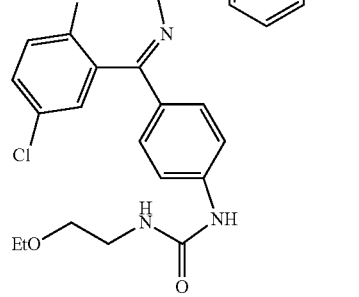
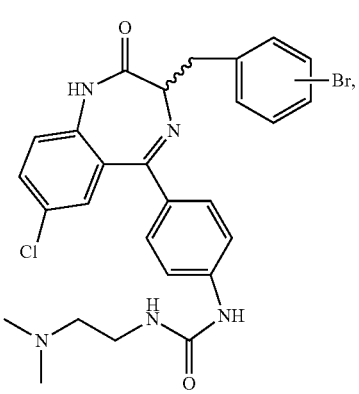
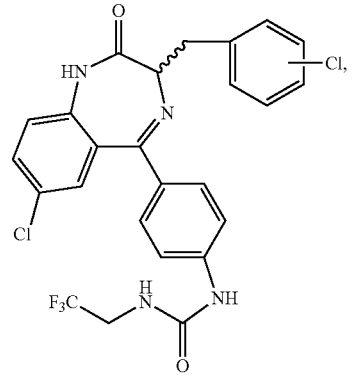

-continued
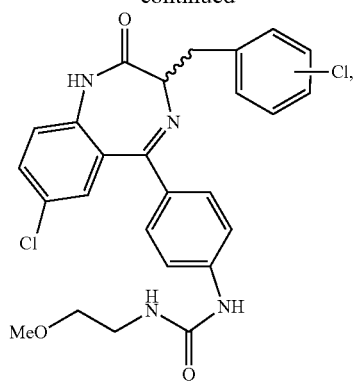
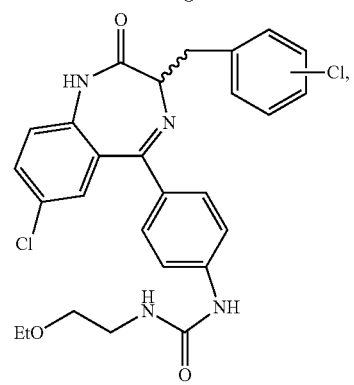
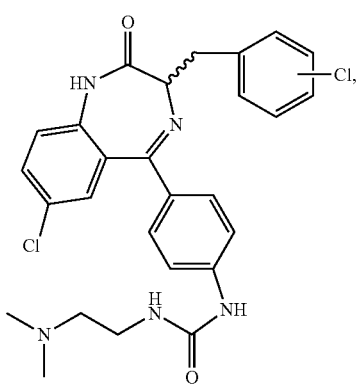
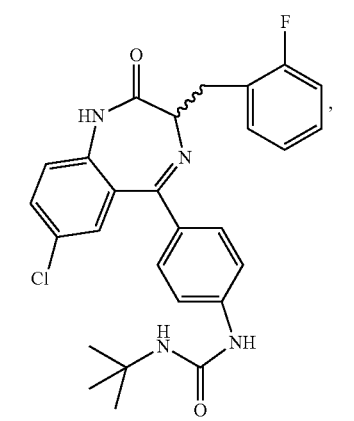
-continued
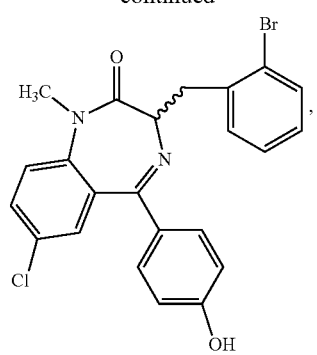
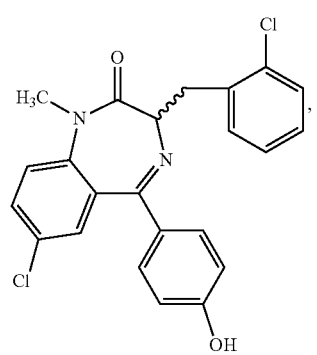
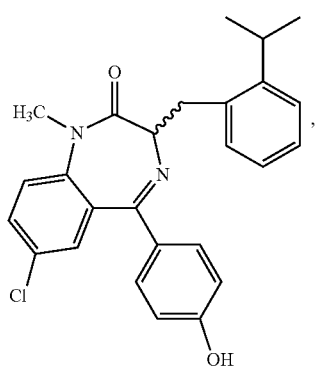
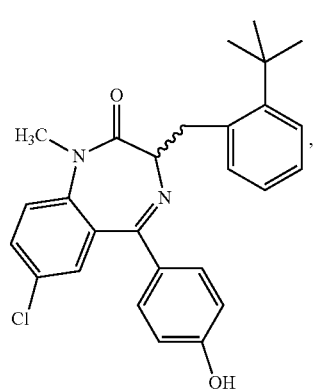

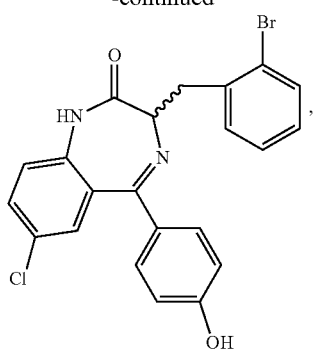
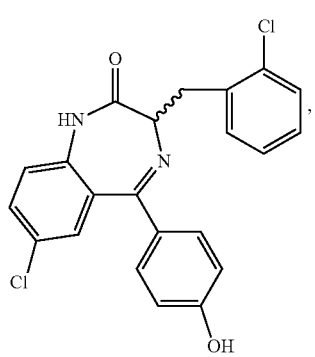
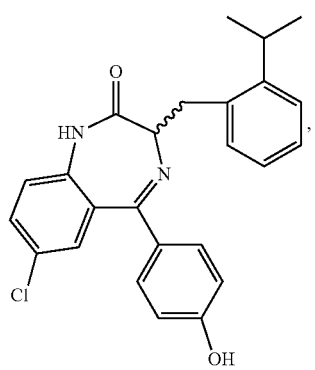
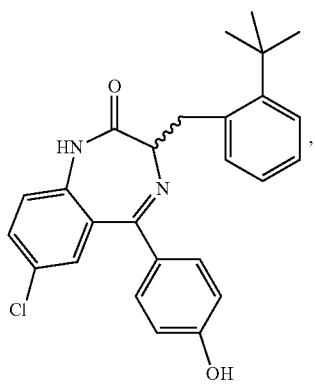
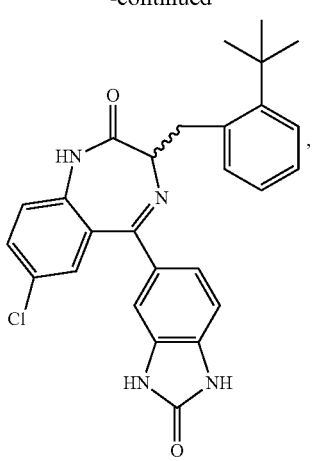
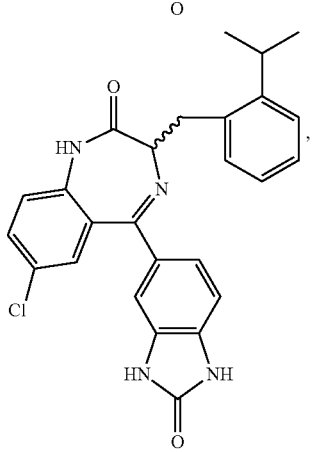
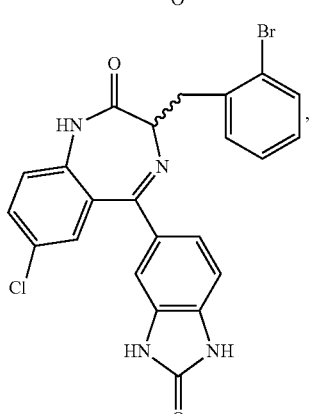
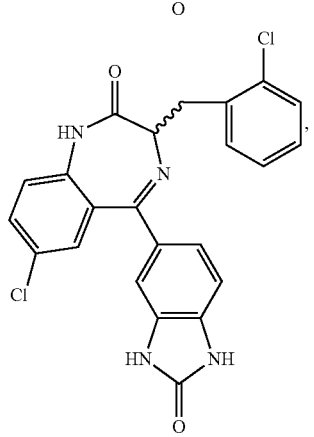

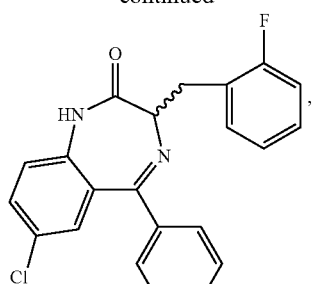
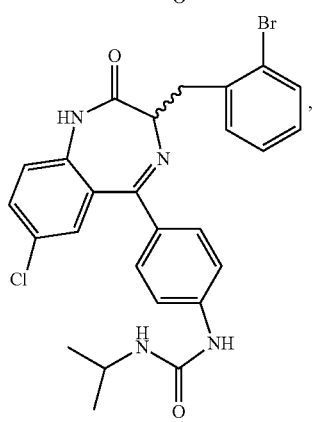
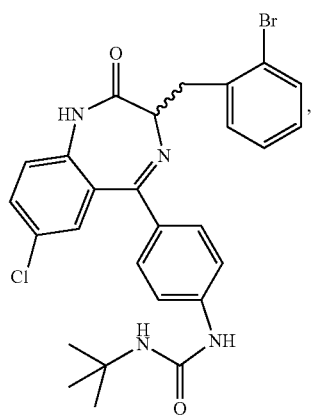
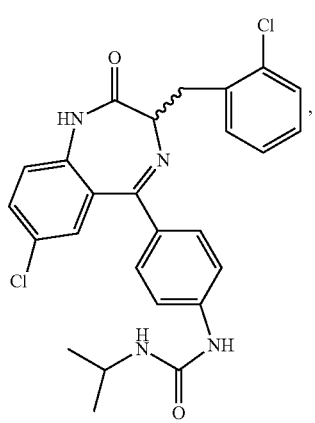
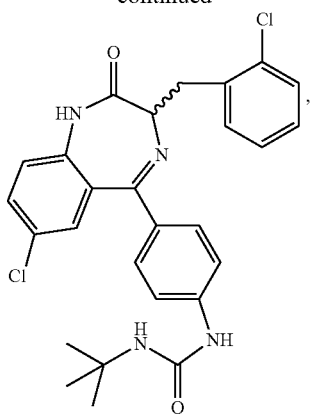
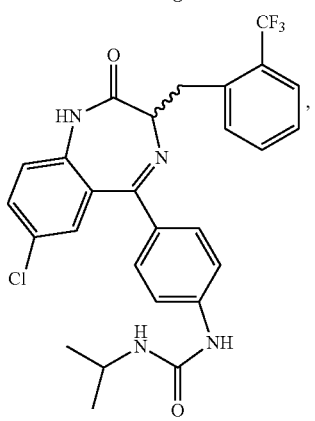
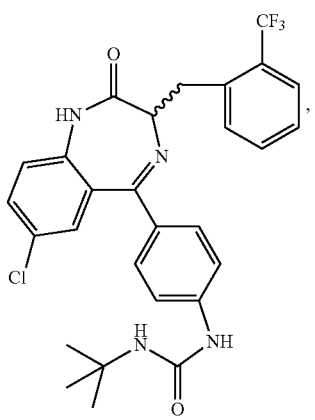
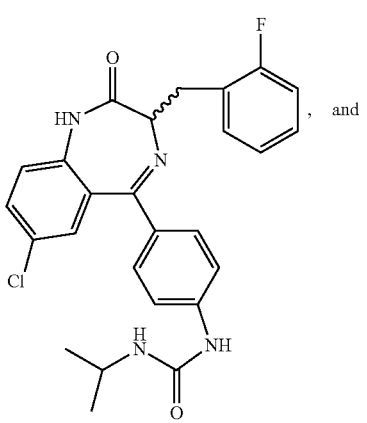

-continued

In certain embodiments, the compound is selected from the group consisting of (Z)-1-(4-(3-(2-bromobenzyl)-7-chloro-2-oxo-2,3-dihydro-1H-benzo[e][1,4]diazepin-5-yl)phenyl)-3-isopropylurea; (Z)-1-(4-(7-chloro-2-oxo-3-(2-(trifluoromethyl)benzyl)-2,3-dihydro-1H-benzo[e][1,4]diazepin-5-yl)phenyl)-3-isopropylurea; (Z)-1-(4-(7-chloro-3-(2-fluorobenzyl)-2-oxo-2,3-dihydro-1H-benzo[e][1,4]diazepin-5-yl)phenyl)-3-isopropylurea; (Z)-1-(4-(7-chloro-3-(2-chlorobenzyl)-2-oxo-2,3-dihydro-1H-benzo[e][1,4]diazepin-5-yl)phenyl)-3-isopropylurea; (Z)-1-(4-(7-chloro-3-(2-chlorobenzyl)-2-oxo-2,3-dihydro-1H-benzo[e][1,4]diazepin-5-yl)phenyl)-3-methylurea; (Z)-1-(4-(7-chloro-3-(2-chlorobenzyl)-2-oxo-2,3-dihydro-1H-benzo[e][1,4]diazepin-5-yl)phenyl)-3-(2-(dimethylamino)ethyl)urea; (Z)-1-(4-(7-chloro-3-(2-chlorobenzyl)-2-oxo-2,3-dihydro-1H-benzo[e][1,4]diazepin-5-yl)phenyl)-3-(2,2,2-trifluoroethyl)urea; (Z)-1-(4-(7-chloro-3-(2-chlorobenzyl)-2-oxo-2,3-dihydro-1H-benzo[e][1,4]diazepin-5-yl)phenyl)-3-cyclopropylurea; (Z)-1-(4-(7-chloro-3-(2-chlorobenzyl)-2-oxo-2,3-dihydro-1H-benzo[e][1,4]diazepin-5-yl)phenyl)-3-(2-methoxyethyl)urea; (Z)-1-(4-(7-chloro-3-(2-chlorobenzyl)-2-oxo-2,3-dihydro-1H-benzo[e][1,4]diazepin-5-yl)phenyl)-3-(2-ethoxyethyl)urea; (Z)-1-(4-(3-(2-bromobenzyl)-7-chloro-2-oxo-2,3-dihydro-1H-benzo[e][1,4]diazepin-5-yl)phenyl)-3-methylurea; (Z)-1-(4-(3-(2-bromobenzyl)-7-chloro-2-oxo-2,3-dihydro-1H-benzo[e][1,4]diazepin-5-yl)phenyl)-3-(2-(dimethylamino)ethyl)urea; (Z)-1-(4-(3-(2-bromobenzyl)-7-chloro-2-oxo-2,3-dihydro-1H-benzo[e][1,4]diazepin-5-yl)phenyl)-3-(2,2,2-trifluoroethyl)urea; (Z)-1-(4-(3-(2-bromobenzyl)-7-chloro-2-oxo-2,3-dihydro-1H-benzo[e][1,4]diazepin-5-yl)phenyl)-3-cyclopropylurea; (Z)-1-(4-(3-(2-bromobenzyl)-7-chloro-2-oxo-2,3-dihydro-1H-benzo[e][1,4]diazepin-5-yl)phenyl)-3-(2-methoxyethyl)urea; (Z)-1-(4-(3-(2-bromobenzyl)-7-chloro-2-oxo-2,3-dihydro-1H-benzo[e][1,4]diazepin-5-yl)phenyl)-3-(2-ethoxyethyl)urea; (Z)-7-chloro-5-(4-hydroxyphenyl)-3-(2-methylbenzyl)-1H-benzo[e][1,4]diazepin-2(3H)-one; (Z)-7-chloro-5-(4-hydroxyphenyl)-1-methyl-3-(2-methylbenzyl)-1H-benzo[e][1,4]diazepin-2(3H)-one; (Z)-7-chloro-5-(4-hydroxyphenyl)-3-(3-methylbenzyl)-1H-benzo[e][1,4]diazepin-2(3H)-one; (Z)-7-chloro-5-(4-hydroxyphenyl)-1-methyl-3-(3-methylbenzyl)-1H-benzo[e][1,4]diazepin-2(3H)-one; (Z)-7-chloro-5-(4-hydroxyphenyl)-3-(4-methylbenzyl)-1H-benzo[e][1,4]diazepin-2(3H)-one; (Z)-7-chloro-5-(4-hydroxyphenyl)-1-methyl-3-(4-methylbenzyl)-1H-benzo[e][1,4]diazepin-2(3H)-one; (Z)-7-chloro-3-(2-ethylbenzyl)-5-(4-hydroxyphenyl)-1H-benzo[e][1,4]diazepin-2(3H)-one; (Z)-7-chloro-3-(2-ethylbenzyl)-5-(4-hydroxyphenyl)-1-methyl-1H-benzo[e][1,4]diazepin-2(3H)-one; (Z)-7-chloro-3-(3-ethylbenzyl)-5-(4-hydroxyphenyl)-1H-benzo[e][1,4]diazepin-2(3H)-one; (Z)-7-chloro-3-(3-ethylbenzyl)-5-(4-hydroxyphenyl)-1-methyl-1H-benzo[e][1,4]diazepin-2(3H)-one; (Z)-7-chloro-3-(4-ethylbenzyl)-5-(4-hydroxyphenyl)-1-methyl-1H-benzo[e][1,4]diazepin-2(3H)-one; (Z)-7-chloro-3-(4-ethylbenzyl)-5-(4-hydroxyphenyl)-1H-benzo[e][1,4]diazepin-2(3H)-one; (Z)-7-chloro-5-(4-hydroxyphenyl)-3-(3-isopropylbenzyl)-1H-benzo[e][1,4]diazepin-2(3H)-one; (Z)-7-chloro-5-(4-hydroxyphenyl)-3-(3-isopropylbenzyl)-1-methyl-1H-benzo[e][1,4]diazepin-2(3H)-one; (Z)-7-chloro-5-(4-hydroxyphenyl)-3-(4-isopropylbenzyl)-1H-benzo[e][1,4]diazepin-2(3H)-one; (Z)-7-chloro-5-(4-hydroxyphenyl)-3-(4-isopropylbenzyl)-1-methyl-1H-benzo[e][1,4]diazepin-2(3H)-one; (Z)-7-chloro-5-(4-hydroxyphenyl)-1-methyl-3-(2-(trifluoromethyl)benzyl)-1H-benzo[e][1,4]diazepin-2(3H)-one; (Z)-3-(2-bromobenzyl)-7-chloro-5-(4-hydroxyphenyl)-1H-benzo[e][1,4]diazepin-2(3H)-one; (Z)-7-chloro-3-(2-chlorobenzyl)-5-(4-hydroxyphenyl)-1-methyl-1H-benzo[e][1,4]diazepin-2(3H)-one; (Z)-3-(2-bromobenzyl)-7-chloro-1-methyl-5-(2-oxo-2,3-dihydro-1H-benzo[d]imidazol-5-yl)-1H-benzo[e][1,4]diazepin-2(3H)-one; (Z)-7-chloro-5-(4-hydroxyphenyl)-1-methyl-3-(4-(trifluoromethyl)benzyl)-1H-benzo[e][1,4]diazepin-2(3H)-one; (Z)-3-(3-bromobenzyl)-7-chloro-5-(4-hydroxyphenyl)-1-methyl-1H-benzo[e][1,4]diazepin-2(3H)-one; (Z)-3-(4-bromobenzyl)-7-chloro-5-(4-hydroxyphenyl)-1-methyl-1H-benzo[e][1,4]diazepin-2(3H)-one; (Z)-7-chloro-3-(3-chlorobenzyl)-5-(4-hydroxyphenyl)-1-methyl-1H-benzo[e][1,4]diazepin-2(3H)-one; (Z)-7-chloro-3-(2-chlorobenzyl)-5-(4-hydroxyphenyl)-1H-benzo[e][1,4]diazepin-2(3H)-one; (Z)-7-chloro-3-(2-chlorobenzyl)-5-(2-oxo-2,3-dihydro-1H-benzo[d]imidazol-5-yl)-1H-benzo[e][1,4]diazepin-2(3H)-one; and (Z)-7-chloro-5-(2-oxo-2,3-dihydro-1H-benzo[d]imidazol-5-yl)-3-(2-(trifluoromethyl)benzyl)-1H-benzo[e][1,4]diazepin-2(3H)-one; (Z)-7-chloro-1-methyl-5-(2-oxo-2,3-dihydro-1H-benzo[d]imidazol-5-yl)-3-(2-(trifluoromethyl)benzyl)-1H-benzo[e][1,4]diazepin-2(3H)-one; and (Z)-7-chloro-3-(2-chlorobenzyl)-1-methyl-5-(2-oxo-2,3-dihydro-1H-benzo[d]imidazol-5-yl)-1H-benzo[e][1,4]diazepin-2(3H)-one; and pharmaceutically acceptable salts thereof.

In certain embodiments, the present invention provides methods for treating cells, comprising a) providing i) target cells; and ii) at least one of the exemplary compounds of the present invention (see, e.g., Section III—Exemplary Compounds). In some embodiments, the treating comprises one or more of inducing cellular growth arrest in the target cells, inducing cellular death in the target cells, and inducing cellular apoptosis in the target cells. In some embodiments, the target cells are in a subject having, for example, an immune disorder (e.g., an autoimmune disorder), a hyperproliferative disorder, an epidermal hyperplasia disorder, a pigment disorder, a cardiovascular disorder, and/or a viral disorder. In some embodiments, the target cells are in vitro cells, in vivo cells, or ex vivo cells. In other preferred embodiments, the target cells are cancer cells. In still other preferred embodiments, the target cells are B cells, T cells, or granulocytes.

The present invention further provides methods of treating an immune disorder comprising administering to a subject an effective amount of at least one of the exemplary compounds of the present invention (see, e.g., Section III—Exemplary Compounds). In some embodiments, the immune disorder includes, but is not limited to, an autoimmune hemolytic anemia, autoimmune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, and idiopathic thrombocytopenic thrombotic purpura.

The present invention further provides methods of treating cancer and/or a cancer-related disorder comprising administering to a subject an effective amount of at least one of the exemplary compounds of the present invention (see, e.g., Section III—Exemplary Compounds). The present invention is not limited to a particular type of cancer (e.g., tumor, a neoplasm, a lymphoma, or a leukemia). In some embodiments, the composition further comprises an anti-cancer agent.

In some embodiments, the present invention provides a method for regulating cell death comprising providing target cells having oligomycin sensitivity conferring protein(s) and the $F_1$ subunit of a mitochondrial $F_1F_0$-ATPase; a composition comprising at least one of the exemplary compounds of the present invention (see, e.g., Section III—Exemplary Compounds); and exposing the cells to the composition under conditions such that the composition binds to the oligomycin sensitivity conferring protein(s) so as to increase superoxide levels or alter cellular ATP levels in the cells. In some embodiments, the target cells are in vitro cells, in vivo cells, and/or ex vivo cells. In some embodiments, the target cells are cancer cells. In some embodiments, the target cells comprise B cells, T cells, and granulocytes. In some embodiments, the exposing step results in an increase in cell death of the target cells.

In certain embodiments, the present invention provides a composition comprising a drug-eluting stent media; wherein the drug-eluting stent media comprises a pharmaceutical composition comprising at least one of the exemplary compounds of the present invention (see, e.g., Section III—Exemplary Compounds). In some embodiments, the present invention provides a method for treating a vessel comprising exposing a vessel of a subject to the composition. In some embodiments, the vessel is an occluded vessel and/or a cardiac vessel.

In certain embodiments, the present invention provides a method of regulating hyperproliferating epithelium cells, comprising providing a sample with hyperproliferating epithelium cells, and a composition comprising at least one of the exemplary compounds of the present invention (see, e.g., Section III—Exemplary Compounds); and applying the composition to the sample. In some embodiments, applying of the composition to the sample decreases Erk½ activation within the sample. In some embodiments, applying the composition to the sample inhibits keratinocyte proliferation within the sample. In some embodiments, the composition further comprises a topical corticosteroid (e.g., triamcinolone acetonide 0.1% cream and betamethasone dipropionate 0.05% cream). In some embodiments, the composition further comprises coal tar 2-10%. In some embodiments, the composition further comprises a vitamin D-3 analog (e.g., calcipotriene). In some embodiments, the composition further comprises a keratolytic agent (e.g., anthralin 0.1-1%). In some embodiments, the composition further comprises a topical retinoid (e.g., tretinoin, and tazarotene). In some embodiments, the sample is a living subject. In some embodiments, the living subject is a human being suffering from epidermal hyperplasia. In some embodiments, the living subject has psoriasis.

In certain embodiments, the present invention provides a pharmaceutical composition comprising at least one of the exemplary compounds of the present invention (see, e.g., Section III—Exemplary Compounds) and a pharmaceutically acceptable diluent or carrier. In certain embodiments, the pharmaceutical composition further comprises another therapeutic agent.

In certain embodiments, the exemplary compounds of the present invention (see, e.g., Section III—Exemplary Compounds) are useful in treating $F_1F_0$-ATP hydrolase associated disorders. Examples of $F_1F_0$-ATP hydrolase associated disorders include, but are not limited to, myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, pregnancy and fetal loss, and diabetic complications comprising retinopathy, nephropathy and neuropathy.

In certain embodiments, the present invention provides a method of treating a mitochondrial $F_1F_0$-ATP hydrolase associated disorder in a patient comprising administering to the patient in need of such treatment an effective amount of at least one exemplary compound of the present invention (see, e.g., Section III—Exemplary Compounds). In some embodiments, the mitochondrial $F_1F_0$-ATP hydrolase disorder includes, but is not limited to, myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, pregnancy and fetal loss, and diabetic complications comprising retinopathy, nephropathy and neuropathy.

In certain embodiments, the present invention provides methods of treating disorders comprising inhibiting the activity of ATP synthase complexes in cells affected by the disorder through exposing the affected cells to a composition able to bind the oligomycin sensitivity conferring protein of the ATP synthase complexes, wherein the disorder comprises a bacterial infection, a viral infection, a fungal infection, a parasitic infection, a prion disorder, a disorder involving aberrant angiogenesis, a disorder involving aberrant blood pressure regulation, and a disorder involving aberrant HDL/LDL regulation. In some embodiments, the ATP synthase complexes are mitochondrial $F_1F_0$-ATPase complexes.

In certain embodiments, the present invention provides a method of identifying therapeutic compositions, comprising a) providing a sample comprising mitochondrial $F_1F_0$-ATPase, and molecular modeling software; b) identifying a candidate $F_1F_0$-ATPase inhibitor with the molecular modeling software; c) contacting the inhibitor with the sample; d) measuring the kcat/Km of the mitochondrial $F_1F_0$-ATPase; and e) selecting the compositions that bind predominantly a $F_1F_0$-ATPase-substrate complex and that do not alter the kcat/Km ratio of the mitochondrial $F_1F_0$-ATPase upon binding of the mitochondrial $F_1F_0$-ATPase as therapeutic compositions. In some embodiments, the method further comprises the step of f) testing the selected compositions in an animal to identify low toxicity and ability to treat an immune disorder (e.g., an autoimmune disorder). In some embodiments, the sample further comprises mitochondria. In some embodiments, the $F_1F_0$-ATPase is a pure enzyme. In some embodiments, the $F_1F_0$-ATPase is located in a sub-mitochondrial particle. In some embodiments, the kcat/Km ratio is measured by determining the rate of ATP hydrolysis or synthesis as a function of ATP concentration and inhibitor concentration. In other preferred embodiments, the kcat/Km ratio is calculated from Km Vmax, and the enzyme concentration.

In certain embodiments, the compounds of the present invention can be used to treat a disorder by administering an effective amount of the compound, usually in a pharmaceutical formulation comprising the compound of the invention and a pharmaceutically acceptable carrier, to a subject, for example, a human, in need thereof. The compound should be administered to ameliorate at least one symptom of the disorder. Exemplary disorders treatable by one or more compounds of the invention, include, without limitation, immune disorders, hyperproliferative disorders and chronic inflammatory disease. With regard to immune disorders, the compounds can be used to treat graft versus host disease, rheumatoid arthritis, and systemic lupus erythematosus. In addition, the compounds can be used to reduce or eliminate tissue or organ rejection following a transplant procedure. With regard to hyperproliferative disorders, the compounds of the invention can be used to treat cancer, which can be either malignant or benign. Exemplary cancers that can be treated include, for example, adenomas, adenocarcinomas, carcinomas, leukemias, lymphomas, melanomas, myelomas, sarcomas, and teratomas. In addition, it is contemplated that the compounds of the invention can be used to treat cancers of the bladder and the renal system, brain, breast, cervix, colon, lung, ovaries, prostate, rectum. With regard to chronic inflammatory disease, the compounds of the invention can be used to treat asthma, psoriasis, and inflammatory bowel disease.

DEFINITIONS

To facilitate an understanding of the present invention, a number of terms and phrases are defined below.

As used herein, the term "substituted aliphatic" refers to an alkane possessing less than 10 carbons where at least one of the aliphatic hydrogen atoms has been replaced by a halogen, an amino, a hydroxy, an alkoxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of no more than three fused rings at least one of which is aromatic, and where at least one of the hydrogen atoms on a ring carbon has been replaced by a halogen, an amino, a hydroxy, an alkoxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to a cycloalkane possessing less than 8 carbons or a fused ring system consisting of no more than three fused cycloaliphatic rings. Examples of such include, but are not limited to, decalin and the like.

As used herein, the term "substituted cycloaliphatic" refers to a cycloalkane possessing less than 10 carbons or a fused ring system consisting of no more than three fused rings, and where at least one of the aliphatic hydrogen atoms has been replaced by a halogen, a nitro, a thio, an amino, a hydroxy, an alkoxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such include, but are not limited to, morpholino and the like.

As used herein, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

The term "alkyl" is art-recognized and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 8 or fewer carbon atoms in its backbone (e.g., $C_1$-$C_8$ for straight chain, $C_3$-$C_8$ for branched chain), and alternatively, about 4 or fewer.

The term "substituted alkyl" is art-recognized and refers to an alkyl moiety having a substituent replacing a hydrogen atom on one or more carbon atoms of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. In a preferred embodiment, the substituted alkyl is an alkyl moiety having a fluorine atom replacing a hydrogen atom on one or more carbon atoms of the hydrocarbon backbone, e.g., —$CH_2F$, —$CHF_2$, —$CF_3$, and the like.

The term "derivative" of a compound, as used herein, refers to a chemically modified compound wherein the chemical modification takes place either at a functional group of the compound or on the aromatic ring.

The term "epidermal hyperplasia," as used herein, refers to an abnormal multiplication or increase in the number of normal cells in normal arrangement in epidermal tissue. Epidermal hyperplasia is a characteristic of numerous disorders, including but not limited to, psoriasis.

The term "keratinocyte" as used herein, refers to a skin cell of the keratinized layer of the epidermis.

The term "fibroblast" as used herein, refers to mesodermally derived resident cells of connective tissue that secrete fibrillar procollagen, fibronectin and collegenase.

The term "pigment disorder" as used herein, refers to disorders involving skin pigment (e.g., melanin). Examples of pigment disorders include, but are not limited to, all forms of albinism, melasma, pigment loss after skin damage, and vitiligo.

The term "stent" or "drug-eluting stent," as used herein, refers to any device which when placed into contact with a site in the wall of a lumen to be treated, will also place fibrin at the lumen wall and retain it at the lumen wall. This can include especially devices delivered percutaneously to treat coronary artery occlusions and to seal dissections or aneurysms of splenic, carotid, iliac and popliteal vessels. The stent can also have underlying polymeric or metallic structural elements onto which the fibrin is applied or the stent can be a composite of fibrin intermixed with a polymer. For example, a deformable metal wire stent such as that disclosed in U.S. Pat. No. 4,886,062, herein incorporated by reference, could be coated with fibrin as set forth above in one or more coats (i.e., polymerization of fibrin on the metal framework by application of a fibrinogen solution and a solution of a fibrinogen-coagulating protein) or provided with an attached fibrin preform such as an encircling film of fibrin. The stent and fibrin could then be placed onto the balloon at a distal end of a balloon catheter and delivered by conventional percutaneous means (e.g. as in an angioplasty procedure) to the site of the restriction or closure to be treated where it would then be expanded into contact with the body lumen by inflating the balloon. The catheter can then be withdrawn, leaving the fibrin stent of the present invention in place at the treatment site. The stent may therefore provide both a supporting structure for the lumen at the site of treatment and also a structure supporting the secure placement of fibrin at the lumen wall. Generally, a drug-eluting stent allows for an active release of a particular drug at the stent implementation site.

As used herein, the term "catheter" refers generally to a tube used for gaining access to a body cavity or blood vessel.

As used herein, the term "valve" or "vessel" refers to any lumen within a mammal. Examples include, but are not limited to, arteries, veins, capillaries, and biological lumen.

As used herein, the term "restenosis" refers to any valve which is narrowed. Examples include, but are not limited to, the reclosure of a peripheral or coronary artery following trauma to that artery caused by efforts to open a stenosed portion of the artery, such as, for example, by balloon dilation, ablation, atherectomy or laser treatment of the artery.

As used herein, "angioplasty" or "balloon therapy" or "balloon angioplasty" or "percutaneous transluminal coronary angioplasty" refers to a method of treating blood vessel disorders that involves the use of a balloon catheter to enlarge the blood vessel and thereby improve blood flow.

As used herein, "cardiac catheterization" or "coronary angiogram" refers to a test used to diagnose coronary artery disease using a catheterization procedure. Such a procedure may involve, for example, the injection of a contrast dye into the coronary arteries via a catheter, permitting the visualization of a narrowed or blocked artery.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by the dysregulation of apoptotic processes.

As used herein, the terms "anticancer agent," or "conventional anticancer agent" refer to any chemotherapeutic compounds, radiation therapies, or surgical interventions, used in the treatment of cancer.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

In some embodiments, the "target cells" of the compositions and methods of the present invention include, refer to, but are not limited to, lymphoid cells or cancer cells. Lymphoid cells include B cells, T cells, and granulocytes. Granulocytes include eosinophils and macrophages. In some embodiments, target cells are continuously cultured cells or uncultured cells obtained from patient biopsies.

Cancer cells include tumor cells, neoplastic cells, malignant cells, metastatic cells, and hyperplastic cells. Neoplastic cells can be benign or malignant. Neoplastic cells are benign if they do not invade or metastasize. A malignant cell is one that is able to invade and/or metastasize. Hyperplasia is a pathologic accumulation of cells in a tissue or organ, without significant alteration in structure or function.

In one specific embodiment, the target cells exhibit pathological growth or proliferation. As used herein, the term "pathologically proliferating or growing cells" refers to a localized population of proliferating cells in an animal that is not governed by the usual limitations of normal growth.

As used herein, the term "un-activated target cell" refers to a cell that is either in the $G_o$ phase or one in which a stimulus has not been applied.

As used herein, the term "activated target lymphoid cell" refers to a lymphoid cell that has been primed with an appropriate stimulus to cause a signal transduction cascade, or alternatively, a lymphoid cell that is not in $G_o$ phase. Activated lymphoid cells may proliferate, undergo activation induced cell death, or produce one or more of cytotoxins, cytokines, and other related membrane-associated proteins characteristic of the cell type (e.g., $CD8^+$ or $CD4^+$). They are also capable of recognizing and binding any target cell that displays a particular antigen on its surface, and subsequently releasing its effector molecules.

As used herein, the term "activated cancer cell" refers to a cancer cell that has been primed with an appropriate stimulus to cause a signal transduction. An activated cancer cell may or may not be in the $G_O$ phase.

An activating agent is a stimulus that upon interaction with a target cell results in a signal transduction cascade. Examples of activating stimuli include, but are not limited to, small molecules, radiant energy, and molecules that bind to cell activation cell surface receptors. Responses induced by activation stimuli can be characterized by changes in, among others, intracellular $Ca^{2+}$, superoxide, or hydroxyl radical levels; the activity of enzymes like kinases or phosphatases; or the energy state of the cell. For cancer cells, activating agents also include transforming oncogenes.

In one aspect, the activating agent is any agent that binds to a cell surface activation receptor. These can be selected from the group consisting of a T cell receptor ligand, a B cell activating factor ("BAFF"), a TNF, a Fas ligand (FasL), a CD40 ligand, a proliferation inducing ligand ("APRIL"), a cytokine, a chemokine, a hormone, an amino acid (e.g., glutamate), a steroid, a B cell receptor ligand, gamma irradiation, UV irradiation, an agent or condition that enhances cell stress, or an antibody that specifically recognizes and binds a cell surface activation receptor (e.g., anti-CD4, anti-CD8, anti-CD20, anti-TACI, anti-BCMA, anti-TNF receptor, anti-CD40, anti-CD3, anti-CD28, anti-B220, anti-CD38, anti-CD19, and anti-CD21). BCMA is B cell maturation antigen receptor and TACI is transmembrane activator and CAML interactor. (Gross, A. et al. (2000); Laabi, Y. et al. (1992) and Madry, C. et al. (1998)). Antibodies include monoclonal or polyclonal or a mixture thereof.

Examples of a T cell ligand include, but are not limited to, a peptide that binds to an MHC molecule, a peptide MHC complex, or an antibody that recognizes components of the T cell receptor.

Examples of a B cell ligand include, but are not limited to, a molecule or antibody that binds to or recognizes components of the B cell receptor.

Examples of reagents that bind to a cell surface activation receptor include, but are not limited to, the natural ligands of these receptors or antibodies raised against them (e.g., anti-CD20). RITUXIN (Genentech, Inc., San Francisco, Calif.) is a commercially available anti-CD 20 chimeric monoclonal antibody.

Examples of agents or conditions that enhance cell stress include heat, radiation, oxidative stress, or growth factor withdrawal and the like. Examples of growth factors include, but are not limited to serum, IL-2, platelet derived growth factor ("PDGF"), and the like.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "dysregulation of the process of cell death" refers to any aberration in the ability of (e.g., predisposition) a cell to undergo cell death via either necrosis or apoptosis. Dysregulation of cell death is associated with or induced by a variety of conditions, including for example, immune disorders (e.g., autoimmune disorders) (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo, invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium. Hyperproliferative disorder includes cancers, such as myeloma, bladder cancer, and renal cancer.

The pathological growth of activated lymphoid cells often results in an immune disorder (e.g., autoimmune disorder) or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, Celiac Sprue, chronic fatigue syndrome, Crohn's disease, dermatomyositis, fibromyalgia, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, and the like. Graft versus host disease can result from an immune response to transplanted tissues, organs and the like (e.g., bone marrow, solid organ, skin, etc.).

As used herein, the term "chronic inflammatory condition" refers to a condition wherein the organism's immune cells are activated. Such a condition is characterized by a persistent inflammatory response with pathologic sequelae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Immune diseases such as rheumatoid arthritis and systemic lupus erythematosus can also result in a chronic inflammatory state.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Certain compounds described herein may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In particular, the generic chemical structures presented herein may contain asymmetric carbon atoms, and/or a substituent on the generic chemical structures may contain asymmetric carbon atoms. The generic chemical structures include compounds of all stereoisomeric forms, including enantiomers, diastereomers, and racemic mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group is cleaved to provide the pure desired enantiomer. Alternatively, where the molecule contains a basic functional group, such as amino, or an acidic functional group, such as carboxyl, diastereomeric salts may be formed with an appropriate optically-active acid or base, followed by resolution of the diastereomers thus formed by fractional crystallization or chromatographic means well known in the art, and subsequent recovery of the pure enantiomers.

As used herein, the terms "solid phase supports" or "solid supports," are used in their broadest sense to refer to a number of supports that are available and known to those of ordinary skill in the art. Solid phase supports include, but are not limited to, silica gels, resins, derivatized plastic films, glass beads, cotton, plastic beads, alumina gels, and the like. As used herein, "solid supports" also include synthetic antigen-presenting matrices, cells, liposomes, and the like. A suitable solid phase support may be selected on the basis of desired end use and suitability for various protocols. For example, for peptide synthesis, solid phase supports may refer to resins such as polystyrene (e.g., PAM-resin obtained from Bachem, Inc., Peninsula Laboratories, etc.), POLYHIPE) resin (obtained from Aminotech, Canada), polyamide resin (obtained from Peninsula Laboratories), polystyrene resin grafted with polyethylene glycol (TENTAGEL, Rapp Polymere, Tubingen, Germany) or polydimethylacrylamide resin (obtained from Milligen/Biosearch, California).

As used herein, the term "pathogen" refers a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process which is well known in the art. (See e.g., Finegold and Martin, Diagnostic Microbiology, 6th Ed., CV Mosby St. Louis, pp. 13-15 [1982]). "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "microorganism" refers to any species or type of microorganism, including but not limited to, bacteria, archaea, fungi, protozoans, mycoplasma, and parasitic organisms. The present invention contemplates that a number of microorganisms encompassed therein will also be pathogenic to a subject.

As used herein, the term "fungi" is used in reference to eukaryotic organisms such as the molds and yeasts, including dimorphic fungi.

As used herein, the term "virus" refers to minute infectious agents, which with certain exceptions, are not observable by light microscopy, lack independent metabolism, and are able to replicate only within a living host cell. The individual particles (i.e., virions) typically consist of nucleic acid and a protein shell or coat; some virions also have a lipid containing membrane. The term "virus" encompasses all types of viruses, including animal, plant, phage, and other viruses.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer to the removal of undesired components from a sample. As used herein, the term "substantially purified" refers to molecules that are at least 60% free, preferably 75% free, and most preferably 90%, or more, free from other components with which they usually associated.

As used herein, the term "antigen binding protein" refers to proteins which bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]).

According to the invention, techniques described for the production of single chain antibodies (U.S. Pat. No. 4,946, 778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "modulate" refers to the activity of a compound (e.g., a compound of the present invention) to affect (e.g., to promote or retard) an aspect of cellular function, including, but not limited to, cell growth, proliferation, apoptosis, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

DETAILED DESCRIPTION OF THE INVENTION

The present invention provides novel chemical compounds, methods for their discovery, and their therapeutic, research, and diagnostic use. In particular, the present invention provides benzodiazepine compounds, and methods of using benzodiazepine derivatives and related compounds as therapeutic agents to treat a number of conditions associated with the faulty regulation of the processes of programmed cell death, autoimmunity, inflammation, and hyperproliferation, and the like.

Exemplary compositions and methods of the present invention are described in more detail in the following sections: I. Modulators of Cell Death; II. Modulators of Cell Growth and Proliferation; III. Exemplary Compounds; IV. Pharmaceutical Compositions, Formulations, and Exemplary Administration Routes and Dosing Considerations; V. Drug screens; and VI. Therapeutic Applications.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Modulators of Cell Death

In some embodiments, it is contemplated that the present invention regulates apoptosis through the exposure of cells to compounds. The effect of compounds can be measured by detecting any number of cellular changes. Cell death may be assayed as described herein and in the art. In some embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemo-cytometry, or MTT dye conversion assay. Alternatively, the cell may be analyzed for the expression of genes or gene products associated with aberrations in apoptosis or necrosis.

In some embodiments, it is contemplated that exposing the present invention to a cell induces apoptosis. In some embodiments, it is contemplated that the present invention causes an initial increase in cellular ROS levels (e.g., $O_2^-$). In further embodiments, it is contemplated that exposure of the compounds of the present invention to a cell causes an increase in cellular $O_2^-$ levels. In still further embodiments, it is contemplated that the increase in cellular $O_2^-$ levels resulting from the compounds of the present invention is detectable with a redox-sensitive agent that reacts specifically with $O_2^-$ (e.g., dihyroethedium (DHE)).

In other embodiments, it is contemplated that increased cellular $O_2^-$ levels resulting from compounds of the present invention diminish after a period of time (e.g., 10 minutes). In other embodiments, it is contemplated that increased cellular $O_2^-$ levels resulting from the compounds of the present invention diminish after a period of time and increase again at a later time (e.g., 10 hours). In further embodiments, it is contemplated that increased cellular $O_2^-$ levels resulting from the compounds of the present invention diminish at 1 hour and increase again after 4 hours. In some embodiments, it is contemplated that an early increase in cellular $O_2^-$ levels, followed by a diminishing in cellular $O_2^-$ levels, followed by another increase in cellular $O_2^-$ levels resulting from the compounds of the present invention is due to different cellular processes (e.g., bimodal cellular mechanisms).

In some embodiments, it is contemplated that the present invention causes a collapse of a cell's mitochondrial $\Delta\Psi_m$. In some embodiments, it is contemplated that a collapse of a cell's mitochondrial $\Delta\Psi_m$ resulting from the present invention is detectable with a mitochondria-selective potentiometric probe (e.g., $DiOC_6$). In further embodiments, it is contemplated that a collapse of a cell's mitochondrial $\Delta\Psi_m$ resulting from the present invention occurs after an initial increase in cellular $O_2^-$ levels.

In some embodiments, it is contemplated that the present invention enables caspace activation. In other embodiments, it is contemplated that the present invention causes the release of cytochrome c from mitochondria. In further embodiments, it is contemplated that the present invention alters cystolic cytochrome c levels. In still other embodiments, it is contemplated that altered cystolic cytochrome c levels resulting from the present invention are detectable by immunoblotting cytosolic fractions. In some embodiments, it is contemplated that diminished cystolic cytochrome c levels resulting from the present invention are detectable after a period of time (e.g., 10 hours). In further preferred embodiments, it is contemplated that diminished cystolic cytochrome c levels resulting from the present invention are detectable after 5 hours.

In other embodiments, it is contemplated that the present invention causes the opening of the mitochondrial PT pore. In some embodiments, it is contemplated that the cellular release of cytochrome c resulting from the present invention is consistent with a collapse of mitochondrial $\Delta\Psi_m$. In still further preferred embodiments, it is contemplated that the present invention causes an increase in cellular $O_2^-$ levels after a mitochondrial $\Delta\Psi_m$ collapse and a release of cytochrome c. In further preferred embodiments, it is contemplated that a rise in cellular $O_2^-$ levels is caused by a mitochondrial $\Delta\Psi_m$ collapse and release of cytochrome c resulting from the present invention.

In other embodiments, it is contemplated that the present invention causes cellular caspase activation. In some embodiments, it is contemplated that caspase activation resulting from the present invention is measurable with a pan-caspase sensitive fluorescent substrate (e.g., FAM-VAD-fmk). In still further embodiments, it is contemplated that caspase activation resulting from the present invention tracks with a collapse of mitochondrial $\Delta\Psi_m$. In other embodiments, it is contemplated that the present invention causes an appearance of hypodiploid DNA. In some embodiments, it is contemplated that an appearance of hypodiploid DNA resulting from the present invention is slightly delayed with respect to caspase activation.

In some embodiments, it is contemplated that the molecular target for the present invention is found within mitochondria. In further embodiments, it is contemplated that the molecular target of the present invention involves the mitochondrial ATPase. The primary sources of cellular ROS include redox enzymes and the mitochondrial respiratory chain (hereinafter MRC). In some embodiments, it is contemplated that cytochrome c oxidase (complex IV of the MRC) inhibitors (e.g., $NaN_3$) preclude a present invention dependent increase in cellular ROS levels. In other preferred embodiments, it is contemplated that the ubiquinol-cytochrome c reductase component of MRC complex III inhibitors (e.g., FK506) preclude a present invention dependent increase in ROS levels.

In some embodiments, it is contemplated that an increase in cellular ROS levels result from the binding of the compounds of the present invention to a target within mitochondria. In some embodiments, it is contemplated that the compounds of the present invention oxidize 2',7'-dichlorodihydrofluorescin (hereinafter DCF) diacetate to DCF. DCF is a redox-active species capable of generating ROS. In further embodiments, it is contemplated that the rate of DCF production resulting from the present invention increases after a lag period.

Antimycin A generates $O_2^-$ by inhibiting ubiquinol-cytochrome c reductase. In some embodiments, it is contemplated that the present invention increases the rate of ROS production in an equivalent manner to antimycin A. In further embodiments, it is contemplated that the present invention increases the rate of ROS production in an equivalent manner to antimycin A under aerobic conditions supporting state 3 respiration. In further embodiments, it is contemplated that the compounds of the present invention do not directly target the MPT pore. In additional embodiments, it is contemplated that the compounds of the present invention do not generate substantial ROS in the subcellular S15 fraction (e.g., cytosol; microsomes). In even further embodiments, it is contemplated that the compounds of the present invention do not stimulate ROS if mitochondria are in state 4 respiration.

MRC complexes I-III are the primary sources of ROS within mitochondria. In some embodiments, it is contemplated that the primary source of an increase in cellular ROS levels resulting from the dependent invention emanates from these complexes as a result of inhibiting the mitochondrial $F_1F_0$-ATPase. Indeed, in still further embodiments, it is contemplated that the present invention inhibits mitochondrial ATPase activity of bovine sub-mitochondrial particles (hereinafter SMPs). In particularly preferred embodiments, it is contemplated that the compounds of the present invention bind to the OSCP component of the mitochondrial $F_1F_0$-ATPase.

Oligomycin is a macrolide natural product that binds to the mitochondrial $F_1F_0$-ATPase, induces a state 3 to 4 transition, and as a result, generates ROS (e.g., $O_2^-$). In some embodiments, the compounds of the present invention bind the OSCP component of the mitochondrial $F_1F_0$-ATPase. In some embodiments, the compounds of the present invention bind the junction between the OSCP and the $F_1$ subunit of the mitochondrial $F_1F_0$-ATPase. In some embodiments, the compounds of the present invention bind the $F_1$ subunit. In certain embodiments, screening assays of the present invention permit detection of binding partners of the OSCP, $F_1$, or OSCP/$F_1$ junction. OSCP is an intrinsically fluorescent protein. In certain embodiments, titrating a solution of test compounds of the present invention into an E. Coli sample overexpressing OSCP results in quenching of the intrinsic OSCP fluorescence. In other embodiments, fluorescent or radioactive test compounds can be used in direct binding assays. In other embodiments, competition binding experiments can be conducted. In this type of assay, test compounds are assessed for their ability to compete with Bz-423 for binding to, for example, the OSCP. In some embodiments, the compounds of the present invention cause a reduced increase in cellular ROS levels and reduced apoptosis in cells through regulation of the OSCP gene (e.g., altering expression of the OSCP gene). In further embodiments, the present invention functions by altering the molecular motions of the ATPase motor.

II. Modulators of Cellular Proliferation and Cell Growth

In some embodiments, it is contemplated that the compounds and methods of the present invention cause decreased cellular proliferation. In other embodiments, it is contemplated that the compounds and methods of the present invention cause decreased cellular proliferation and apoptosis.

III. Exemplary Compounds

Exemplary compounds of the present invention are provided below.

In certain embodiments, the present invention provides compounds described by the following formulas:

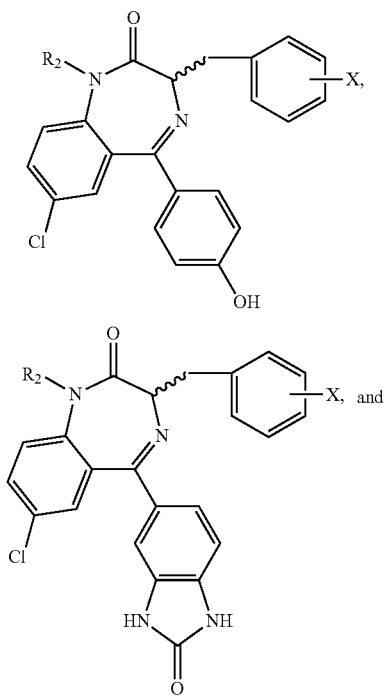

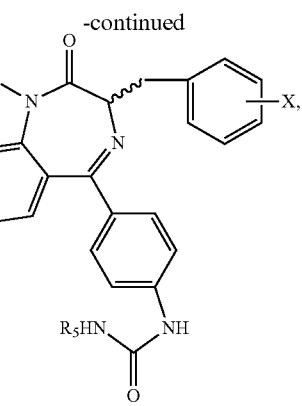

including salts, esters, and prodrugs thereof; and
including both R and S enantiomeric forms and racemic mixtures thereof;
wherein
X is halogen (e.g., Br, Cl, F), alkyl (e.g., methyl, ethyl, propyl (e.g., isopropyl), butyl (e.g., isobutyl, sec-butyl, tert-butyl), pentyl, isoamyl, neopentyl, 1-ethylpropyl, 3-methylpentyl, 2,2-dimethylbutyl, heptyl, hexyl, octyl, 3-ethylbutyl, cyclopropyl, cyclobutyl, cyclopentyl, cyclohexyl), or substituted alkyl;
$R_2$ is hydrogen or a linear or branched alkyl (e.g., methyl, ethyl, propyl (e.g., isopropyl), butyl (e.g., isobutyl, sec-butyl, tert-butyl), pentyl, isoamyl, neopentyl, 1-ethylpropyl, 3-methylpentyl, 2,2-dimethylbutyl, heptyl, hexyl, octyl, 3-ethylbutyl, cyclopropyl, cyclobutyl, cyclopentyl, cyclohexyl); and
$R_5$ is alkyl (e.g., methyl, ethyl, propyl (e.g., isopropyl), butyl (e.g., isobutyl, sec-butyl, tert-butyl), pentyl, isoamyl, neopentyl, 1-ethylpropyl, 3-methylpentyl, 2,2-dimethylbutyl, heptyl, hexyl, octyl, 3-ethylbutyl, cyclopropyl, cyclobutyl, cyclopentyl, cyclohexyl) or substituted alkyl.

In certain embodiments, $R_5$ is alkyl substituted by one or more of halogen, alkoxy, $-NH_2$, $-N(H)(C_1-C_4$ alkyl$)$, or $-N(C_1-C_4$ alkyl$)_2$. In certain embodiments, $R_5$ is $-(CH_2)_nN(R_6)_2$, $-(CH_2)_nCF_3$, or $-(CH_2)_nO(R_6)_2$, wherein n is 1, 2, 3, or 4.

In certain embodiments, the compounds are as described in the following tables.

TABLE 1

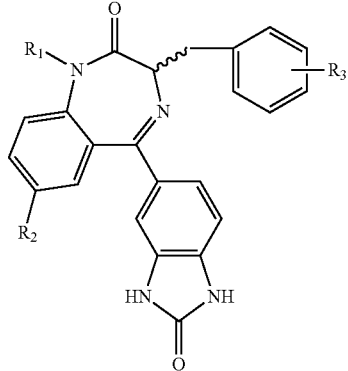

| Compound No. | $R_1$ | $R_2$ | $R_3$ |
|---|---|---|---|
| 1 | H | halogen | halogen or alkyl |
| 2 | alkyl | halogen | halogen or alkyl |

TABLE 1-continued

| Compound No. | $R_1$ | $R_2$ | $R_3$ |
|---|---|---|---|
| 3 | H | Cl | Cl |
| 4 | H | Cl | Br |
| 5 | H | Cl | F |
| 6 | H | Cl | alkyl |
| 7 | H | Cl | —CH$_3$ |
| 8 | H | Cl | —CH$_2$CH$_3$ |
| 9 | H | Cl | —(CH$_2$)$_2$CH$_3$ |
| 10 | H | Cl | —CH(CH$_3$)$_2$ |
| 11 | H | Cl | —(CH$_2$)$_3$CH$_3$ |
| 12 | H | Cl | —CH$_2$CH(CH$_3$)$_2$ |
| 13 | H | Cl | —C(CH$_3$)$_3$ |
| 14 | H | Cl | fluoroalkyl |
| 15 | H | Cl | —CF$_3$ |
| 16 | —CH$_3$ | Cl | Cl |
| 17 | —CH$_3$ | Cl | Br |
| 18 | —CH$_3$ | Cl | F |
| 19 | —CH$_3$ | Cl | alkyl |
| 20 | —CH$_3$ | Cl | —CH$_3$ |
| 21 | —CH$_3$ | Cl | —CH$_2$CH$_3$ |
| 22 | —CH$_3$ | Cl | —(CH$_2$)$_2$CH$_3$ |
| 23 | —CH$_3$ | Cl | —CH(CH$_3$)$_2$ |
| 24 | —CH$_3$ | Cl | —(CH$_2$)$_3$CH$_3$ |
| 25 | —CH$_3$ | Cl | —CH$_2$CH(CH$_3$)$_2$ |
| 26 | —CH$_3$ | Cl | —C(CH$_3$)$_3$ |
| 27 | —CH$_3$ | Cl | fluoroalkyl |
| 28 | —CH$_3$ | Cl | —CF$_3$ |

TABLE 2

| Compound No. | $R_1$ | $R_2$ | $R_3$ | $R_4$ |
|---|---|---|---|---|
| 1 | H | halogen | OH | halogen or alkyl |
| 2 | alkyl | halogen | OH | halogen or alkyl |
| 3 | H | halogen | alkoxy | halogen or alkyl |
| 4 | alkyl | halogen | alkoxy | halogen or alkyl |
| 5 | H | Cl | OH | Cl |
| 6 | H | Cl | OH | Br |
| 7 | H | Cl | OH | F |
| 8 | H | Cl | OH | alkyl |
| 9 | H | Cl | OH | —CH$_3$ |
| 10 | H | Cl | OH | —CH$_2$CH$_3$ |
| 11 | H | Cl | OH | —(CH$_2$)$_2$CH$_3$ |
| 12 | H | Cl | OH | —CH(CH$_3$)$_2$ |
| 13 | H | Cl | OH | —(CH$_2$)$_3$CH$_3$ |
| 14 | H | Cl | OH | —CH$_2$CH(CH$_3$)$_2$ |
| 15 | H | Cl | OH | —C(CH$_3$)$_3$ |
| 16 | H | Cl | OH | fluoroalkyl |
| 17 | H | Cl | OH | —CF$_3$ |
| 18 | —CH$_3$ | Cl | OH | Cl |
| 19 | —CH$_3$ | Cl | OH | Br |
| 20 | —CH$_3$ | Cl | OH | F |
| 21 | —CH$_3$ | Cl | OH | alkyl |
| 22 | —CH$_3$ | Cl | OH | —CH$_3$ |
| 23 | —CH$_3$ | Cl | OH | —CH$_2$CH$_3$ |
| 24 | —CH$_3$ | Cl | OH | —(CH$_2$)$_2$CH$_3$ |
| 25 | —CH$_3$ | Cl | OH | —CH(CH$_3$)$_2$ |
| 26 | —CH$_3$ | Cl | OH | —(CH$_2$)$_3$CH$_3$ |
| 27 | —CH$_3$ | Cl | OH | —CH$_2$CH(CH$_3$)$_2$ |
| 28 | —CH$_3$ | Cl | OH | —C(CH$_3$)$_3$ |
| 29 | —CH$_3$ | Cl | OH | fluoroalkyl |
| 30 | —CH$_3$ | Cl | OH | —CF$_3$ |

TABLE 3

| Compound No. | $R_1$ | $R_2$ | $R_3$ | $R_4$ |
|---|---|---|---|---|
| 1 | H | halogen | —N(H)C(O)N(H)alkyl | halogen or alkyl |
| 2 | alkyl | halogen | —N(H)C(O)N(H)alkyl | halogen or alkyl |
| 3 | H | halogen | —N(H)C(O)N(H)CH$_3$ | halogen |
| 4 | H | halogen | —N(H)C(O)N(H)CH$_2$CH$_3$ | halogen |
| 5 | H | halogen | —N(H)C(O)N(H)(CH$_2$)$_2$CH$_3$ | halogen |
| 6 | H | halogen | —N(H)C(O)N(H)CH(CH$_3$)$_2$ | halogen |

TABLE 3-continued

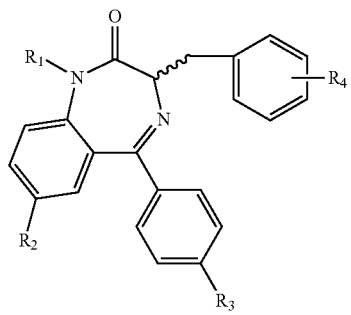

| Compound No. | R₁ | R₂ | R₃ | R₄ |
|---|---|---|---|---|
| 7 | H | halogen | —N(H)C(O)N(H)(CH₂)₃CH₃ | halogen |
| 8 | H | halogen | —N(H)C(O)N(H)CH₂CH(CH₃)₂ | halogen |
| 9 | H | halogen | —N(H)C(O)N(H)C(CH₃)₃ | halogen |
| 10 | alkyl | halogen | —N(H)C(O)N(H)CH₃ | halogen |
| 11 | alkyl | halogen | —N(H)C(O)N(H)CH₂CH₃ | halogen |
| 12 | alkyl | halogen | —N(H)C(O)N(H)(CH₂)₂CH₃ | halogen |
| 13 | alkyl | halogen | —N(H)C(O)N(H)CH(CH₃)₂ | halogen |
| 14 | alkyl | halogen | —N(H)C(O)N(H)(CH₂)₃CH₃ | halogen |
| 15 | alkyl | halogen | —N(H)C(O)N(H)CH₂CH(CH₃)₂ | halogen |
| 16 | alkyl | halogen | —N(H)C(O)N(H)C(CH₃)₃ | halogen |
| 17 | H | halogen | —N(H)C(O)N(H)CH₃ | alkyl |
| 18 | H | halogen | —N(H)C(O)N(H)CH₂CH₃ | alkyl |
| 19 | H | halogen | —N(H)C(O)N(H)(CH₂)₂CH₃ | alkyl |
| 20 | H | halogen | —N(H)C(O)N(H)CH(CH₃)₂ | alkyl |
| 21 | H | halogen | —N(H)C(O)N(H)(CH₂)₃CH₃ | alkyl |
| 22 | H | halogen | —N(H)C(O)N(H)CH₂CH(CH₃)₂ | alkyl |
| 23 | H | halogen | —N(H)C(O)N(H)C(CH₃)₃ | alkyl |
| 24 | alkyl | halogen | —N(H)C(O)N(H)CH₃ | alkyl |
| 25 | alkyl | halogen | —N(H)C(O)N(H)CH₂CH₃ | alkyl |
| 26 | alkyl | halogen | —N(H)C(O)N(H)(CH₂)₂CH₃ | alkyl |
| 27 | alkyl | halogen | —N(H)C(O)N(H)CH(CH₃)₂ | alkyl |
| 28 | alkyl | halogen | —N(H)C(O)N(H)(CH₂)₃CH₃ | alkyl |
| 29 | alkyl | halogen | —N(H)C(O)N(H)CH₂CH(CH₃)₂ | alkyl |
| 30 | alkyl | halogen | —N(H)C(O)N(H)C(CH₃)₃ | alkyl |
| 31 | H | Cl | —N(H)C(O)N(H)alkyl | Cl |
| 32 | H | Cl | —N(H)C(O)N(H)alkyl | Br |
| 33 | H | Cl | —N(H)C(O)N(H)alkyl | F |
| 34 | H | Cl | —N(H)C(O)N(H)alkyl | alkyl |
| 35 | H | Cl | —N(H)C(O)N(H)alkyl | —CH₃ |
| 36 | H | Cl | —N(H)C(O)N(H)alkyl | —CH₂CH₃ |
| 37 | H | Cl | —N(H)C(O)N(H)alkyl | —(CH₂)₂CH₃ |
| 38 | H | Cl | —N(H)C(O)N(H)alkyl | —CH(CH₃)₂ |
| 39 | H | Cl | —N(H)C(O)N(H)alkyl | —(CH₂)₃CH₃ |
| 40 | H | Cl | —N(H)C(O)N(H)alkyl | —CH₂CH(CH₃)₂ |
| 41 | H | Cl | —N(H)C(O)N(H)alkyl | —C(CH₃)₃ |
| 42 | H | Cl | —N(H)C(O)N(H)alkyl | fluoroalkyl |
| 43 | H | Cl | —N(H)C(O)N(H)alkyl | —CF₃ |
| 44 | —CH₃ | Cl | —N(H)C(O)N(H)alkyl | Cl |
| 45 | —CH₃ | Cl | —N(H)C(O)N(H)alkyl | Br |
| 46 | —CH₃ | Cl | —N(H)C(O)N(H)alkyl | F |
| 47 | —CH₃ | Cl | —N(H)C(O)N(H)alkyl | alkyl |
| 48 | —CH₃ | Cl | —N(H)C(O)N(H)alkyl | —CH₃ |
| 49 | —CH₃ | Cl | —N(H)C(O)N(H)alkyl | —CH₂CH₃ |
| 50 | —CH₃ | Cl | —N(H)C(O)N(H)alkyl | —(CH₂)₂CH₃ |
| 51 | —CH₃ | Cl | —N(H)C(O)N(H)alkyl | —CH(CH₃)₂ |
| 52 | —CH₃ | Cl | —N(H)C(O)N(H)alkyl | —(CH₂)₃CH₃ |
| 53 | —CH₃ | Cl | —N(H)C(O)N(H)alkyl | —CH₂CH(CH₃)₂ |
| 54 | —CH₃ | Cl | —N(H)C(O)N(H)alkyl | —C(CH₃)₃ |
| 55 | —CH₃ | Cl | —N(H)C(O)N(H)alkyl | fluoroalkyl |
| 56 | —CH₃ | Cl | —N(H)C(O)N(H)alkyl | —CF₃ |

More specifically, in certain embodiments, the present invention provides the following compounds:
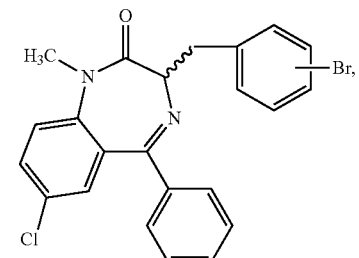
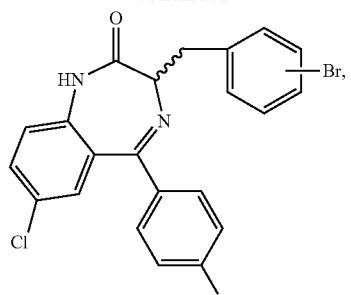
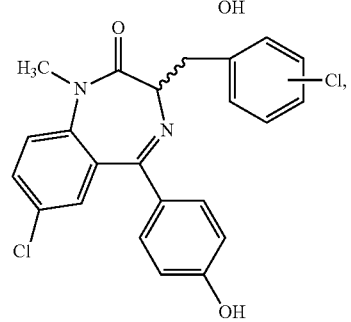
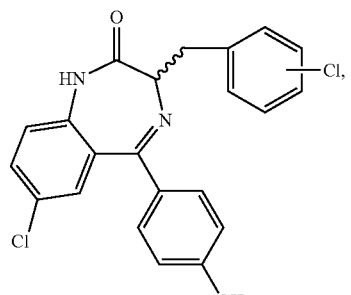
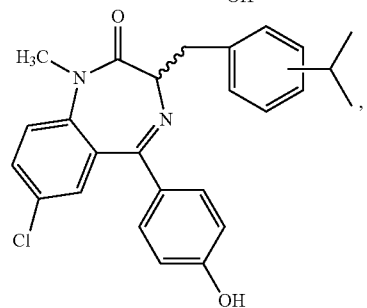
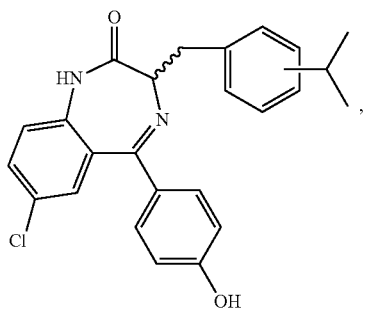
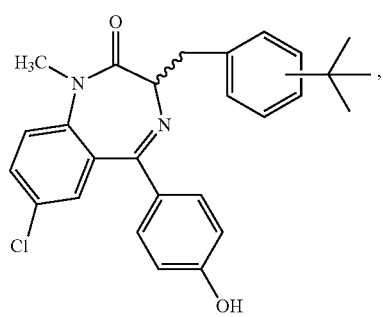
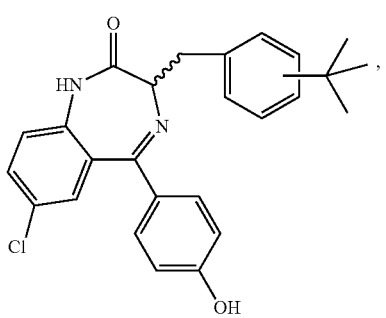
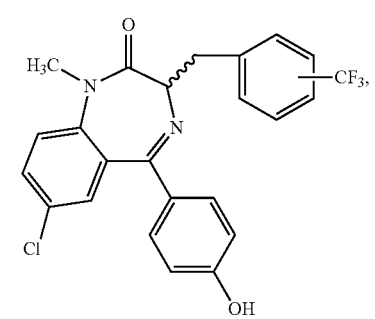
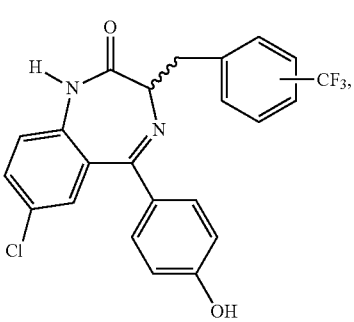

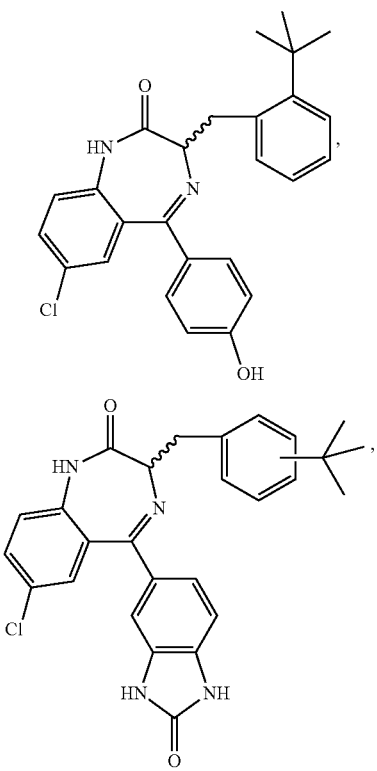
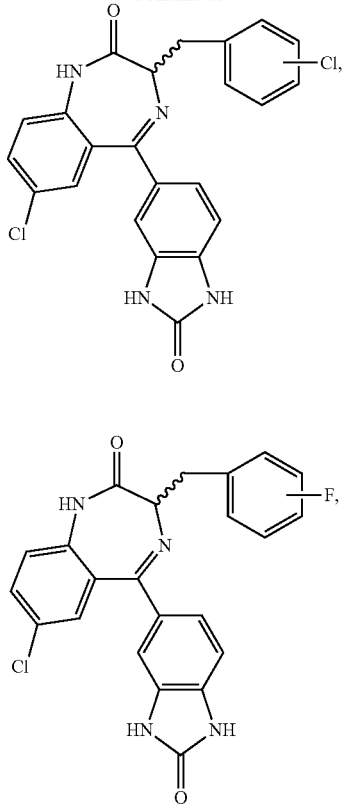
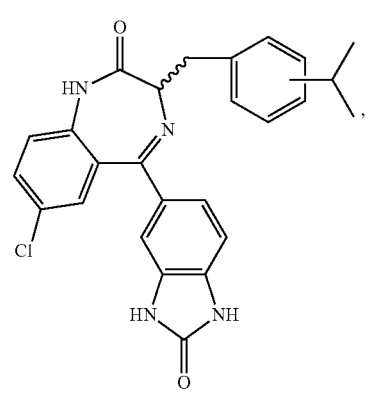
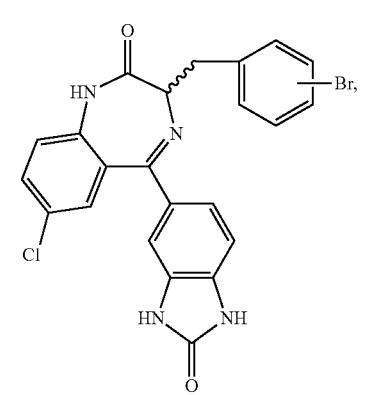

-continued
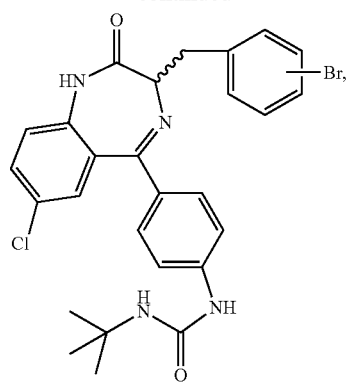
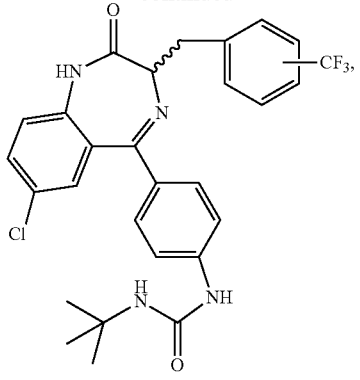

45
-continued
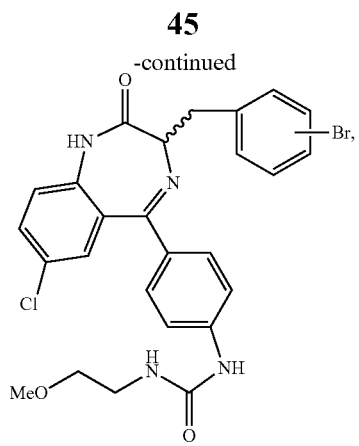
46
-continued
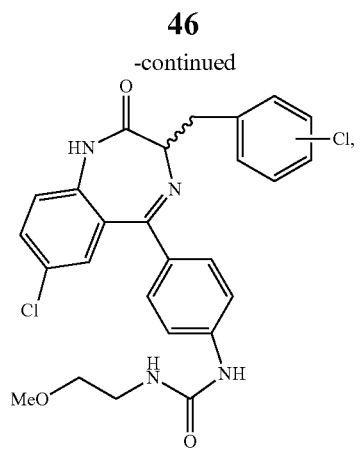
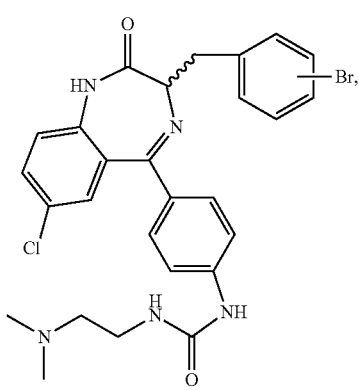
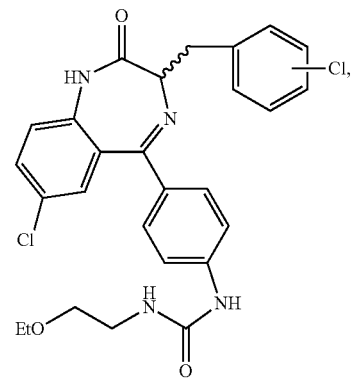
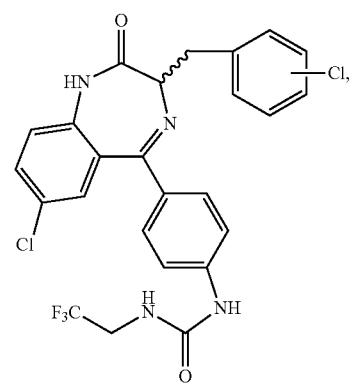
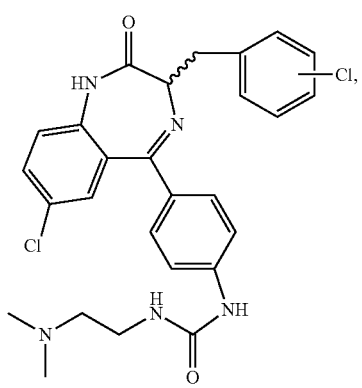
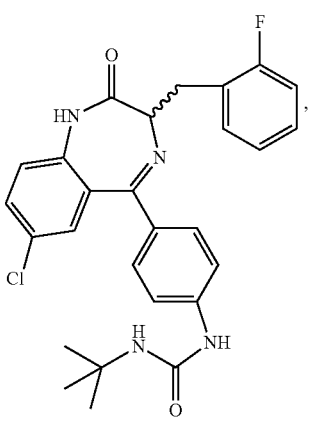

47
-continued
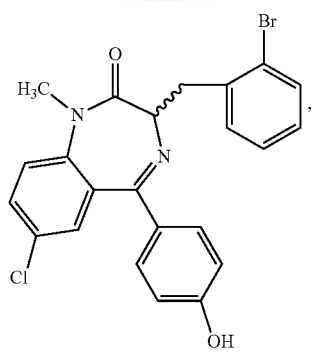
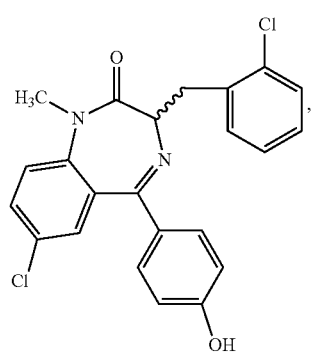
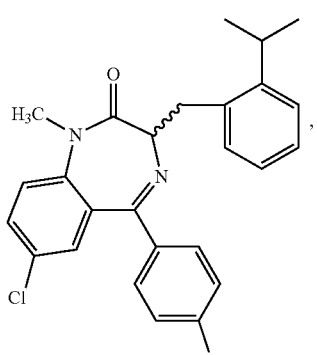
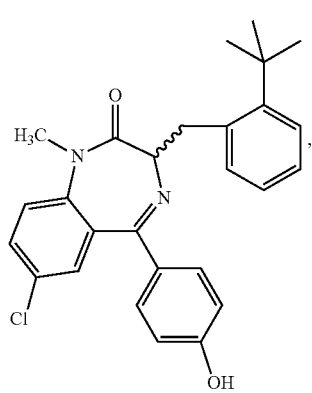
48
-continued
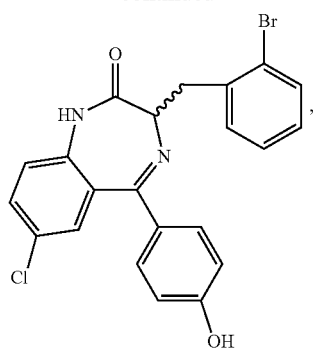
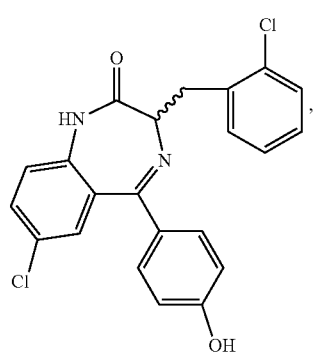
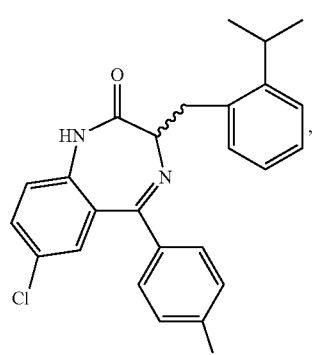
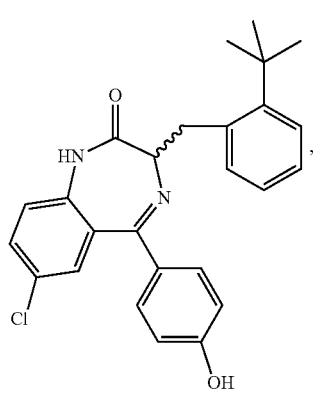

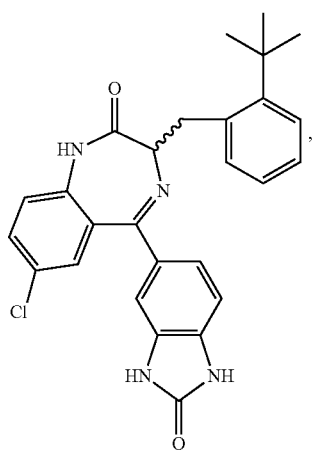
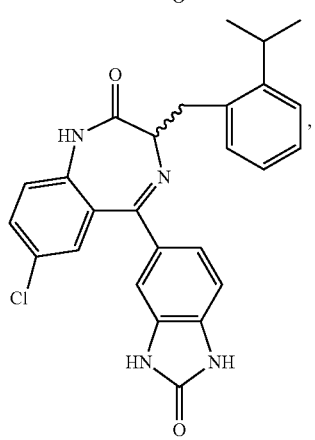
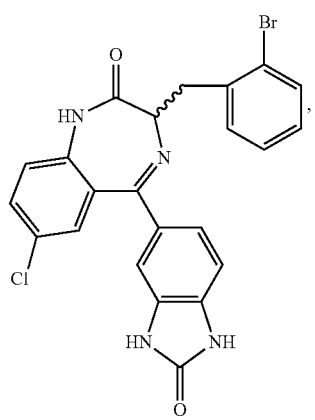
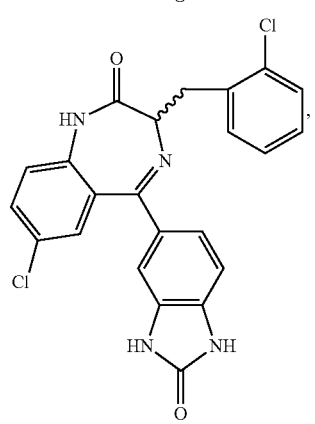
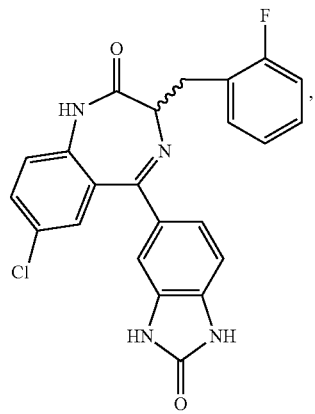
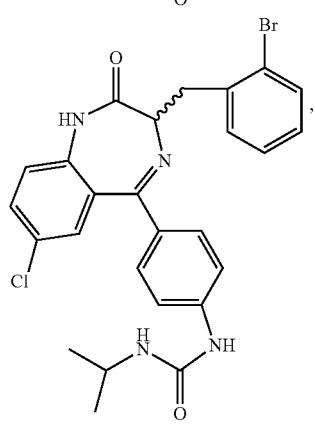
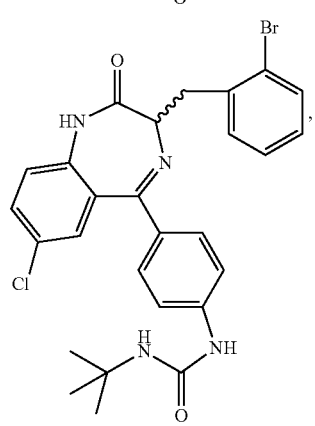
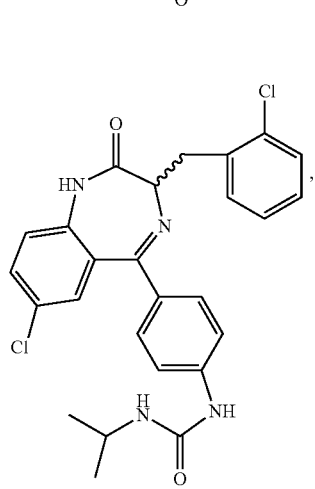

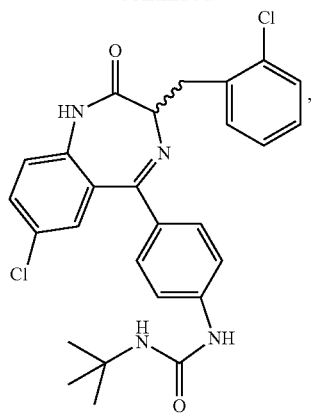
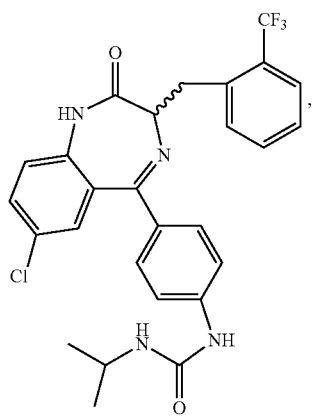
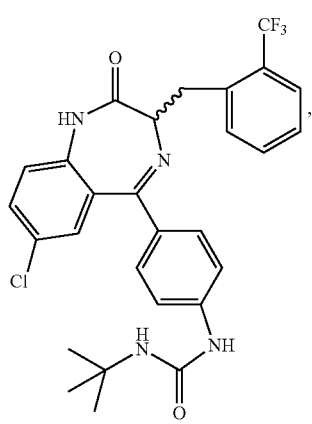
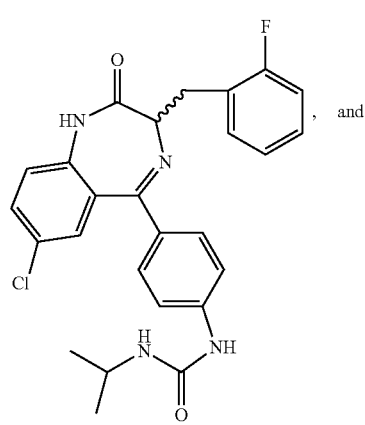
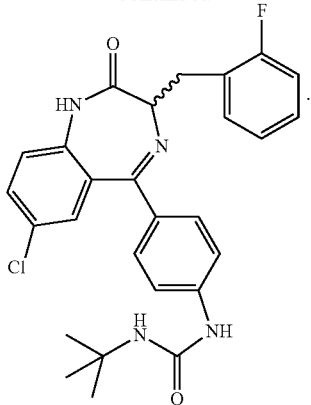
, and

In addition, it is well-known that many benzodiazepines exist as optical isomers due to the chirality introduced into the heterocyclic ring at the $C_3$ position. The optical isomers are sometimes described as L- or D-isomers in the literature. Alternatively, the isomers are also referred to as R- and S-enantiomorphs. For the sake of simplicity, these isomers are referred to as enantiomorphs or enantiomers. The benzodiazepine compounds (and related compounds) described herein include their enantiomeric forms as well as racemic mixtures. Thus, the usage of the term "benzodiazepine or its enantiomers" or similar terms herein refers to the benzodiazepine (and/or related compounds) as described or depicted, including all its enantiomorphs as well as their racemic mixture.

Any one or more of the compounds can be used to treat a variety of dysregulatory disorders related to cellular death as described elsewhere herein. Additionally, any one or more of these compounds can be used to inhibit ATP hydrolysis while not affecting cell synthesis or cell viability. Additionally, any one or more of these compounds can be used in combination with at least one other therapeutic agent (e.g., potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$ and $P2Y_{12}$ antagonists, thromboxane receptor antagonists, and aspirin) in along with a pharmaceutically-acceptable carrier or diluent in a pharmaceutical composition. Additionally, any one or more of these compounds can be used to treat a mitochondrial $F_1F_0$-ATP hydrolase associated disorder (e.g., myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, medication, pregnancy and fetal loss, and diabetic complications comprising retinopathy, nephropathy and neuropathy) in a patient. The above-described compounds can also be used in drug screening assays and other diagnostic and research methods.

In certain embodiments, one or more of the exemplary compounds can be used in combination with a therapeutic agent selected from the group consisting of potassium channel openers, calcium channel blockers, sodium hydrogen exchanger inhibitors, antiarrhythmic agents (e.g., sotalol, dofetilide, amiodarone, azimilide, ibutilide, ditiazem, verapamil), antiatherosclerotic agents, anticoagulants, antithrombotic agents, prothrombolytic agents, fibrinogen antagonists, diuretics, antihypertensive agents (e.g., captopril, lisinopril, zofenopril, ramipril, fosinopril, enalapril, ceranopril, cilazopril, delapril, pentopril, quinapril, omapatrilat, gemopatrilat, losartan, irbesartan, valsartan, sitaxsentan, atrsentan), ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents including, but not limited to, ACE inhibitors, AT-1 receptor antagonists, ET receptor antagonists, dual ET/AII receptor antagonists, and vasopepsidase inhibitors, or an antiplatelet agent (platelet inhibitor) comprising GPIIb/IIIa blockers, P2Y$_1$ and P2Y$_{12}$ antagonists, thromboxane receptor antagonists, abciximab, eptifibatide, tirofiban, clopidogrel, toclopidine, CS-747, ifetroban, and aspirin. In certain instances, the therapeutic agent is propafenone, propranolol; sotalol, dofetilide, amiodarone, azimilide, ibutilide, ditiazem, verapamil, captopril, lisinopril, zofenopril, ramipril, fosinopril, enalapril, eranopril, cilazopril, delapril, pentopril, quinapril, omapatrilat, gemopatrilat, losartan, irbesartan, valsartan, sitaxsentan, atrsentan; verapamil, nifedipine, diltiazem, amlodipine and mybefradil, digitalis, ouabain, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolatone, aplirinone, dipyridamole, cilostazol, sildenafil, ifetroban, picotamide, ketanserin, clopidogrel, picotamide, rosuvastaitin, atavastatin visastatin, questran, CP-529414, lovenox, enoxaparain dalteparinnadolol, carvedilol, albuterol, terbutaline, formoterol, salmeterol, bitolterol, pilbuterol, fenoterol, ipratropium bromide, metformin, acarbose, repaglinide, glimpepiride, glyburide, glyburide, glipizide, glucovance, troglitazone, rosiglitazone, pioglitazone, GLP-1, nefazodone, sertraline, diazepam, lorazepam, buspirone, hydroxyzine pamoate, acarbose, endostatin, probucol, BO-653, Vitamin A, Vitamin E, AGI-1067, alendronate, raloxifene, orlistate, cyclosperine A, paclitaxel, FK506, adriamycin, famotidine, rapitidine, ompeprazole, estrogen, estradiol, dipyridamole, cilostazol, sildenafil, ketanserin, taxol, cisplatin, paclitaxel, adriamycin, epothilones, carboplatin, cromolyn, nedocromil, theophylline, zileuton, zafirlukast, monteleukast, pranleukast, beclomethasone, triamcinolone, budesonide, fluticasone, flunisolidem prednisone; dexamethasone, etanercept, aspirin, indomethacin, pravastatin, simvastatin, atorvastatin, fluvastatin, cerivastatin, AZ4522, itavastatin, ZD-4522, rosuvastatin, atavastatin, visastatin, abciximab, eptifibatide, tirofiban, clopidogrel, ticlopidine, CS-747, ifetroban, aspirin; cariporide, streptokinase, reteplase, activase, lanoteplase, urokinase, prourokinse, tenecteplase, lanoteplase, anistreplase, eminase, lepirudin, argatroban, XR-330, T686, anti-α-2-antiplasmin antibody, or doesdipyridanmol.

Methods for preparing the benzodiazepine compounds described herein are illustrated in the following synthetic schemes. The following schemes are given for the purpose of illustrating the invention, but not for limiting the scope or spirit of the invention.

The benzodiazepine core can be constructed using the synthetic routes illustrated in Schemes 1 and 2. The starting material, 5-chloroisatoic anhydride (A), for these routes is commercially available. The synthetic route illustrated in Scheme 1 begins by installing a protecting group (e.g., p-methoxybenzyl (PMB)) onto the nitrogen atom of the amide, or, alternatively, alkylating the nitrogen atom to install the substituent desired at this location of the benzodiazepine final product. Alkylation of A to provide intermediate B may be carried out by treating A with an inorganic base, such as sodium carbonate or sodium hydride, and an alkyl or benzyl halide. A large number of alkyl halides and benzyl halides are known in the art and contemplated to be amenable to the synthetic route.

The second step illustrated in Scheme 1 involves combining isatoic anhydride B and an an amino acid, such as glycine in an organic solvent such as acetic acid or N,N-dimethylformamide, and heating the mixture to a temperature in the range of about 60-130° C. for about 12-36 hours. Alternatively, the condensation reaction may be performed in two steps. The first step involves combining an amino acid, such as a phenylalanine derivative, and isatoic anhydride B in a solvent such as pyridine or acetonitrile, with or without water, containing triethylamine at a temperature in the range of about 20-100° C. for approximately 12-18 hours followed by removing the solvents in vacuo. The second step involves addition of an organic solvent, such as acetic acid or N,N-dimethylformamide, and heating the mixture to a temperature in the range of about 80-130° C. for about 12-24 hours.

Scheme 1.

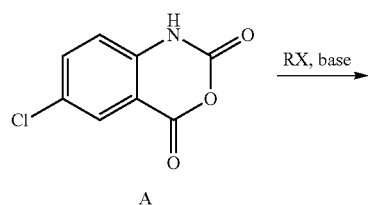
A

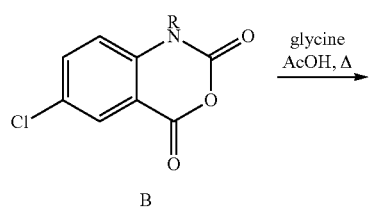
B

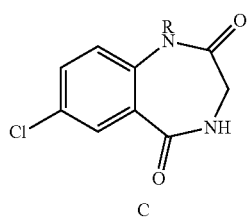
C

R = PMB or alkyl, e.g., Me.
X = halogen.

The synthetic route in Scheme 2 illustrates a one-step process for constructing the benzodiazepine core and installing C3-functionality. The reaction involves combining an amino acid, such as glycine, and an isatoic anhydride, such as A, in an organic solvent such as acetic acid or N,N-dimethylformamide, and heating the mixture to a temperature in the range of about 60-130° C. for about 12-36 hours. Alternatively, the condensation reaction may be performed in two steps. The first step involves combining an amino acid, such as a phenylalanine derivative, and an isatoic anhydride, in a solvent such as pyridine or acetonitrile, with or without water, containing triethylamine at a temperature in the range of about 20-100° C. for approximately 12-18 hours followed by removing the solvents in vacuo. The second step involves adding an organic solvent, such as acetic acid or N,N-dimethylformamide, and heating the mixture to a temperature in the range of about 80-130° C. for about 12-24 hours to provide intermediate H. Notably, a protecting group can be installed at the N1-position by reacting intermediate H will a mild base and p-methoxybenzyl chloride.

Scheme 2.

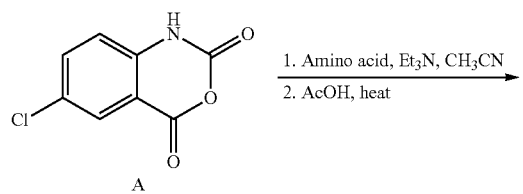
A

1. Amino acid, Et₃N, CH₃CN
2. AcOH, heat

-continued

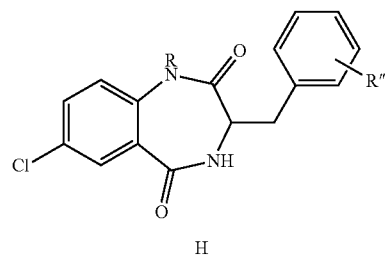
H

R = H  ⎫ Na₂CO₃
R = PMB ⎭ PMB—Cl
R'' = H, halogen, alkyl, etc.

The next phase of the synthesis involves installing the C3 and/or C5 functional groups, as illustrated in Scheme 3. Treatment of compound C with a chlorinating agent, such as phosphoryl chloride in toluene buffered with N,N-dimethylaniline, provides imidoyl chloride D. This reaction is generally performed at elevated temperature (e.g. 90° C.) for several hours (e.g., 4-18 hours). Other chlorinating agents are known in the art and are contemplated to be amenable to the synthetic route.

Compound G can be prepared from compound D using either of the two synthetic strategies shown in Scheme 3. In the first approach, compound D is treated with a strong base, e.g., potassium tert-butoxide, and then a benzyl halide, to provide intermediate F. Imidoyl chloride F may be converted to compound G using Suzuki cross-coupling conditions employing a boronic acid or boronate ester coupling partner in the presence of an appropriate palladium catalyst. A large number of boron-containing reagents for use in Suzuki cross-coupling are known in the art and contemplated to be amenable to the synthetic route. However, boron-containing reagents that are not commercially available may be prepared from the requisite aryl halide (e.g. iodide or bromide) under standard conditions, e.g., by treatment with bis(pinacolato)diboron in hot 1,4-dioxane containing a catalytic amount of a palladium catalyst.

In the second approach, compound D is combined with a boronic acid or boronate ester coupling partner under Suzuki cross-coupling conditions to form intermediate E. This protocol works particularly well with aryl boronic acid esters that do not contain acidic protons in the Ar₁ side chain. Next, intermediate E is alkylated at the C3-position to introduce a C3-aralkyl group. The alkylation step is carried out by treating intermediate E with a strong base, e.g., potassium tert-butoxide, at reduced temperature, e.g., −78° C. to −20° C., followed by addition of a benzyl halide. A large number of benzyl halides are known in the art and contemplated to be amenable to the synthetic route. However, benzyl halides that are not commercially available may be prepared by one of several routes that will be familiar to one skilled in the art of organic synthesis: for example, reduction of a commercially available carboxylic acid (e.g., reduction using lithium aluminum hydride), formylation of an appropriate aromatic compound followed by reduction and conversion of the resulting alcohol to a halide in one step or two steps, such as via a sulfonate ester.

Scheme 3.

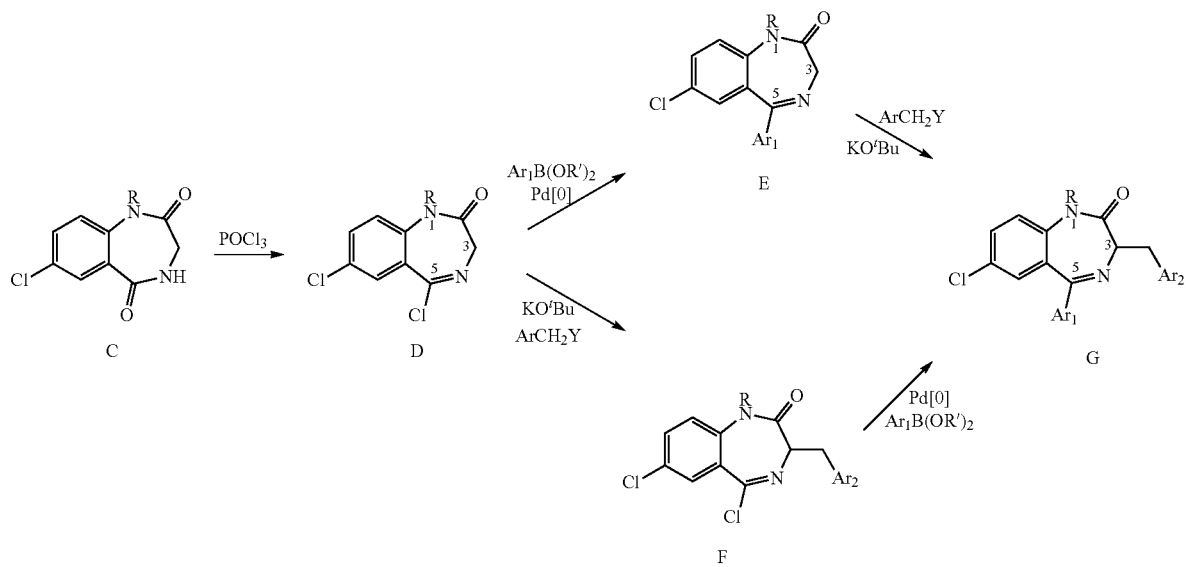

R = PMB or alkyl, e.g., Me.
R' = H or alkyl.
Y is a leaving group, e.g., Br or I.

The breadth of compounds that can be prepared by the procedures described above can be further expanded by modifying the functional groups attached to the C3-aralkyl group of compound G. For example, as illustrated in Scheme 4, it is contemplated that a halogen atom attached to the aralkyl group can be converted to an alkyl group using an alkyl Grignard reagent in the presence of an iron catalyst. Procedures for carrying out reactions of this type are known in the art.

Scheme 4.

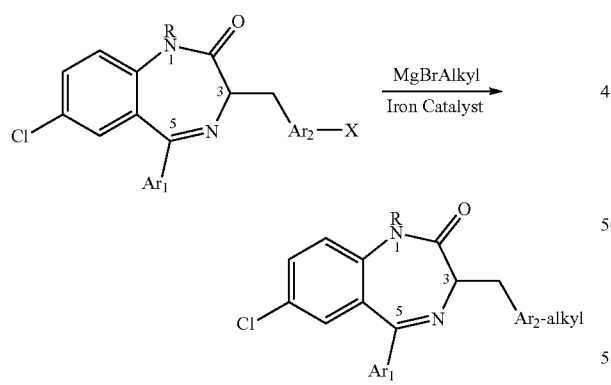

R = alkyl or PMB
X is Br or I

In situations where compound G contains one or more protecting groups, the protecting groups can be removed using standard deprotection procedures known in the art. See, for example, Greene, T. W.; Wuts, P. G. M. *Protective Groups in Organic Synthesis*, 2$^{nd}$ ed.; Wiley: New York, 1991. For instance, removal of a nitrogen protecting group such as a p-methoxybenzyl (PMB) group at the $N_1$-position may be performed using $AlCl_3$ or cerium ammonium nitrate (CAN).

Similarly, demethylation or debenzylation of a phenolic ether in the $Ar_1$-group may be performed using $BBr_3$, EtSH or $AlCl_3$ to provide phenols. Representative deprotection procedures are illustrated in Scheme 5.

Scheme 5.

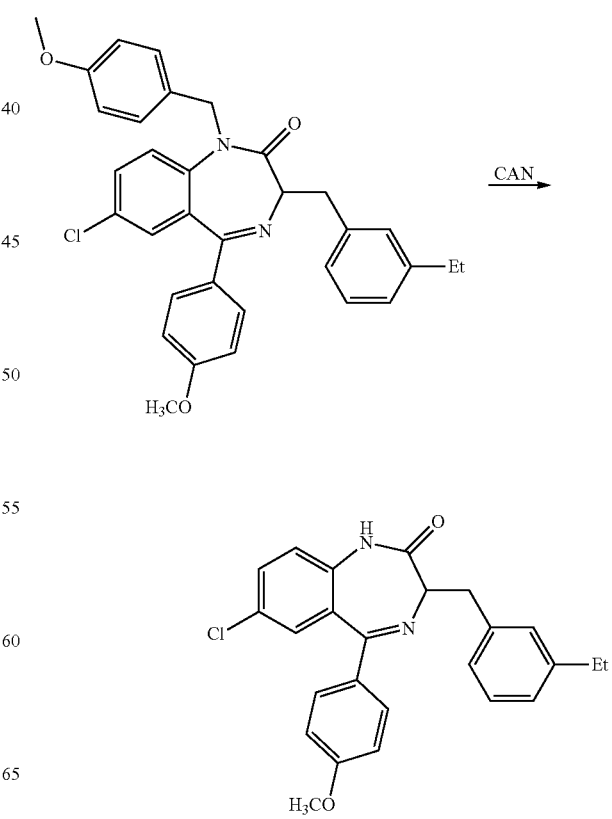

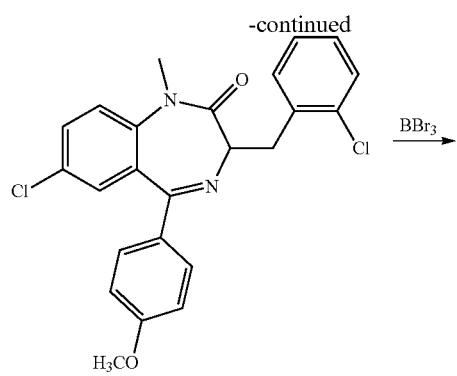

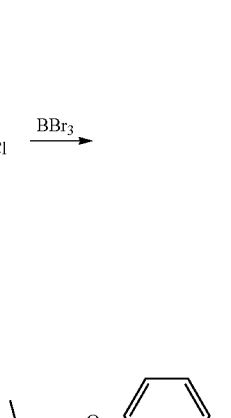

Compounds having an aryl urea in the $Ar_1$ group may be prepared by the routes illustrated in Schemes 6 and 7. The synthesis in both schemes begins using compound D, which may be prepared as described above. In Scheme 6, imidoyl chloride D is by treated with a strong base, e.g., potassium tert-butoxide, at reduced temperature, e.g., −78° C. to −20° C., followed by addition of a benzyl halide. Then, intermediate F is treated with an aryl boronate ester or boronic acid under Suzuki cross-coupling conditions to provide intermediate J. In situations where the R group is a protecting group (e.g., when preparing $N_1$—H compounds), the protecting group is removed, thereby providing compound K. Finally, the boc protecting group is removed and the p-aminophenyl group is converted to a p-ureaphenyl group by reaction with triphosgene and an alkyl amine. Also, as indicated in Scheme 6, the urea group can be installed on the aryl boronate ester or boronic acid used in the Suzuki coupling step, thereby providing a more direct route from imidoyl chloride F to final product L. These approaches provide for convenient diversification of the $R_5$ group late in the synthesis.

Scheme 6.

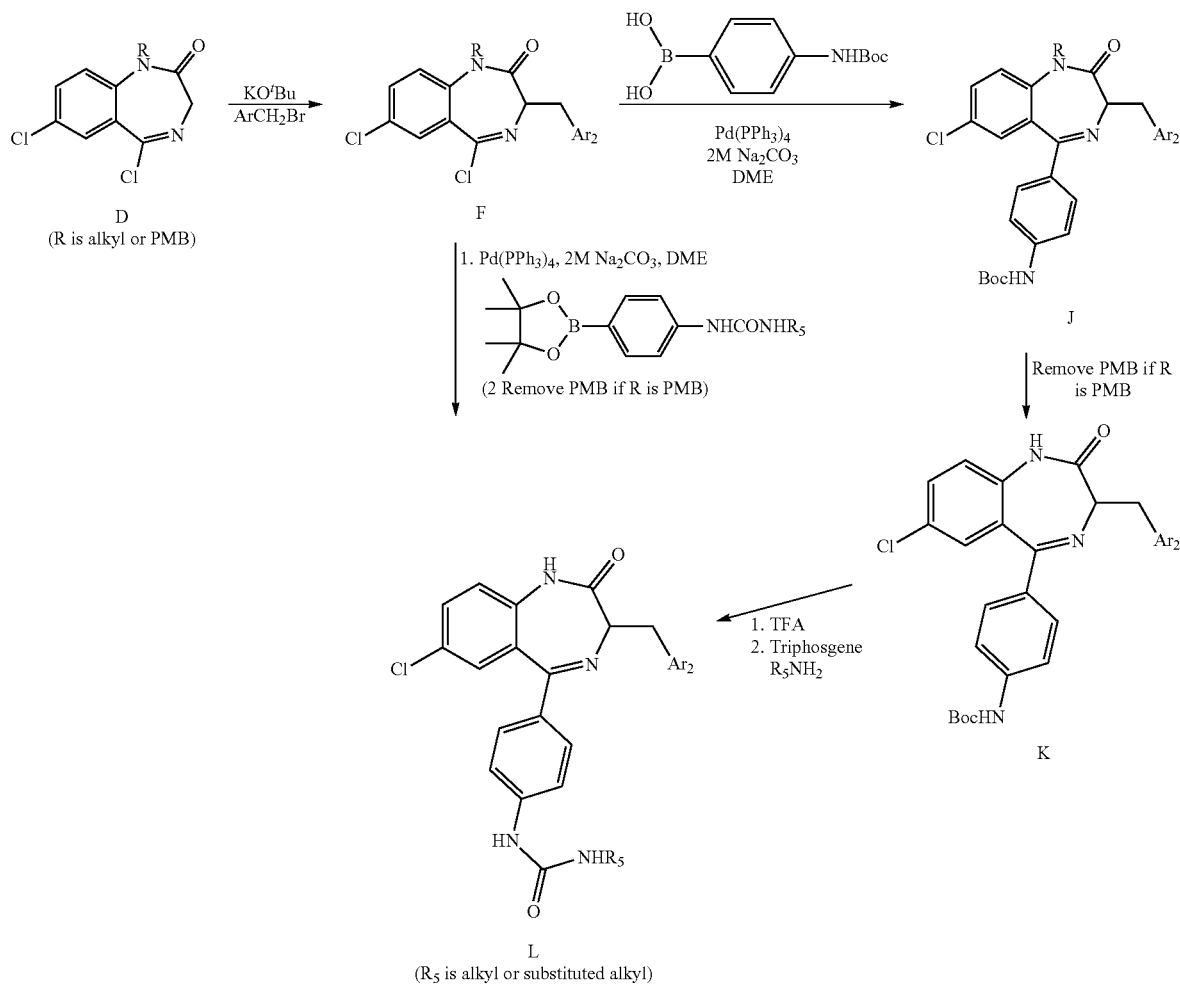

In Scheme 7, which presents an alternative strategy for preparing intermediate J, imidoyl chloride D is treated with an aryl boronate ester or boronic acid under Suzuki cross-coupling conditions to provide intermediate I. Then, intermediate I is treated with a strong base, e.g., potassium tert-butoxide, at reduced temperature, e.g., −78° C. to −20° C., followed by addition of a benzyl halide to provide compound J.

Benzodiazepine compounds having a C5-benzo[d]imidazolyl group can be prepared using palladium coupling conditions, as illustrated in Scheme 8. In situations where the R group is a protecting group, compound M can be treated with a deprotecting agent. For example, when R is PMB, compound M can be treated with AlCl₃ to provide the corresponding amide.

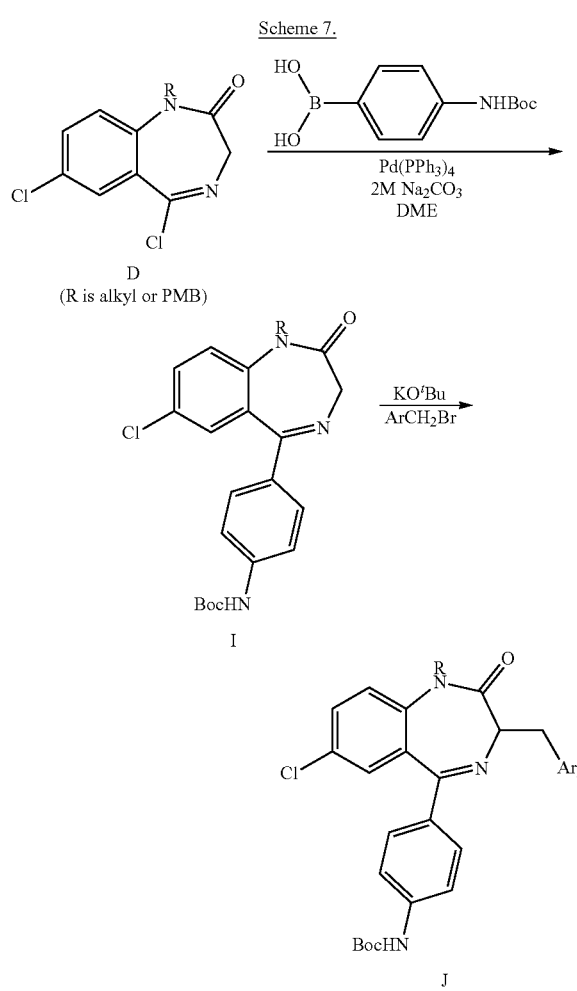

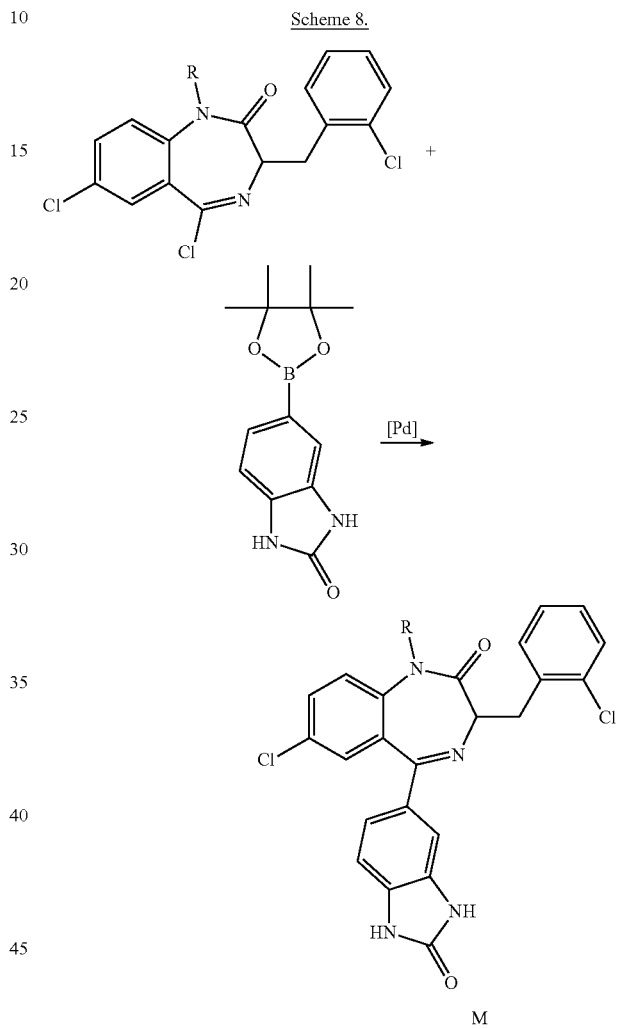

A large number of benzyl halides are known in the art and contemplated to be amenable to the synthetic route. However, benzyl halides that are not commercially available may be prepared by one of several routes that will be familiar to one skilled in the art of organic synthesis: for example, reduction of a commercially available carboxylic acid (e.g., reduction using lithium aluminum hydride), formylation of an appropriate aromatic compound followed by reduction and conversion of the resulting alcohol to a halide in one step or two steps, such as via a sulfonate ester. Similarly, a large number of boron-containing reagents for use in Suzuki cross-coupling are known in the art and contemplated to be amenable to the synthetic route. However, boron-containing reagents that are not commercially available may be prepared from the requisite aryl halide (e.g. iodide or bromide) under standard conditions, e.g., by treatment with bis(pinacolato)diboron in hot 1,4-dioxane containing a catalytic amount of a palladium catalyst.

IV. Pharmaceutical Compositions, Formulations, and Exemplary Administration Routes and Dosing Considerations Exemplary embodiments of various contemplated medicaments and pharmaceutical compositions are provided below.

A. Preparing Medicaments

It is contemplated that the compounds of the present invention are useful in the preparation of medicaments to treat a variety of conditions associated with dysregulation of cell death, aberrant cell growth and hyperproliferation.

In addition, it is contemplated that the compounds are also useful for preparing medicaments for treating other disorders wherein the effectiveness of the compounds are known or predicted. Such disorders include, but are not limited to, neurological (e.g., epilepsy) or neuromuscular disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises an lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, the compounds of the present invention are provided in unsolvated form or are in non-aqueous solutions (e.g., ethanol). The compounds may be generated to allow such formulations through the production of specific crystalline polymorphs compatible with the formulations.

In certain embodiments, the present invention provides instructions for administering said compound to a subject. In certain embodiments, the present invention provides instructions for using the compositions contained in a kit for the treatment of conditions characterized by the dysregulation of apoptotic processes in a cell or tissue (e.g., providing dosing, route of administration, decision trees for treating physicians for correlating patient-specific characteristics with therapeutic courses of action). In certain embodiments, the present invention provides instructions for using the compositions contained in the kit to treat immune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes virus, papilloma virus, HIV), and other conditions such as osteoarthritis and atherosclerosis, and the like.

C. Exemplary Administration Routes and Dosing Considerations

Various delivery systems are known and can be used to administer therapeutic agents (e.g., exemplary compounds as described in Section III above) of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent. One example of an animal model is MLR/MpJ-lpr/lpr ("MLR-lpr") (available from Jackson Laboratories, Bar Harbor, Me.). MLR-lpr mice develop systemic autoimmune disease. Alternatively, other animal models can be developed by inducing tumor growth, for example, by subcutaneously inoculating nude mice with about $10^5$ to about $10^9$ hyperproliferative, cancer or target cells as defined herein. When the tumor is established, the compounds described herein are administered, for example, by subcutaneous injection around the tumor. Tumor measurements to determine reduction of tumor size are made in two dimensions using venier calipers twice a week. Other animal models may also be employed as appropriate. Such animal models for the above-described diseases and conditions are well-known in the art.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is cancer, the additional agent can be a chemotherapeutic agent or radiation. When the condition being treated is an immune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, and can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. It is contemplated that drug resistance, where increasing dosages are required to achieve therapeutic benefit, is overcome by co-administering the compounds described herein with the known agent. It is contemplated that the compounds described herein sensitize target cells to known agents (and vice versa) and, accordingly, less of these agents are needed to achieve a therapeutic benefit.

It is contemplated that the sensitizing function of the claimed compounds also address the problems associated with toxic effects of known therapeutics. In instances where the known agent is toxic, it is desirable to limit the dosages administered in all cases, and particularly in those cases were drug resistance has increased the requisite dosage. It is contemplated that when the claimed compounds are co-administered with the known agent, they reduce the dosage required which, in turn, reduces the deleterious effects. Further, because the claimed compounds are contemplated to be both effective and non-toxic in large doses, co-administration of proportionally more of these compounds than known toxic therapeutics will achieve the desired effects while minimizing toxic effects.

V. Drug Screens

In some embodiments of the present invention, the compounds of the present invention, and other potentially useful compounds, are screened for their binding affinity to the oligomycin sensitivity conferring protein (OSCP) portion of the mitochondrial ATP synthase complex. In particularly preferred embodiments, compounds are selected for use in the methods of the present invention by measuring their binding affinity to recombinant OSCP protein. A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems. While in some embodiments quantifying the intracellular level of ATP following administration of the compounds of the present invention provides an indication of the efficacy of the methods, preferred embodiments of the present invention do not require intracellular ATP or pH level quantification.

Additional embodiments are directed to measuring levels (e.g., intracellular) of superoxide in cells and/or tissues to measure the effectiveness of particular contemplated methods and compounds of the present invention. In this regard, those skilled in the art will appreciate and be able to provide a number of assays and methods useful for measuring superoxide levels in cells and/or tissues.

In some embodiments, structure-based virtual screening methodologies are contemplated for predicting the binding affinity of compounds of the present invention with OSCP. In some embodiments, compound structures are predicted from a molecular modeling software (e.g., MacroModel).

Any suitable assay that allows for a measurement of the rate of binding or the affinity of an exemplary compound of the present invention to the OSCP may be utilized. Examples include, but are not limited to, competition binding using an exemplary compound, surface plasma resonance (SPR) and radio-immunoprecipitation assays (Lowman et al., J. Biol. Chem. 266:10982 [1991]). Surface Plasmon Resonance techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (See e.g., WO 90/05305). There are also several commercially available SPR biosensors (e.g., BiaCore, Uppsala, Sweden).

In some embodiments, compounds are screened in cell culture or in vivo (e.g., non-human or human mammals) for an ability to modulate mitochondrial ATP synthase activity. Any suitable assay may be utilized, including, but not limited to, cell proliferation assays (Commercially available from, e.g., Promega, Madison, Wis. and Stratagene, La Jolla, Calif.) and cell based dimerization assays. (See e.g., Fuh et al., Science, 256:1677 [1992]; Colosi et al., J. Biol. Chem., 268: 12617 [1993]). Additional assay formats that find use with the present invention include, but are not limited to, assays for measuring cellular ATP levels, and cellular superoxide levels.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In other embodiments, rational design methods are used to predict and model in silico ligand-receptor interactions prior to confirming results by routine experimentation.

VI. Therapeutic Applications

In certain embodiments, the present invention provides methods (e.g., therapeutic applications) for regulating cell death comprising: a) providing: i. target cells having mitochondria; and ii. a composition (e.g., exemplary compounds as described in Section III above); and b) exposing the target cells to the composition under conditions such that the exposure results in cell death. In some embodiments, the composition binds to the mitochondria so as to increase superoxide levels or alter cellular ATP levels in the target cells. Method of the present invention are not limited to particular target cells. In some embodiments, the target cells are selected from the group consisting of in vitro cells, in vivo cells, ex vivo cells, cancer cells, B cells, T cells, and granulocytes. The present invention is not limited to a particular therapeutic application. Non-limiting examples of therapeutic applications for the present invention are described in the following subsections.

A. General Therapeutic Applications

In particularly preferred embodiments, the compositions of the present invention are contemplated to provide therapeutic benefits to patients suffering from any one or more of a number of conditions (e.g., diseases characterized by dysregulation of necrosis and/or apoptosis processes in a cell or tissue, disease characterized by aberrant cell growth and/or hyperproliferation, etc.) by modulating (e.g., inhibiting or promoting) the activity of the mitochondrial ATP synthase (as referred to as mitochondrial $F_1F_0$-ATPase) complexes in affected cells or tissues. In further preferred embodiments, it is contemplated that the compositions of the present invention are used to treat immune/chronic inflammatory conditions (e.g., psoriasis). In even further embodiments, it is contemplated that the compositions of the present invention are used in conjunction with stenosis therapy to treat compromised (e.g., occluded) vessels.

In particularly preferred embodiments, it is contemplated that the compositions of the present invention inhibit the activity of mitochondrial ATP synthase complex by binding to a specific subunit of this multi-subunit protein complex. While the present invention is not limited to any particular mechanism, nor to any understanding of the action of the agents being administered, in some embodiments, it is contemplated that the compositions of the present invention bind to the oligomycin sensitivity conferring protein (OSCP) portion of the mitochondrial ATP synthase complex, to the OSCP/F1 junction, or to the F1 subunit. Likewise, it is further contemplated that when the compositions of the present invention bind to the OSCP the initial affect is overall inhibition of the mitochondrial ATP synthase complex, and that the downstream consequence of binding is a change in ATP or pH level and the production of reactive oxygen species (e.g., $O_2$—). In still other preferred embodiments, while the present invention is not limited to any particular mechanism, nor to any understanding of the action of the agents being administered, it is contemplated that the generation of free radicals ultimately results in cell killing. In yet other embodiments, while the present invention is not limited to any particular mechanism, nor to any understanding of the action of the agents being administered, it is contemplated that the inhibiting mitochondrial ATP synthase complex using the compositions and methods of the present invention provides therapeutically useful inhibition of cell proliferation.

Accordingly, it is contemplated that preferred methods embodied in the present invention, provide therapeutic benefits to patients by providing compounds of the present invention that modulate (e.g., inhibiting or promoting) the activity of the mitochondrial ATP synthase complexes in affected cells or tissues via binding to the oligomycin sensitivity conferring protein (OSCP) portion of the mitochondrial ATP synthase complex. Importantly, by itself the OSCP, the OSCP/F1 junction, or the F1 subunit has no biological activity.

Thus, in one broad sense, it is contemplated that preferred embodiments of the present invention are directed to the discovery that many diseases characterized by dysregulation of necrosis and/or apoptosis processes in a cell or tissue, or diseases characterized by aberrant cell growth and/or hyperproliferation, etc., can be treated by modulating the activity of the mitochondrial ATP synthase complex including, but not limited to, by binding to the oligomycin sensitivity conferring protein (OSCP) component thereof. The present invention is not intended to be limited, however, to the practice of the compositions and methods explicitly described herein. Indeed, those skilled in the art will appreciate that a number of additional compounds not specifically recited herein are suitable for use in the methods disclosed herein of modulating the activity of mitochondrial ATP synthase.

The present invention thus specifically contemplates that any number of suitable compounds presently known in the art, or developed later, can optionally find use in the methods of the present invention. For example, compounds including, but not limited to, oligomycin, ossamycin, cytovaricin, apoptolidin, bafilomyxcin, resveratrol, piceatannol, and dicyclohexylcarbodiimide (DCCD), and the like, find use in the methods of the present invention. The present invention is not intended, however, to be limited to the methods or compounds specified above. In one embodiment, that compounds potentially useful in the methods of the present invention may be selected from those suitable as described in the scientific literature. (See e.g., K. B. Wallace and A. A. Starkov, Annu Rev. Pharmacol. Toxicol., 40:353-388 [2000]; A. R. Solomon et al., Proc. Nat. Acad. Sci. U.S.A., 97(26):14766-14771 [2000]; and L. Galluzzi, N. Larochette, N. Zamzami and G. Kroemer, Oncogene 25: 4812-4830 [2006]).

In some embodiments, compounds potentially useful in methods of the present invention are screened against the National Cancer Institute's (NCI-60) cancer cell lines for efficacy. (See e.g., A. Monks et al., J. Natl. Cancer Inst., 83:757-766 [1991]; and K. D. Paull et al., J. Natl. Cancer Inst., 81:1088-1092 [1989]). Additional suitable screens (e.g., autoimmunity disease models, etc.) are within the skill in the art.

In other preferred embodiments, it is contemplated that the compositions of the present invention are used to treat drug sensitive and/or drug resistant *mycobacterium tuberculosis.*

In other preferred embodiments, it is contemplated that the compositions of the present invention are used in the treatment of angiogenesis.

In other preferred embodiments, it is contemplated that the compositions of the present invention are used in the treatment of cardiovascular disease.

In other preferred embodiments, it is contemplated that the compositions of the present invention are used in conjunction with stenosis therapy to treat compromised (e.g., occluded) vessels. In further embodiments, it is contemplated that the compositions of the present invention are used in conjunction with stenosis therapy to treat compromised cardiac vessels.

Vessel stenosis is a condition that develops when a vessel (e.g., aortic valve) becomes narrowed. For example, aortic valve stenosis is a heart condition that develops when the valve between the lower left chamber (left ventricle) of the heart and the major blood vessel called the aorta becomes narrowed. This narrowing (e.g., stenosis) creates too small a space for the blood to flow to the body. Normally the left ventricle pumps oxygen-rich blood to the body through the aorta, which branches into a system of arteries throughout the body. When the heart pumps, the 3 flaps, or leaflets, of the aortic valve open one way to allow blood to flow from the ventricle into the aorta. Between heartbeats, the flaps close to form a tight seal so that blood does not leak backward through the valve. If the aortic valve is damaged, it may become narrowed (stenosed) and blood flow may be reduced to organs in the body, including the heart itself. The long-term outlook for people with aortic valve stenosis is poor once symptoms develop. People with untreated aortic valve stenosis who develop symptoms of heart failure usually have a life expectancy of 3 years or less.

Several types of treatment exist for treating compromised valves (e.g., balloon dilation, ablation, atherectomy or laser treatment). One type of treatment for compromised cardiac valves is angioplasty. Angioplasty involves inserting a balloon-tipped tube, or catheter, into a narrow or blocked artery in an attempt to open it. By inflating and deflating the balloon several times, physicians usually are able to widen the artery.

A common limitation of angioplasty or valve expansion procedures is restenosis. Restenosis is the reclosure of a peripheral or coronary artery following trauma to that artery caused by efforts to open a stenosed portion of the artery, such as, for example, by balloon dilation, ablation, atherectomy or laser treatment of the artery. For these angioplasty procedures, restenosis occurs at a rate of about 20-50% depending on the definition, vessel location, lesion length and a number of other morphological and clinical variables. Restenosis is believed to be a natural healing reaction to the injury of the arterial wall that is caused by angioplasty procedures. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

In an attempt to prevent restenosis, metallic intravascular stents have been permanently implanted in coronary or peripheral vessels. The stent is typically inserted by catheter into a vascular lumen told expanded into contact with the diseased portion of the arterial wall, thereby providing mechanical support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

To address the restenosis problem, it has been proposed to provide stents which are seeded with endothelial cells (Dichek, D. A. et al; Circulation 1989; 80: 1347-1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed (see, e.g., International Patent Applications WO 91/12779, and WO 90/13332; each herein incorporated by reference in their entireties). In those applications, it is suggested that antiplatelet agents, anticoagulant agents, antimicrobial agents, anti-inflammatory agents, antimetabolic agents and other drugs could be supplied in stents to reduce the incidence of restenosis. Further, other vasoreactive agents such as nitric oxide releasing agents could also be used.

An additional cause of restenosis is the over-proliferation of treated tissue. In some embodiments, it is contemplated that the anti-proliferative properties of the present invention inhibit restenosis. Drug-eluting stents are well known in the art (see, e.g., U.S. Pat. No. 5,697,967; U.S. Pat. No. 5,599,352; and U.S. Pat. No. 5,591,227; each of which are herein incorporated by reference). In some embodiments, the compositions of the present invention are eluted from drug-eluting stents in the treatment of compromised (e.g., occluded) vessels. In further embodiments, the compositions of the present invention are eluted from drug-eluting stents in the treatment of compromised cardiac vessels.

Those skilled in the art of preparing pharmaceutical compounds and formulations will appreciate that when selecting optional compounds for use in the methods disclosed herein, that suitability considerations include, but are not limited to, the toxicity, safety, efficacy, availability, and cost of the particular compounds.

In some embodiments, pharmaceutical compositions comprise compounds of the invention and, for example, therapeutic agents (e.g., antiatherosclerotic agents, anticoagulants, antithrombotic agents, antihypertensive agents, potassium channel openers, calcium channel blockers, sodium hydrogen exchanger inhibitors, antiarrhythmic agents, prothrombolytic agents, fibrinogen antagonists, diuretics, ATPase inhibitors, mineralocorticoid receptor antagonists, phosphodiesterase inhibitors, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, and antidiabetic agents). Antihypertensive agents include, but are not limited to, ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$ and $P2Y_{12}$ antagonists, thromboxane receptor antagonists, and aspirin.

In some embodiments, the compounds of the present invention are useful in treating a mitochondrial $F_1F_0$-ATP hydrolase associated disorder (e.g., myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, medication, pregnancy and fetal loss, and diabetic complications comprising retinopathy, nephropathy and neuropathy) in a patient.

B. Immune Disorder, Autoimmune Disorder, and Chronic Inflammatory Disorder Therapeutic Application Immune disorders and chronic inflammatory disorders often result from dysfunctional cellular proliferation regulation and/or cellular apoptosis regulation. Mitochondria perform a key role in the control and execution of cellular apoptosis. The mitochondrial permeability transition pore (MPTP) is a pore that spans the inner and outer mitochondrial membranes and functions in the regulation of proapoptotic particles. Transient MPTP opening results in the release of cytochrome c and the apoptosis inducing factor from the mitochondrial intermembrane space, resulting in cellular apoptosis.

The oligomycin sensitivity conferring protein (OSCP) is a subunit of the $F_1F_0$ mitochondrial ATP synthase/ATPase and functions in the coupling of a proton gradient across the $F_0$ sector of the enzyme in the mitochondrial membrane. In some embodiments, it is contemplated that compounds of the present invention bind the OSCP, the OSCP/$F_1$ junction, or the $F_1$ subunit, increases superoxide and cytochrome c levels, increases cellular apoptosis, and inhibits cellular proliferation. The adenine nucleotide translocator (ANT) is a 30 kDa protein that spans the inner mitochondrial membrane and is central to the mitochondrial permeability transition pore (MPTP). Thiol oxidizing or alkylating agents are powerful activators of the MPTP that act by modifying one or more of three unpaired cysteines in the matrix side of the ANT. 4-(N—(S-glutathionylacetyl)amino)phenylarsenoxide, inhibits the ANT.

In certain embodiments, the present invention provides a method for treating an immune disorder (e.g., graph versus host disease, rheumatoid arthritis, or systemic lupus erythematosus), a hyperproliferative disorder (e.g., cancer), or a chronic inflammatory disease (e.g., asthma or psoriasis). In certain embodiments, the cancer is myeloma, bladder cancer, or renal cancer.

C. Treatment of Epidermal Hyperplasia

Epidermal hyperplasia (e.g., excessive keratinocyte proliferation) leading to a significant thickening of the epidermis in association with shedding of the thickened epidermis, is a feature of diseases such as psoriasis (see, e.g., Krueger G C, et al., (1984) J. Am. Acad. Dermatol. 11: 937-947; Fry L. (1988), Brit. J. Dermatol. 119:445-461; each herein incorporated by reference in their entireties) and also occurs under physiological conditions (e.g., during wound-healing).

Topical treatment of the skin with all-trans retinoic acid (RA) or its precursor, all-trans retinol (ROL) also results in epidermal hyperplasia (see, e.g., Varani J, et al., (2001) J. Invest. Dermatol, 117:1335-1341; herein incorporated by reference in its entirety). While the underlying etiologies are different, all of these hyperplasias have in common the activation of the epidermal growth factor (EGF) receptor in the proliferating keratinocytes (see, e.g., Varani J, et al., (2001) J. Invest. Dermatol 117:1335-1341; Baker B S, et al., (1992) Brit. J. Dermatol. 126:105-110; Gottlieb A B, et al., (1988) J. Exp. Med. 167:670-675; Elder J T, et al., (1989) Science 243:811-814; Piepkorn M, et al., (1998) J Invest Dermatol 111:715-721; Piepkorn M, et al., (2003) Arch Dermatol Res 27:27; Cook P W, et al., (1992) Cancer Res 52:3224-3227; each herein incorporated by reference in their entireties). Normal epidermal growth does not appear to be as dependent on EGF receptor function as hyperplastic growth (see, e.g., Varani J, et al., (2001) J. Invest. Dermatol 117:1335-1341; Varani J, et al., (1998) Pathobiology 66:253-259; each herein incorporated by reference in their entireties). Likewise, function of the dermis in intact skin does not depend on EGF receptor function (see, e.g., Varani J, et al., (2001) J. Invest. Dermatol 117:1335-1341; herein incorporated by reference in its entirety).

The central role of the EGF receptor in regulating hyperplastic epithelial growth makes the EGF receptor tyrosine kinase a target for antiproliferative agents. Likewise, the series of signaling molecules engaged downstream of this receptor are additional points at which keratinocyte growth can be interrupted. The mitogen activated protein kinase (MAPK) cascade is activated by the EGF receptor (see, e.g., Marques, S. A., et al., (2002) J Pharmacol Exp Ther 300, 1026-1035; herein incorporated by reference in its entirety). In hyperproliferative epidermis, but not in normal epidermis, extracellular signal-regulated kinases 1/2 (Erk 1/2) are activated in basal and suprabasal keratinocytes and contribute to epidermal hyperproliferation (see, e.g., Haase, I., et al., (2001) J Clin Invest 108, 527-536; Takahashi, H., et al., (2002) J Dermatol Sci 30, 94-99; each herein incorporated by reference in their entireties). In culture models, keratinocyte growth regulation through the EGF receptor results in increased MAPK activity. In keratinocytes, growth factor-stimulated MAPK activity is also dependent on integrin engagement and extracellular matrix molecules that bind integrins are capable of independently activating MAPKs and increasing keratinocyte proliferation (see, e.g., Haase, I., et al., (2001) J Clin Invest 108, 527-536; herein incorporated by reference in its entirety). The proliferation of other skin cells, including fibroblasts, is less dependent on Erk 1/2 activity, making Erk inhibition a potentially useful characteristic to evaluate lead compounds for potential utility against epidermal hyperplasia.

In some embodiments, it is contemplated that compounds of the present invention are useful for treating epidermal hyperplasias.

In some embodiments, it is contemplated that compounds of the present invention are useful in treating psoriasis. Psoriasis is common and chronic epidermal hyperplasia. Plaque psoriasis is the most common type of psoriasis and is characterized by red skin covered with silvery scales and inflammation. Patches of circular to oval shaped red plaques that itch or burn are typical of plaque psoriasis. The patches are usually found on the arms, legs, trunk, or scalp but may be found on any part of the skin. The most typical areas are the knees and elbows. Psoriasis is not contagious and can be inherited. Environmental factors, such as smoking, sun exposure, alcoholism, and HIV infection, may affect how often the psoriasis occurs and how long the flares up last.

Treatment of psoriasis includes topical steroids, coal tar, keratolytic agents, vitamin D-3 analogs, and topical retinoids. Topical steroids are agents used to reduce plaque formation. Topical steroid agents have anti-inflammatory effects and may cause profound and varied metabolic activities. In addition, topical steroid agents modify the body's immune response to diverse stimuli. Examples of topical steroids include, but are not limited to, triamcinolone acetonide (Aristocort, Kenalog) 0.1% cream, and betamethasone dipropionate (Diprolene, Diprosone) 0.05% cream. Coal tar is an inexpensive treatment available over the counter in shampoos or lotions for use in widespread areas of involvement. Coal tar is particularly useful in hair-bearing areas. An example of coal tar is coal tar 2-10% (DHS Tar, Doctar, Theraplex T)-antipruitic. Keratolytic agents are used to remove scale, smooth the skin, and to treat hyperkeratosis. An example of a keratolytic agent is anthralin 0.1-1% (Drithocreme, Anthra-Derm). Vitamin D-3 analogs are used in patients with lesions resistant to older therapy or with lesions on the face or exposed areas where thinning of the skin would pose cosmetic problems. An example of a vitamin D-3 analog is calcipotriene (Dovonex). Topical retinoids are agents that decrease the cohesiveness of follicular epithelial cells and stimulate mitotic activity, resulting in an increase in turnover of follicular epithelial cells. Examples of topical retinoids include, but are not limited to, tretinoin (Retin-A, Avita), and tazarotene (Tazorac).

Approximately 1-2% of people in the United States, or about 5.5 million, have plaque psoriasis. Up to 30% of people with plaque psoriasis also have psoriatic arthritis. Individuals with psoriatic arthritis have inflammation in their joints and may have other arthritis symptoms. Sometimes plaque psoriasis can evolve into more severe disease, such as pustular psoriasis or erythrodermic psoriasis. In pustular psoriasis, the red areas on the skin contain blisters with pus. In erythrodermic psoriasis, a wide area of red and scaling skin is typical, and it may be itchy and painful. The present invention is useful in treating additional types of psoriasis, including but not limited to, guttate psoriasis, nail psoriasis, inverse psoriasis, and scalp psoriasis.

In some embodiments, the compounds of the present invention are useful in treating pigmentation disorders (e.g., albinism, melasma, and vitiligo). The present invention is not limited to a particular mechanism for treating pigment disorders. In some embodiments, pigment disorders are treated through targeting of the $F_1F_o$-ATPase by the compounds of the present invention. In further embodiments, pigment disorders are treated through the rerouting of tyrosinase by the compounds of the present invention. In further embodiments, pigment disorders are treated through targeting of prohibitin by the compounds of the present invention.

D. Stenosis Therapy

In some embodiments, the compositions of the present invention are used in conjunction with stenosis therapy to treat compromised (e.g., occluded) vessels. In further embodiments, the compositions of the present invention are used in conjunction with stenosis therapy to treat compromised cardiac vessels.

Vessel stenosis is a condition that develops when a vessel (e.g., aortic valve) becomes narrowed. For example, aortic valve stenosis is a heart condition that develops when the valve between the lower left chamber (left ventricle) of the heart and the major blood vessel called the aorta becomes narrowed. This narrowing (e.g., stenosis) creates too small a space for the blood to flow to the body. Normally the left ventricle pumps oxygen-rich blood to the body through the aorta, which branches into a system of arteries throughout the body. When the heart pumps, the 3 flaps, or leaflets, of the aortic valve open one way to allow blood to flow from the ventricle into the aorta. Between heartbeats, the flaps close to form a tight seal so that blood does not leak backward through the valve. If the aortic valve is damaged, it may become narrowed (stenosed) and blood flow may be reduced to organs in the body, including the heart itself. The long-term outlook for people with aortic valve stenosis is poor once symptoms develop. People with untreated aortic valve stenosis who develop symptoms of heart failure usually have a life expectancy of 3 years or less.

Several types of treatment exist for treating compromised valves (e.g., balloon dilation, ablation, atherectomy or laser treatment). One type of treatment for compromised cardiac valves is angioplasty. Angioplasty involves inserting a balloon-tipped tube, or catheter, into a narrow or blocked artery in an attempt to open it. By inflating and deflating the balloon several times, physicians usually are able to widen the artery.

A common limitation of angioplasty or valve expansion procedures is restenosis. Restenosis is the reclosure of a peripheral or coronary artery following trauma to that artery caused by efforts to open a stenosed portion of the artery, such as, for example, by balloon dilation, ablation, atherectomy or laser treatment of the artery. For these angioplasty procedures, restenosis occurs at a rate of about 20-50% depending on the definition, vessel location, lesion length and a number of other morphological and clinical variables. Restenosis is believed to be a natural healing reaction to the injury of the arterial wall that is caused by angioplasty procedures. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

In an attempt to prevent restenosis, metallic intravascular stents have been permanently implanted in coronary or peripheral vessels. The stent is typically inserted by catheter into a vascular lumen told expanded into contact with the diseased portion of the arterial wall, thereby providing mechanical support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

To address the restenosis problem, it has been proposed to provide stents which are seeded with endothelial cells (Dichek, D. A. et al Seeding of Intravascular Stents With Genetically Engineered Endothelial Cells; Circulation 1989; 80: 1347-1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed such as in international patent application WO 91/12779 "Intraluminal Drug Eluting Prosthesis" and international patent application WO 90/13332 "Stent With Sustained Drug Delivery". In those applications, it is suggested that antiplatelet agents, anticoagulant agents, antimicrobial agents, anti-inflammatory agents, antimetabolic agents and other drugs could be supplied in stents to reduce the incidence of restenosis. Further, other vasoreactive agents such as nitric oxide releasing agents could also be used.

An additional cause of restenosis is the over-proliferation of treated tissue. In some embodiments, the anti-proliferative properties of the present invention inhibit restenosis. Drug-eluting stents are well known in the art (see, e.g., U.S. Pat. No. 5,697,967; U.S. Pat. No. 5,599,352; and U.S. Pat. No. 5,591,227; each of which are herein incorporated by reference). In some embodiments, the compositions of the present invention are eluted from drug-eluting stents in the treatment of compromised (e.g., occluded) vessels. In further embodiments, the compositions of the present invention are eluted from drug-eluting stents in the treatment of compromised cardiac vessels.

E. Treatment of Bacterial Infections

In some embodiments, benzodiazepine compounds and related compounds (see, e.g., Section III—Exemplary Compounds) are used to treat a subject suffering from a bacterial infection. In some embodiments, more than one of the compounds of the present invention are used to treat a subject suffering from a bacterial infection. In some embodiments, the compounds of the present invention treat bacterial infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of bacterial infections. Examples of bacterial infections include, but are not limited to, Anthrax, Bacterial Meningitis, Brucellosis, Campylobacteriosis, Cat Scratch Disease, Cholera, Diphtheria, Epidemic Typhus, Gonorrhea, Impetigo—Legionellosis, Leprosy (Hansen's Disease), Leptospirosis, Listeriosis, Lyme Disease, Melioidosis, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus; and Urinary Tract Infections. In some embodiments, the compounds of the present invention are co-administered with at least one additional agent for purposes of treating bacterial infections. Examples of addition agents for purposes of treating bacterial infections include, but are not limited to, Cephalosporins, Macrolides, Penicillins, Quinolones, Sulfonamides and Related Compounds, and Tetracyclines.

F. Treatment of Viral Infections

In some embodiments, benzodiazepine compounds and related compounds (see, e.g., Section III—Exemplary Compounds) are used to treat a subject suffering from a viral infection. In some embodiments, more than one of the compounds of the present invention are used to treat a subject suffering from a viral infection. In some embodiments, the compounds of the present invention treat viral infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of viral infections. Examples of viral infections include, but are not limited to, AIDS, AIDS Related Complex, Chickenpox (Varicella), Common cold, Cytomegalovirus Infection, Colorado tick fever, Dengue fever, Ebola haemorrhagic fever, Epidemic parotitis, Hand, foot and mouth disease, Hepatitis, Herpes simplex, Herpes zoster, HPV, Influenza (Flu), Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever. In some embodiments, the compounds of the present invention are co-administered with at least one additional agent for purposes of treating viral infections. Examples of additional agents for purposes of treating viral infections include, but are not limited to, Ganciclovir, Interferon-alpha-2b, Acyclovir, Famciclovir, and Valaciclovir.

G. Treatment of Fungal Infections

In some embodiments, benzodiazepine compounds and related compounds (see, e.g., Section III—Exemplary Compounds) are used to treat a subject suffering from a fungal infection. In some embodiments, more than one of the compounds of the present invention are used to treat a subject suffering from a fungal infection. In some embodiments, the compounds of the present invention treat fungal infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of fungal infections. Examples of fungal infections include, but are not limited to, Aspergillosis, Blastomycosis, Candidiasis, Coccidioidomycosis, Cryptococcosis, Histoplasmosis, Tinea pedis. In some embodiments, the compounds of the present invention are co-administered with at least one additional agent for purposes of treating fungal infections. Examples of additional agents for purposes of treating fungal infections include, but are not limited to, betamethasone, butenafine, ciclopirox, clioquinol, hydrocortisone, clotrimazole, econazole, flucytosine, griseofulvin, haloprogin, itraconazole, ketoconazole, miconazole, naftifine, nystatin, triamcinolone, oxiconazole, sulcanazole, terbinafine, terconazole, tolnaftate, and voriconazole.

H. Treatment of Parasitic Infections

In some embodiments, benzodiazepine compounds and related compounds (see, e.g., Section III—Exemplary Compounds) are used to treat a subject suffering from a parasitic infection. In some embodiments, more than one of the compounds of the present invention are used to treat a subject suffering from a parasitic infection. In some embodiments, the compounds of the present invention treat parasitic infections through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of parasitic infections. Examples of parasitic infections include, but are not limited to, African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolpsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, and Trypanosomiasis. In some embodiments, the compounds of the present invention are co-administered with at least one additional agent for purposes of treating parasitic infections. Examples of additional agents for purposes of treating parasitic infections include, but are not limited to, antihelminthic agents (e.g., albendazole (Albenza), mebendazole (Vermox), niclosamide (Niclocide), oxamniquine (Vansil), praziquantel (Biltricide), pyrantel (Antiminth), pyantel pamoate (Antiminth), thiabendazole (Mintezol), bitional, ivermectin, and diethylcarbamazepine citrate.

I. Treatment of Prion Infectious Diseases

In some embodiments, benzodiazepine compounds and related compounds (see, e.g., Section III—Exemplary Compounds) are used to treat a subject suffering from a prion infectious disease. In some embodiments, more than one of the compounds of the present invention are used to treat a subject suffering from a prion infectious disease. In some embodiments, the compounds of the present invention treat prion infectious diseases through modulating (e.g., inhibiting or promoting) the activity of ATP synthase complexes (e.g., mitochondrial ATP synthase complexes or homolog in organisms that do not have mitochondria) in affected cells or tissues via binding to the oligomycin sensitivity conferring protein (OSCP) portion/F1 of the ATP synthase complex (e.g., mitochondrial ATP synthase complex). The present invention is not limited to particular types of prion infectious diseases. Examples of parasitic infectious diseases include, but are not limited to, transmissible spongiform encephalopathy, Bovine spongiform encephalopathy, Creutzfeldt-Jakob disease, and Kuru. In some embodiments, the compounds of the present invention are co-administered with at least one additional agent for purposes of treating prion infectious diseases. Examples of additional agents for purposes of treating prion infectious diseases include, but are not limited to, Congo red and its analogs, anthracyclines, amphotericin B and its analogs, sulfated polyanions, and tetrapyrroles.

J. Treatment of Diseases Involving Aberrant Angiogenesis

In some embodiments, benzodiazepine compounds and related compounds (see, e.g., Section III—Exemplary Compounds) are used to treat a subject suffering from a disease involving aberrant angiogenesis. In some embodiments, more than one of the compounds of the present invention are used to treat diseases involving aberrant angiogenesis through modulating (e.g., inhibiting or promoting) the activity of ATP synthase complexes (e.g., mitochondrial ATP synthase complexes) in affected cells or tissues undergoing aberrant angiogenesis via binding to the oligomycin sensitivity conferring protein (OSCP) portion/F1 of the ATP synthase complex (e.g., mitochondrial ATP synthase complex). The present invention is not limited to particular types of disease involving aberrant angiogenesis. Examples of diseases involving aberrant angiogenesis include, but are not limited to, cancers (e.g., cancers involving solid tumors), psoriasis, diabetic retinopathy, macular degeneration, atherosclerosis and rheumatoid arthritis.

Examples of additional agents for treating diseases involving aberrant angiogenesis include, but are not limited to, Dalteparin, ABT-510, CNGRC peptide TNF alpha conjugate (NGR-TNF), Combretastatin A4 Phosphate, Dimethylxanthenone Acetic Acide, Lenalidomide, LY317615, PPI-2458, Soy Isoflavone (Genistein; Soy Protein Isolate), Tamoxifen Citrate, Thalidomide, ADH-1, AG-013736, AMG-706, Anti-VEGF Antibody, AZD2171, Bay 43-9006, GW786034, CHIR-265, PI-88, PTK787/ZK 222584, RAD001, Suramin, SU11248, XL184, ZD6474, ATN-161, EMD 121974, and Celecoxib. Additional agents for treating diseases involving aberrant angiogenesis include anti-cancer drugs (e.g., Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda). Other anti-cancer agents include, but are not limited to, Antiproliferative agents (e.g., Piritrexim Isothionate), Antiprostatic hypertrophy agent (e.g., Sitogluside), Benign prostatic hyperplasia therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Additional anti-cancer agents include, but are not limited to anti-cancer Supplementary Potentiating Agents Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-Cl-2' deoxyadenosine; Fludarabine-$PO_4$; mitoxantrone; mitozolomide; Pentostatin; and Tomudex. One particularly preferred class of anticancer agents are taxanes (e.g., paclitaxel and docetaxel). Another important category of anticancer agent is annonaceous acetogenin.

K. Blood Pressure Regulation

In some embodiments, benzodiazepine compounds and related compounds (see, e.g., Section III—Exemplary Compounds) are used to regulate a subject's blood pressure. In some embodiments, more than one of the compounds of the present invention are used to treat regulate a subject's blood pressure (e.g., maintain a subject's blood pressure within a desired range). In some embodiments, the compounds of the present invention regulate blood pressure through modulating (e.g., inhibiting or promoting) the activity of ATP synthase complexes (e.g., mitochondrial ATP synthase complexes) in affected cells or tissues via binding to the oligomycin sensitivity conferring protein (OSCP) portion/F1 of the ATP synthase complex (e.g., mitochondrial ATP synthase complex). In some embodiments, the compounds of the present invention are co-administered with at least one additional agent for purposes of regulating a subject's blood pressure. Examples of additional agents for purposes of regulating a subject's blood pressure include, but are not limited to, thiazides and related diuretics (e.g., hydrochlorothiazide, chlorthalidone), alpha/beta-adrenergic blocking agents (e.g., carvedilol), beta-adrenergic blocking agents (e.g., bisoprolol, atenolol, metoprolol), angiotensin-converting enzyme inhibitors (e.g., captopril, fosinopril, benazepril, quinapril, ramipril), angiotensin II receptor antagonists (e.g., losartan, valsartan, candesartan, irbesartan, eprosartan, and olmesartan), calcium channel blockers—nondihydropyridines (e.g., diltiazem, and verapamil), calcium channel blockers—dihydropyridines (e.g., Amlodipine, nifedipine, felodipine), vasodilators—peripheral (e.g., hydralazine), aldosterone antagonists (e.g., spironolactone).

L. HDL/LDL Regulation

In some embodiments, benzodiazepine compounds and related compounds (see, e.g., Section III—Exemplary Compounds) are used to regulate a subject's HDL/LDL levels. In some embodiments, more than one of the compounds of the present invention are used to treat regulate a subject's HDL/LDL levels (e.g., lower a subject's LDL levels, raise a subject's HDL levels). In some embodiments, the compounds of the present invention regulate HDL/LDL levels through modulating (e.g., inhibiting or promoting) the activity of ATP synthase complexes (e.g., mitochondrial ATP synthase complexes) in affected cells or tissues via binding to the oligomycin sensitivity conferring protein (OSCP) portion/F1 of the ATP synthase complex (e.g., mitochondrial ATP synthase complex). In some embodiments, the compounds of the present invention are co-administered with at least one additional agent for purposes of regulating a subject's HDL/LDL levels. Examples of additional agents for purposes of regulating a subject's HDL/LDL levels include, but are not limited to, antilipemic agents (e.g., niacin, nicotinic acid, gemfibrozil, fenofibrate), and HMG-CoA reductase inhibitors (e.g., atorvastatin, simvastatin, pravastatin, lovastatin, fluvastatin, and rosuvastatin).

EXAMPLES

The invention now being generally described, will be more readily understood by reference to the following examples, which are included merely for purposes of illustration of certain aspects and embodiments of the present invention, and are not intended to limit the invention.

Example 1

Representative General Procedures for Synthesis of Benzodiazepine Cores

Part I:

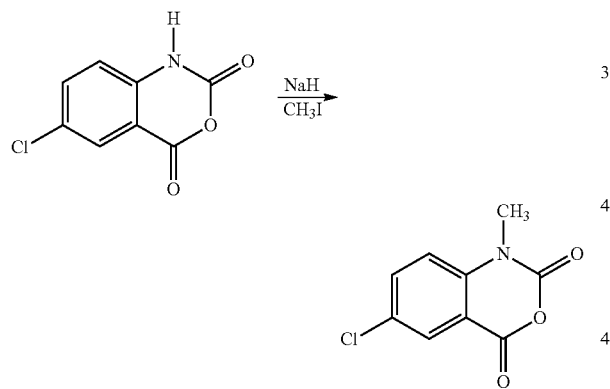

6-Chloro-1-methyl-1H-benzo[d][1,3]oxazine-2,4-dione (Compound B where R=CH$_3$). In a 3 L, 3 neck RBF equipped with mechanical stir, addition funnel, thermocouple and N$_2$ inlet, NaH (30.4 g) was suspended in anhydrous THF (400 mL). While stirring at room temperature, a suspension of 5-chloroisotonic anhydride in THF (400 mL) was added in portion-wise manner over 45 min. The reaction mixture was stirred for 50 min (reaction temperature went up from 18 to 28° C.). To this was added CH$_3$I (285 g, 125 mL) over 15 min. The mixture was then stirred at 42° C. for 16 h. Because TLC showed that some unreacted starting material was still present in the reaction mixture, an additional 30 mL of CH$_3$I was added and the reaction mixture stirred at 42° C. for an additional 3 h. Reaction mixture was cooled (RT) and quenched by the slow (40 min) addition of AcOH (55 mL). Reaction mixture was concentrated to give 275 g thick syrupy product, which was used without any further purification. $^1$H NMR (300 MHz, CDCl$_3$) δ 3.35 (s, 3H), 7.54 (d, 1H), 7.85 (d, 1H), 7.90 (s, 1H).

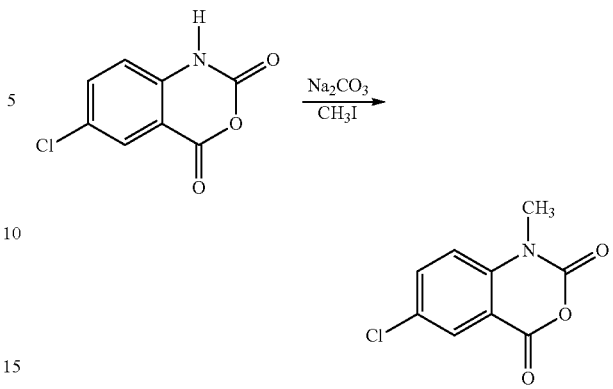

6-Chloro-1-methyl-1H-benzo[d][1,3]oxazine-2,4-dione (Compound B where R=CH$_3$). 6-Chloro-1Hbenzo[d][1,3]oxazine-2,4-dione (22.88 g, 116 mmol) was dissolved in dimethylformamide (150 mL), and sodium carbonate (14.73 g, 139 mmol) was added. Methyl iodide (10.86 mL, 174 mmol) was then added dropwise. The reaction was stirred at room temperature overnight. Water (150 mL) was then added, and the mixture was stirred for 1 hour. The solid was collected by filtration. The impure solid was sonicated in methyl-tert-butyl ether for several minutes, and then collected by filtration yielding the product as a white solid (19.38 g, 79%). $^1$H NMR (300 MHz, DMSO-d$_6$) δ 3.45 (s, 3H), 7.47 (d, 1H), 7.89 (dd, 1H), 7.94 (d, 1H).

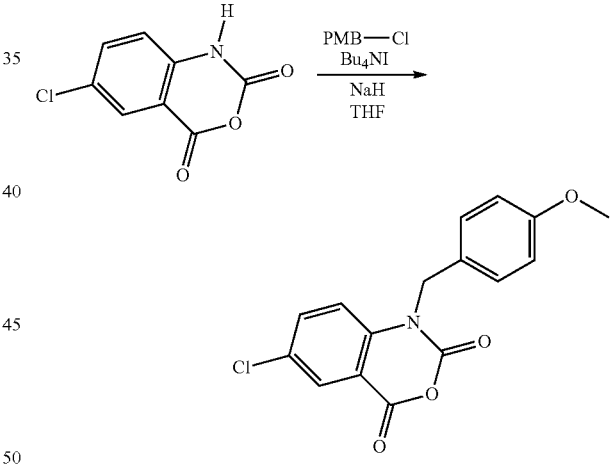

6-Chloro-1-(4-methoxybenzyl)-1H-benzo[d][1,3]oxazine-2,4-dione (Compound B where R=PMB). In a 3 L, 3-neck RBF equipped with mechanical stir, thermocouple and N$_2$ inlet, 90 g (0.455 mol) of 5-chloroisotonic anhydride was suspended in anhydrous THF (0.9 L). Under N$_2$, 4-methoxybenzylchloride (75 g, 0.48 mol) was added followed by the addition of tetrabutylammonium iodide (84 g, 0.23 mol). The reaction mixture was stirred for 5 min at room temperature and then 20 g (0.5 mol) of NaH was added portion-wise over 20 min (reaction temperature increased to 29° C. due to an exotherm and therefore reaction mixture was placed into water bath to keep the temperature below 30° C.). Reaction was stirred for 16 h (RT). Next day HPLC showed about 26% unreacted 5-chloroisotonic anhydride. Additional NaH (1 g) was added and the reaction mixture was heated to 32° C. and stirred for another 5 h. NMR showed that all of the starting material had been consumed. Reaction was quenched by adding 10 g of glacial acetic acid slowly followed by stirring for 30 min. Reaction mixture was filtered through celite and filter cake was washed with THF. Filtrate was concentrated to give 280 g of crude product (yellow-brown solid), which was used with no further purification. $^1$H NMR (300 MHz, DMSO-$d_6$) δ 3.8 (s, 3H), 5.25 (s, 2H), 6.8 (d, 2H), 7.2 (m, 3H), 7.75 (d, 1H), 7.9 (d, 1H).

Part II:

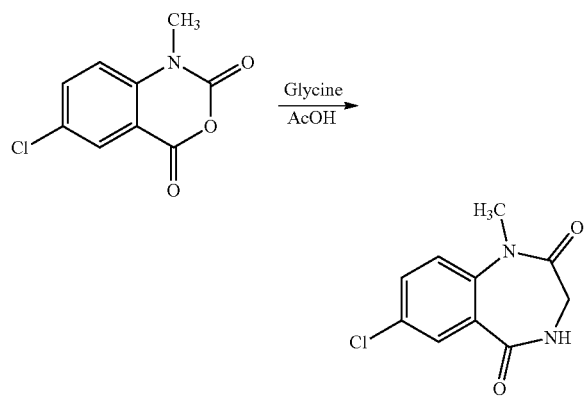

7-Chloro-1-methyl-3,4-dihydro-1H-benzo[e][1,4]diazepine-2,5-dione (Compound C where R=Me). In a 2 L RBF equipped with mechanical stir, condenser and N$_2$ inlet, glycine (38 g, 0.506 mol) was added to crude 6-chloro-1-methyl-1H-benzo[d][1,3]oxazine-2,4-dione (107 g, 0.506 mol) followed by the addition of AcOH (500 mL). Reaction flask was heated in a 130° C. oil bath for 7 h. Solvent was evaporated under suction with heating (50-60° C.). To the thick syrupy crude product was added 1 L of EtOAc followed by the slow addition of aqueous NaHCO$_3$ (saturated) to adjust the pH to ~7. Then 10 mL of 2 M NaOH was added to adjust the pH to ~9-10. The mixture gave a solid along with organic and aqueous layers. Solid was filtered to give product containing some impurity. Solid was partitioned between 400 mL DCM and 200 mL NaHCO$_3$ and the slurry was stirred for 20 min, then filtered to remove the insoluble impurity. The DCM layer was separated and washed with 3% NaHCO$_3$ and then brine (200 mL). The DCM layer was dried (MgSO$_4$), filtered and concentrated to give 50 g of pure product. EtOAc layer was concentrated to give 67 g of solid product with some impurity. Aqueous layer was extracted with EtOAc (2×400 mL). Combined organics were dried over Na$_2$SO$_4$, filtered and concentrated to give an additional 6.7 g of crude product. Total of 123.4 g of product was obtained, 50 g of which was very clean. $^1$H NMR (300 MHz, CDCl$_3$) δ 3.2 (s, 3H), 3.5 (m, 1 H), 3.8 (m, 1H), 7.35 (d, 1H), 7.6 (m, 2H), 8.8 (t, 1H).

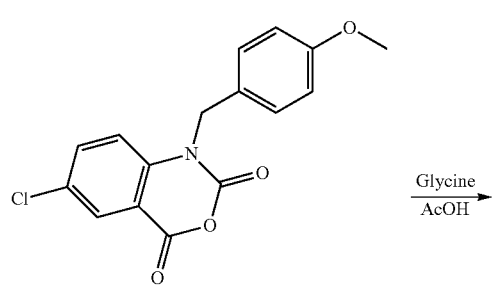

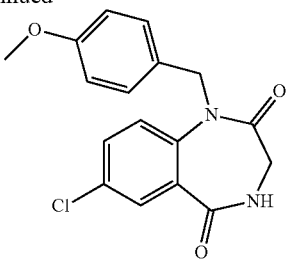

7-Chloro-1-(4-methoxybenzyl)-3,4-dihydro-1H-benzo[e][1,4]diazepine-2,5-dione (Compound C where R=PMB). In a 2 L RBF equipped with mechanical stir, condenser and N$_2$ inlet, glycine (34 g, 0.45 mol) was added to 6-chloro-1-(4-methoxybenzyl)-1H-benzo[d][1,3]oxazine-2,4-dione (280 g) followed by the addition of AcOH (500 mL). Reaction flask was heated in a 130° C. oil bath for 8 h. Solvent was removed on the rotary evaporator at 50-60° C. To the thick syrupy crude product was added heptane (1 L) and H$_2$O (1 L) followed by the addition of NaHCO$_3$ to adjust the pH to ~8-9. The mixture gave a solid along with organic and aqueous layers. The organic and aqueous layers were decanted and the solid was slurried with 500 mL of 5% NaHCO$_3$ solution. NaHCO$_3$ layer was decant and sticky solid was suspended in 700 mL EtOAc and 300 mL of dichloromethane (DCM). The mixture was stirred for 20 min, filtered and the filter cake was washed with 1 L of DCM. The filtrate was concentrated and residue was pass through 330 g silica gel plug using 25/75 to 75/25 EtOAC/heptane (total of 8 L). Clean fractions were combined to give 58 g of pure product. An additional 13 g of ~70% pure product was obtained from less pure fractions. Yield was 47% over two steps. $^1$H NMR (300 MHz, DMSO-$d_6$) δ 3.45 (m, 1H), 3.6 (s, 3H), 3.8 (m, 1H), 4.8 (d, 1H), 5.3 (d, 1H), 6.8 (d, 2 H), 7.1 (d, 2H), 7.7-7.5 (m, 3H), 8.9 (t, 1H).

Example 2

Representative General Procedure for Simultaneous Synthesis of the Benzodiazepine Core and Installation of C3 Functionality

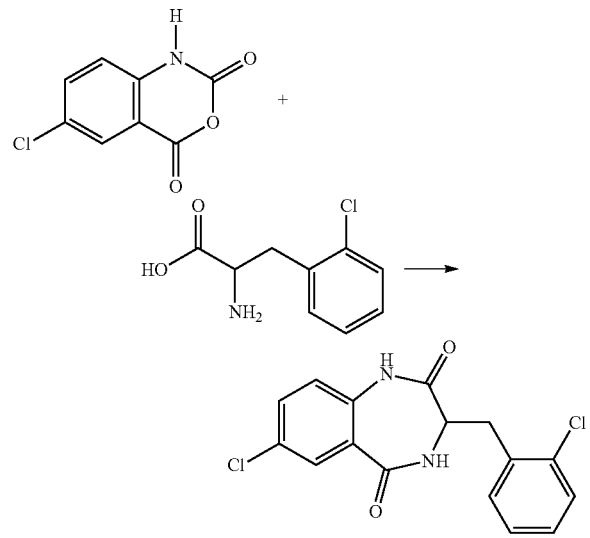

7-Chloro-3-(2-chlorobenzyl)-3,4-dihydro-1H-benzo[e][1,4]diazepine-2,5-dione. 2-Amino-3-(2-chlorophenyl)propanoic acid hydrochloride (3.0 g, 12.7 mmol) was suspended in acetonitrile (50 mL) and water (5 mL), triethylamine (3.57 mL, 25.4 mmol) was added which caused a precipitate to form and inefficient stirring. Water (10 mL) was added until all solids were dissolved. 5-Chloroisatoic anhydride (2.51 g, 12.7 mmol) was added in portions, waiting until each portion dissolved before adding the next. Successive portions required longer periods of time, up to 15 minutes for the last portions. After the last portion was added, the suspension was sonicated for several minutes then stirred at ambient temperature overnight. The clear solution was concentrated in vacuo then azeotroped twice with acetone. The residue was redissolved in acetic acid (30 mL) and heated to 130° C. for 6 hours. The mixture was concentrated in vacuo to an oil, diluted with ethyl acetate (150 mL), washed with water (3×50 mL) then brine, dried with sodium sulfate, filtered and concentrated to a brown solid. This solid was resuspended in ethyl acetate (20 mL) and hexanes (10 mL) then slurried at ambient temperature for 30 minutes. Filtration provided 7-chloro-3-(2-chlorobenzyl)-3,4-dihydro-1H-benzo[e][1,4]diazepine-2,5-dione (2.4 g, 56%). $^1$H-NMR (300 MHz, DMSO-$d_6$) δ 2.97 (m, 1H), 3.23 (m, 1H), 4.00 (m, 1H), 7.12 (d, 1H, J=8.79 Hz), 7.27 (m, 2H), 7.40 (m, 2H), 7.58 (dd, 1H, J1=8.79 Hz, J2=2.64 Hz), 7.67 (d, 1H, J=2.64 Hz), 8.73 (d, 1H, J=6.15 Hz), 10.59 (s, 1H); ESI m/z 335.0, 337.0.

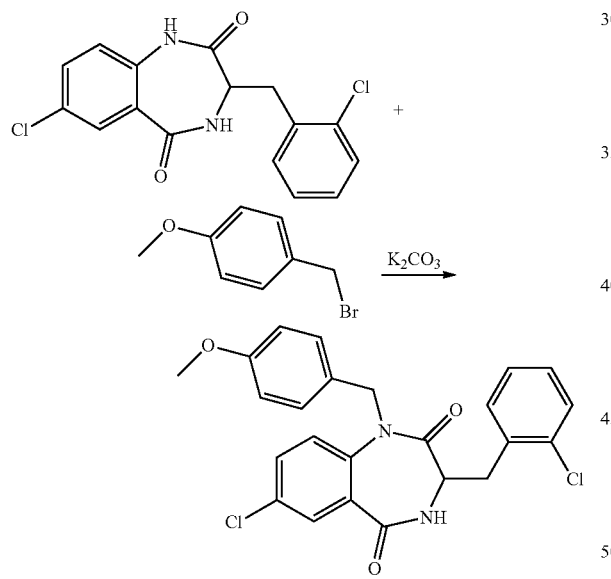

7-Chloro-3-(2-chlorobenzyl)-1-(4-methoxybenzyl)-3,4-dihydro-1H-benzo[e][1,4]diazepine-2,5-dione. 7-Chloro-3-(2-chlorobenzyl)-3,4-dihydro-1H-benzo[e][1,4]diazepine-2,5-dione (0.8 g, 2.39 mmol), powdered potassium carbonate (0.495 g, 3.58 mmol) and 4-methoxybenzyl chloride (0.39 mL, 2.86 mmol) were suspended in N,N-dimethylformamide (20 mL) and stirred at ambient temperature overnight. The solution was poured into water (100 mL) and ethyl acetate (150 mL). The layers were separated and the organic layer was washed with water (2×100 mL) then brine, and dried with sodium sulfate, decanted and concentrated in the presence of silica gel. The product was purified by column chromatography eluting with a gradient of 0-50% ethyl acetate in hexanes to yield 7-chloro-3-(2-chlorobenzyl)-1-(4-methoxybenzyl)-3,4-dihydro-1H-benzo[e][1,4]diazepine-2,5-dione (0.65 g, 60%). $^1$H NMR (300 MHz, DMSO-$d_6$) δ 3.06 (m, 1H), 3.30 (m, 2H), 3.66 (s, 3H), 4.13 (m, 1H), 4.82 (d, 1H), 5.34 (d, 1H), 6.76 (d, 2H, J=8.79 Hz), 6.96 (d, 2H, J=8.79 Hz), 7.21-29 (m, 2H), 7.36-45 (m, 2H), 7.54-7.61 (m, 3H), 8.97 (d, 1H, J=5.86 Hz); ESI m/z 455.1.

Example 3

Representative General Procedures for Synthesis of (E)-5,7-Dichloro-benzodiazepin-2(3H)-one Intermediate

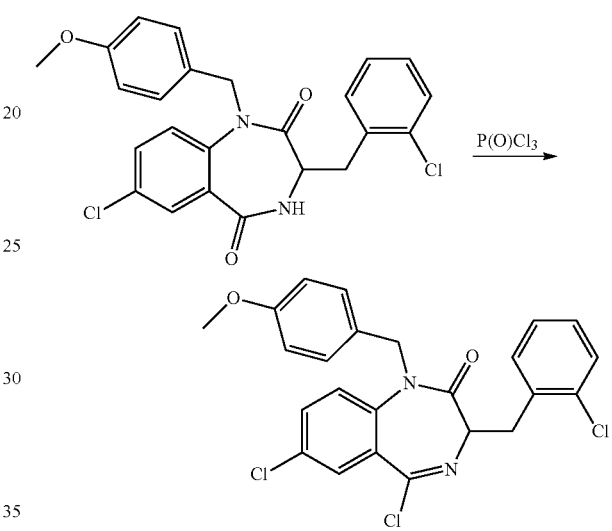

(E)-5,7-Dichloro-3-(2-chlorobenzyl)-1-(4-methoxybenzyl)-1H-benzo[e][1,4]diazepin-2(3H)-one. 7-Chloro-3-(2-chlorobenzyl)-1-(4-methoxybenzyl)-3,4-dihydro-1H-benzo[e][1,4]diazepine-2,5-dione (0.65 g, 1.43 mmol) was suspended in anhydrous toluene (10 mL) under a nitrogen atmosphere. N,N-Dimethylaniline (0.36 mL, 2.9 mmol) was added followed by phosphorus oxychloride (0.20 mL, 2.1 mmol) and the mixture was heated at 90° C. for 4 hours. After cooling to ambient temperature, the mixture was diluted with 40 mL of ethyl acetate:hexanes (1:2), washed with ice water (10 mL), ice cold 1 M hydrogen chloride (2×10 mL), and brine, then dried with sodium sulfate, decanted and concentrated in vacuo. The residue was redissolved in a small amount of ethyl acetate, then poured onto a silica plug. The product was eluted with 100 mL of ethyl acetate:hexanes (1:2) to yield (E)-5,7-dichloro-3-(2-chlorobenzyl)-1-(4-methoxybenzyl)-1H-benzo[e][1,4]diazepin-2(3H)-one (680 mg, 100%) which was used without further purification.

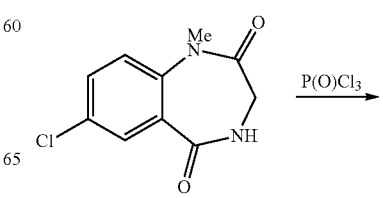

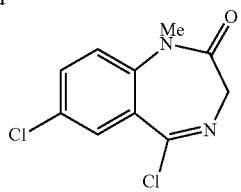

(E)-5,7-Dichloro-1-methyl-1H-benzo[e][1,4]diazepin-2(3H)-one (Compound D where R=Me). In a 1 L 2 neck RBF equipped with mechanical stir, condenser and N₂ inlet, 7-chloro-1-methyl-3,4-dihydro-1H-benzo[e][1,4]diazepine-2,5-dione (42.5 g, 0.189 mol) was suspended into 400 ml, of toluene. To this was added N,N-dimethylanaline (45.5 g. 0.375 mol) followed by the addition of POCl₃ (29 g, 0.189 mol) and the reaction mixture stirred for 3 min (RT). Reaction flask was placed in a 90° C. oil bath and the reaction mixture stirred/heated for 7 h and then at RT for 9 h. Reaction was quenched by adding 500 mL of ice water and stirred for 15 min. Organic layer was separated and quickly washed with cold 0.5 M HCl (300 mL), cold water (300 mL), and then cold saturated NaHCO₃ (300 mL). Organic layer was dried (MgSO₄), filtered and concentrated on a rotary evaporator to give 40 g of yellow solid. Yield 87.5%. ¹H NMR (300 MHz, DMSO-d₆) δ 3.25 (s, 3H), 3.8-3.9 (s, 1H, br), 4.3-4.4 (s, 1H, br), 7.4 (d, 1H), 7.7-7.8 (m, 2H).

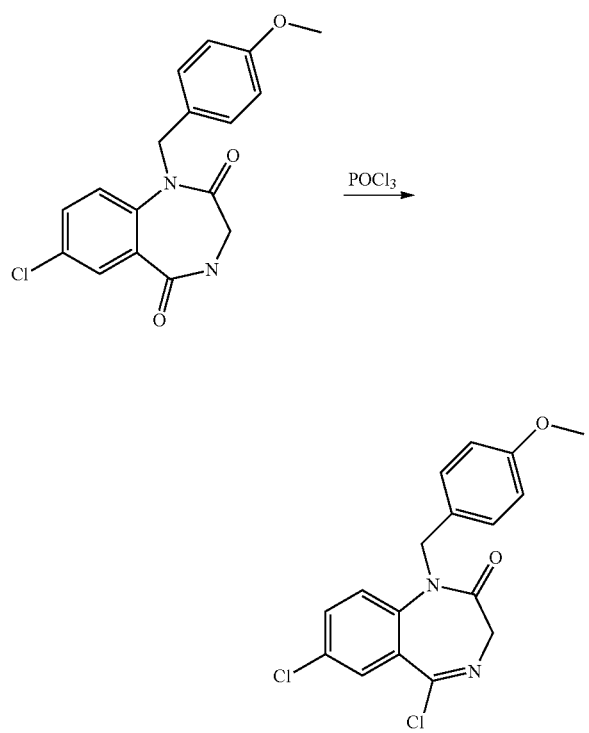

(E)-5,7-Dichloro-1-(4-methoxybenzyl)-1H-benzo[e][1,4]diazepin-2(3H)-one. In a 1 L 3 neck RBF equipped with magnetic stir bar, condenser and N₂ inlet, 7-chloro-1-(4-methoxybenzyl)-3,4-dihydro-1H-benzo[e][1,4]diazepine-2,5-dione (45 g, 0.136 mol) was suspended in 400 mL of toluene. To this was added N,N-dimethylanaline (33 g, 0.272 mol) followed by the addition of POCl₃ (23 g) and the reaction stirred for 3 min (RT). Reaction flask was placed into a 90° C. oil bath and the reaction mixture was heated for 5 h and then cooled. The reaction was quenched by adding 450 mL of ice water and stirred for 15 min. The organic layer was separated and quickly washed with cold water (2×250 mL) and brine (300 mL). Then, the organic layer was dried over MgSO₄, filtered and concentrated on a rotary evaporator to give 57 g of black crude product. Crude product was used for next step with no further purification. Yield 87.5%.

Example 4

Representative General Procedure for Installation of C3-Substituents on (E)-5,7-Dichloro-benzodiazepin-2(3H)-one Intermediates

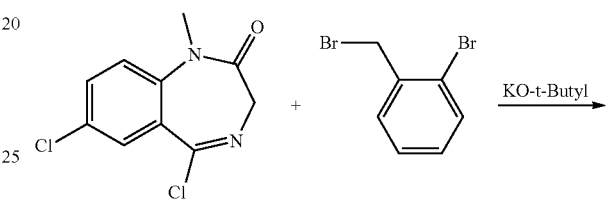

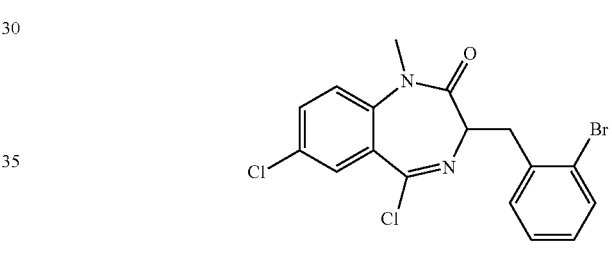

(E)-3-(2-bromobenzyl)-5,7-dichloro-1-methyl-1H-benzo[e][1,4]diazepin-2(3H)-one. (E)-5,7-Dichloro-1-methyl-1H-benzo[e][1,4]diazepin-2(3H)-one (400 mg, 1.65 mmol) was dissolved in anhydrous tetrahydrofuran (5 mL) under a nitrogen atmosphere, cooled to −78° C., then a 1 M solution of potassium tert-butoxide in tetrahydrofuran (1.7 mL, 1.7 mmol) was added dropwise. The reaction mixture was stirred for 10 minutes before a solution of the 2-bromobenzyl bromide (411 mg, 1.65 mmol) in tetrahydrofuran (2 mL) was added dropwise. The mixture was stirred at −78° C. for 20 minutes then the cooling bath removed and the mixture was allowed to warm to ambient temperature and stirred at ambient temperature for 18 hours. Piperazine (283 mg, 3.29 mmol) was added to remove excess 2-bromobenzyl bromide and the mixture was stirred at ambient temperature for 30 minutes, diluted with ethyl acetate, and washed with cold 1 M aqueous hydrogen chloride (2×40 mL). The organic layers were dried with sodium sulfate, decanted and concentrated in vacuo to approximately 20 mL of a red liquid. The product was purified on a short pad of silica gel eluting with 100 mL of ethyl acetate:hexanes (1:2) to yield (E)-3-(2-bromobenzyl)-5,7-dichloro-1-methyl-1H-benzo[e][1,4]diazepin-2(3H)-one (0.44 g, 65%). ¹H NMR (300 MHz, CDCl₃) δ 3.40 (s, 3H) 3.75 (m, 2H), 4.15 (m, 1H), 7.05-7.55 (m, 7H).

Example 5

Representative General Procedure for Synthesis of C5-Arylurea Compounds from (E)-5,7-Dichloro-benzodiazepin-2(3H)-one Intermediates Method A:
Part I: Installation of C-5 Aryl Substituent.

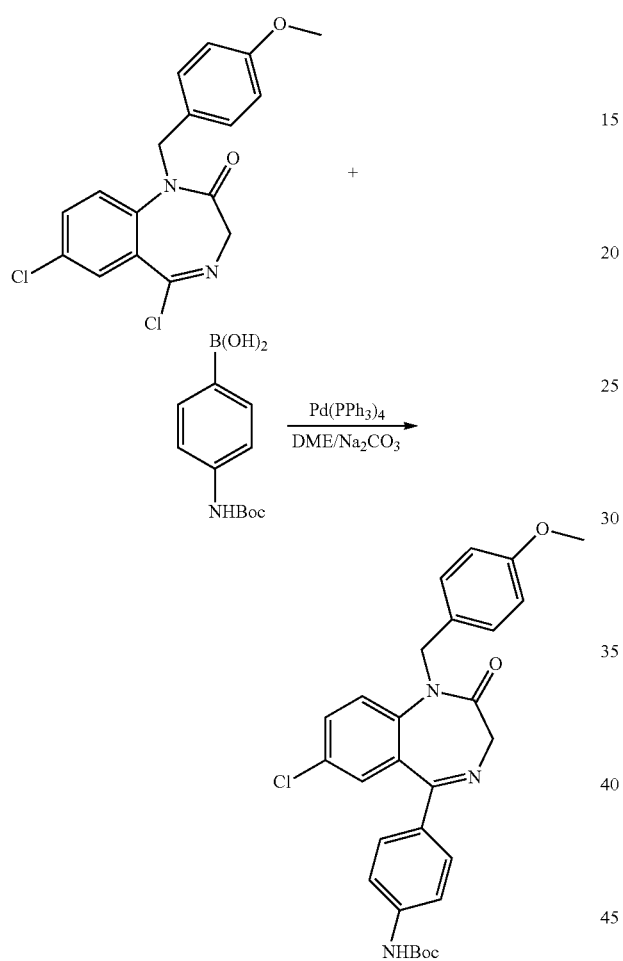

(Z)-tert-Butyl-4-(7-chloro-1-(4-methoxybenzyl)-2-oxo-2,3-dihydro-1H-benzo[e][1,4]diazepin-5-yl)phenylcarbamate. Imidoyl chloride (5.5 g, 15.7 mmol) was treated with (4-tert-butoxycarbonylaminophenyl)boronic acid (3.72 g, 18.84 mmol), Pd(PPh$_3$)$_4$ (0.362 g, 0.314 mmol), 2N aqueous Na$_2$CO$_3$ (23.5 mL), and DME (2.5 mL), degassed with nitrogen and heated at 80° C. for 3 h. The reaction mixture was cooled, diluted with EtOAc (200 mL) and poured into water (200 mL). The layers were separated and the aqueous was extracted with EtOAc (100 mL). The combined extracts were washed with brine (200 mL), dried over MgSO$_4$, and evaporated to dryness. The crude material was purified by flash column chromatography (eluted with 20% EtOAc in Hexane) to give (Z)-tert-butyl 4-(7-chloro-1-(4-methoxybenzyl)-2-oxo-2,3-dihydro-1H-benzo[e][1,4]diazepin-5-yl)phenylcarbamate (3.4 g, 42.8%) as a pale solid. $^1$H NMR (400 MHz, CDCl$_3$) δ 1.55 (s, 9H), 3.73 (s, 3H), 3.83 (d, 1H), 4.63 (d, 1H), 4.86 (d, 1H), 5.59 (d, 1H), 6.63 (d, 2H), 6.66 (d, 2H), 6.93 (d, 2H), 7.17 (s, 1H), 7.28 (s, 2H), 7.32-7.41 (m, 6H). MS m/z 507.3 [M+1]

Part II: Installation of C3-Substituent.

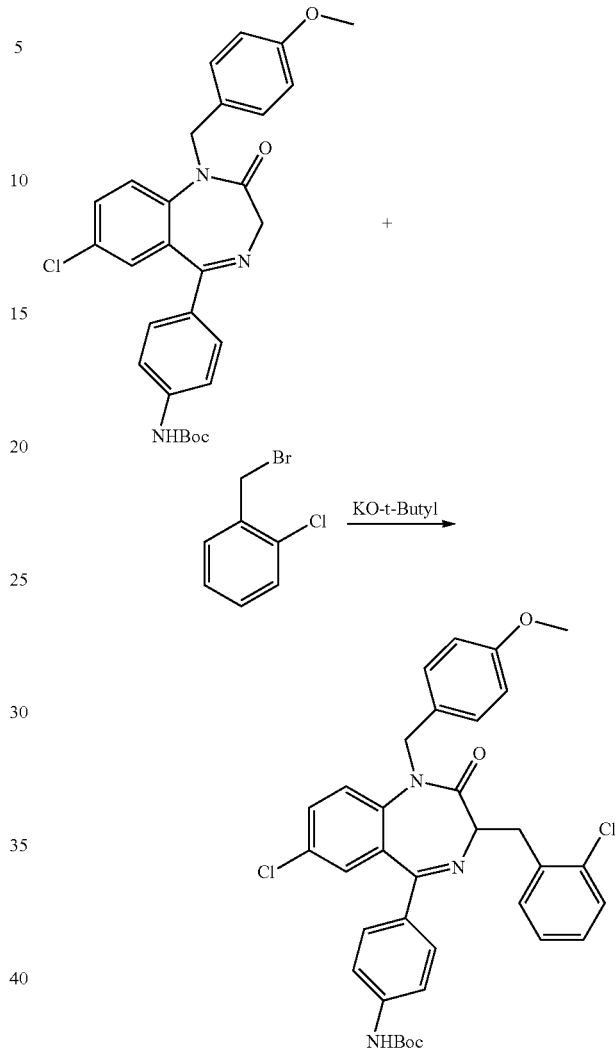

(Z)-tent-Butyl 7-chloro-3-(2-chlorobenzyl)-1-(4-methoxybenzyl)-1H-benzo[e][1,4]diazepin-5-yl)phenylcarbamate. To a solution of (Z)-tert-butyl 4-(7-chloro-1-(4-methoxybenzyl)-2-oxo-2,3-dihydro-1H-benzo[e][1,4]diazepin-5-yl) phenylcarbamate (2 g, 3.95 mmol), was added at −78° C. under a N$_2$ atmosphere, a solution of potassium tert-butoxide (1 M in THF, 7.9 mL, 7.9 mmol). After completion of the addition the reaction mixture was stirred for ½ h at −78° C. and a solution of 2-chlorobenzylbromide (0.570 mL, 4.34 mmol) in THF (10 mL) was added at −78° C. drop-wise over 15 minutes. The reaction mixture was stirred at −78° C. for 2 more hours and then the temperature was raised to room temperature. The reaction mixture was left at room temperature overnight under a N$_2$ atmosphere. The reaction mixture was quenched with water (50 mL) and extracted with EtOAc (3×50 mL). The combined extracts were washed with brine (100 mL), dried (MgSO$_4$) and evaporated in vacuo. The crude material was purified by flash column chromatography (eluted with 20% EtOAc in Hexane) to give (Z)-tert-butyl 7-chloro-3-(2-chlorobenzyl)-1-(4-methoxybenzyl)-1H-benzo[e][1,4]diazepin-5-yl)phenylcarbamate (0.78 g, 31.3%) as a pale cream solid. $^1$H NMR (400 MHz, DMSO-d$_6$) δ 1.49 (s, 9H), 3.32 (s, 3H), 3.55 (d, 2H), 3.59 (s, 3H) 3.90 (t, 1H), 4.78 (d, 1H), 5.47 (d, 1H), 6.64 (d, 2H), 6.82 (d, 2H), 7.06 (d, 2H), 7.10 (s, 1H), 7.21-7.30 (m, 3H), 7.32-7.62 (m, 3H), 7.64 (d, 1H), 7.75 (d, 1H), 9.61 (s, 1H). MS m/z 631.36 [M+1].

Part III: Removal of p-Methoxybenzyl group.

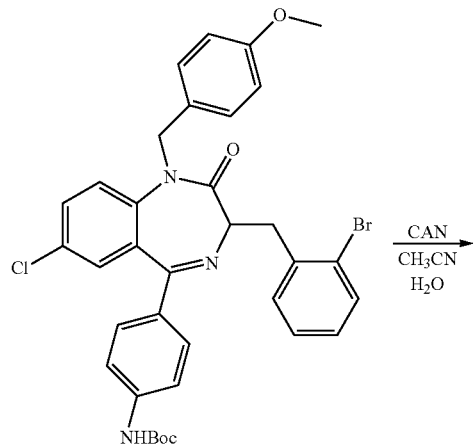

(Z)-tert-Butyl 4-(3-(2-bromobenzyl)-7-chloro-2-oxo-2,3-dihydro-1H-benzo[e][1,4]diazepin-5-yl)phenylcarbamate. To a solution of (Z)-tert-butyl 7-chloro-3-(2-bromobenzyl)-1-(4-methoxybenzyl)-1H-benzo[e][1,4]diazepin-5-yl)phenylcarbamate (7.07 g, 10.47 mmol) in a mixture of CH$_3$CN/H$_2$O (250/83 mL) was added Cerium (IV) Ammonium Nitrate (45.9 g, 83.76 mmol) portion-wise at −15° C. The reaction mixture was stirred at −15° C. for 1 h, the temperature was raised to room temperature and the mixture left at room temperature for 2 h. The reaction mixture was then diluted with water (200 ml) and EtOAc (200 mL). The organic layer was separated and the aqueous layer was extracted with EtOAc (2×200 mL). The combined extracts were washed with brine (100 mL), dried (MgSO$_4$) and evaporated in vacuo. The crude material was purified by flash column chromatography (eluted with 40% EtOAc in Hexane) to give (Z)-tert-butyl 4-(3-(2-bromobenzyl)-7-chloro-2-oxo-2,3-dihydro-1H-benzo[e][1,4]diazepin-5-yl)phenylcarbamate (3.3 g, 56.8%) as a pale solid. MS m/z 555.25 [M+1].

Part IV: Removal of Boc Protecting Group.

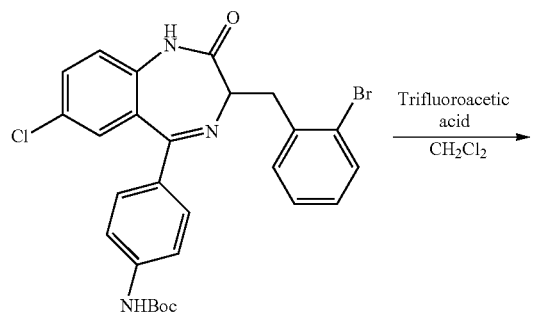

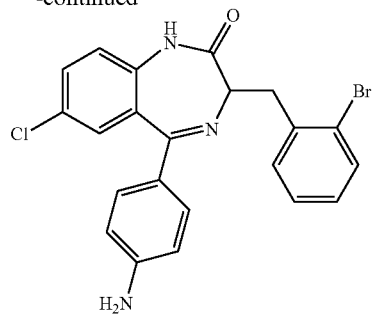

(Z)-5-(4-Aminophenyl)-3-(2-bromobenzyl)-7-chloro-1H-benzo[e][1,4]diazepin-2(3H)-one. To a solution of (Z)-tert-butyl 4-(3-(2-bromobenzyl)-7-chloro-2-oxo-2,3-dihydro-1H-benzo[e][1,4]diazepin-5-yl)phenylcarbamate (3.3 g, 5.94 mmol) in dichloromethane (45 mL) was added dropwise at 0° C. trifluoroacetic acid (15 mL). After completion of the addition, the reaction mixture was stirred at 0° C. for 1 h then the temperature was raised to room temperature and kept at room temperature for 4 h. The reaction mixture was cooled down to 0° C. and treated with a solution of 10% NaOH in water until a pH >10 was obtained. The two layers were separated. The aqueous layer was extracted with dichloromethane (2×50 mL). The combined extracts were washed with brine (100 mL), dried (MgSO$_4$) and evaporated in vacuo. The crude material was purified by flash column chromatography (eluted with 40% EtOAc in Hexane) to give (Z)-5-(4-aminophenyl)-3-(2-bromobenzyl)-7-chloro-1H-benzo[e][1,4] diazepin-2(3H)-one (2.35 g, 87%) as a pale yellow solid. $^1$H NMR (400 MHz, DMSO-d$_6$) δ 3.45 (d, 2H), 3.71 (t, 1H), 5.62 (s, 2H), 6.53 (d, 2H), 7.10-7.17 (m, 3H), 7.22-7.25 (m, 2H), 7.33 (t, 1H), 7.46-7.61 (m, 3H), 10.64 (s, 1H). MS, m/z 455.19 [M+1].

Part V: Installation of Urea from C5-Aminoaryl Intermediate.

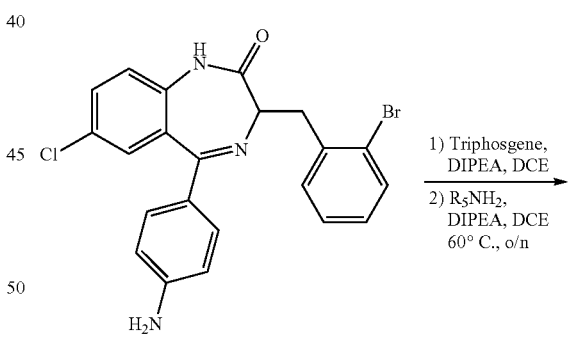

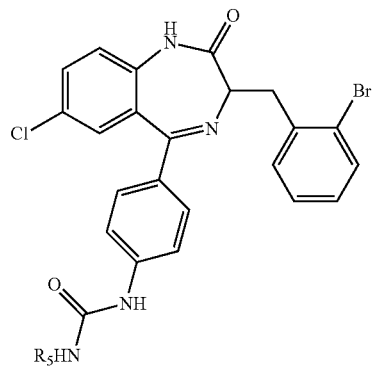

To a solution of triphosgene (0.023 mg, 0.078 mmol) in 1,2-dichloroethane (1 mL) was added a solution of (Z)-5-(4-aminophenyl)-3-(2-bromobenzyl)-7-chloro-1H-benzo[e][1,4]diazepin-2(3H)-one (0.08 g, 0.195 mmol), diisopropylethylamine (0.051 mL, 0.2925 mmol) in dichloroethane (1 mL). The reaction mixture was stirred at room temperature in a capped 7 mL glass vial for 10 minutes and then treated with a solution of amine ($R_5NH_2$, 0.468 mmol), diisopropylethylamine (0.051 mL, 0.2925 mmol) in 1,2-dichloroethane (1 mL). The reaction mixture was then heated at 60° C. for 12 h. The reaction mixture was then evaporated to dryness and individual samples were purified by automated high performance liquid chromatography.
Method B:
Part I:

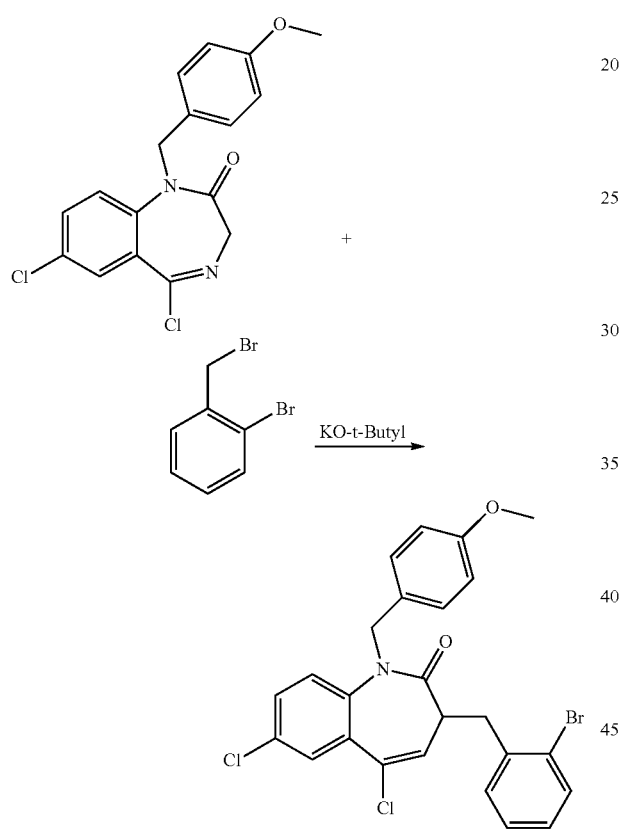

(E)-3-(2-Bromobenzyl)-5,7-dichloro-1-(4-methoxybenzyl)-1H-benzo[b]azepin-2(3H)-one. To a solution of (E)-5,7-dichloro-1-(4-methoxybenzyl)-1H-benzo[e][1,4]diazepin-2(3H)-one (0.45 g, 1.28 mmol) in anhydrous THF (20 mL), was added at −78° C. under a N2 atmosphere, a solution of potassium tert-butoxide (1 M in THF, 1.54 mL, 1.54 mmol). After completion of the addition the reaction mixture was stirred for ½ h at −78° C. and a solution of 2-bromobenzyl-bromide (0.386 mL, 1.54 mmol) in THF (5 mL) was added at −78° C. drop-wise over 15 minutes. The reaction mixture was stirred at −78° C. for 2 more hours and then the temperature was raised to room temperature. The reaction mixture was left at room temperature overnight under a $N_2$ atmosphere. The reaction mixture was quenched with saturated $NH_4Cl$ (50 mL) and extracted with EtOAc (3×50 mL). The combined extracts were washed with brine (100 mL), dried ($MgSO_4$) and evaporated in vacuo. The crude material was purified by flash column chromatography (eluted with 20% EtOAc in Hexane) to give (E)-3-(2-bromobenzyl)-5,7-dichloro-1-(4-methoxybenzyl)-1H-benzo[b]azepin-2(3H)-one (0.49 g, 74%) as a pale solid. $^1$H NMR (400 MHz, DMSO-$d_6$) δ 3.65 (s, 3H), 4.06-4.10 (m, 2H), 4.86 (d, 1H), 5.39 (d, 1H), 4.79 (d, 2H), 6.92 (d, 2H), 7.12-7.39 (m, 3H), 7.54-7.56 (m, 1H), 7.67-7.82 (m, 3H). MS m/z 519.20 [M+1].
Part II:

It is contemplated that an urea aryl boronate ester may be coupled to a 5,7-dichloro-benzo[b]azepin-2(3H)-one using a palladium coupling reaction, as illustrated below.

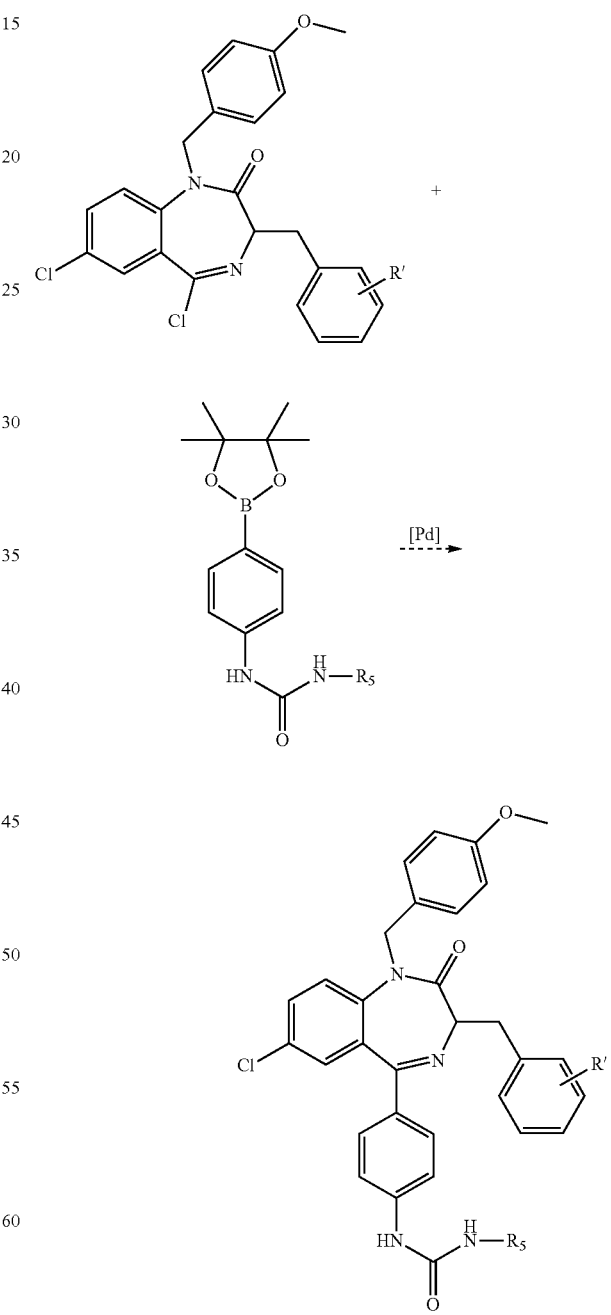

R' is H, chloride, or alkyl
$R_5$ is optionally substituted alkyl

A variety of urea aryl boronate esters can be prepared using the procedures illustrated below.

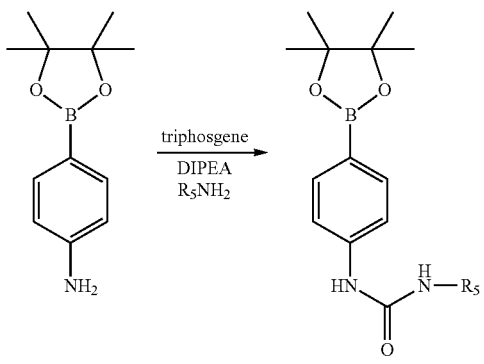

R₅ = methyl or isopropyl

General Procedure for the Synthesis of Ureas. Triphosgene (0.3 eq) was dissolved in anhydrous dichloromethane (20% v/v) in a dry flask under nitrogen. The amino boronate ester (1 eq) was dissolved in dichloromethane (20% v/v) and to it was added diisopropylethylamine (1 eq). This mixture was added dropwise over a 1 h period to the stirred triphosgene solution. After stirring for a further 5 minutes the primary amine (1 eq, R₅NH₂) was added in one portion, followed immediately by diisopropylethylamine (1 eq). The mixture was then stirred overnight. Water (20% v/v) was added and the mixture was stirred for 5 minutes. The aqueous layer was removed and more water was added. Purification of individual products involved either precipitation from water, or an extraction into organic solvent. In some cases further purification by chromatography was necessary. Yields were typically 70-80%.

Example 6

Representative General Procedure for Synthesis of C5-Alkoxyaryl Compounds from (E)-5,7-Dichloro-benzodiazepin-2(3H)-one Intermediates

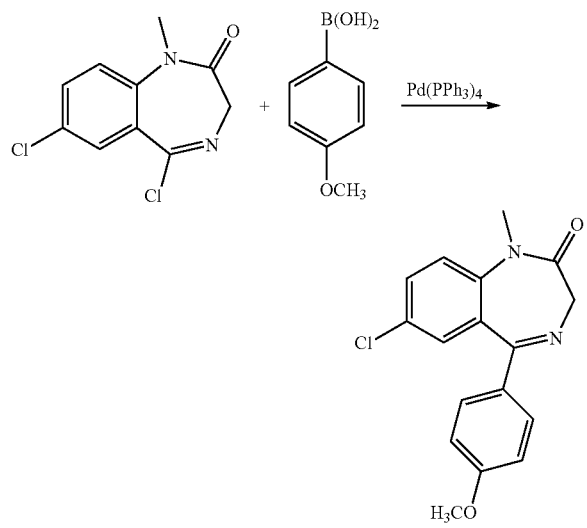

(Z)-7-Chloro-5-(4-methoxyphenyl)-1-methyl-1H-benzo[e][1,4]diazepin-2(3H)-one. In a 1 L 3-neck RBF equipped with magnetic stir bar, condenser, thermocouple, and N₂ inlet, crude (E)-5,7-dichloro-1-methyl-1H-benzo[e][1,4]diazepin-2(3H)-one (30 g, 0.124 mol) was dissolved into 300 mL of DME. To this was added a solution of Na₂CO₃ (21 g, 0.2 mol in 200 mL of H₂O) followed by addition of 4-methoxyphenyl boronic acid (22 g, 0.145 mol) and Pd(PPh₃)₄ (1.2 g, 8.3 mmol). The reaction mixture was heated in a 85° C. oil bath, under N₂, for 2 h and then cool to room temp. To this was added 200 mL of EtOAc and the mixture stirred for 5 min. The organic layer was separated and washed with H₂O (200 mL) and brine (200 mL). Organic layer was dried over MgSO₄ and then concentrated to dryness to give 53 g of crude product. This was subjected to silica chromatography using 210 g of silica gel and EtOAc/hepatene (12:88 to 30:70 to 50:50 to 70:30; total of 8 L mobile phase). Fractions containing pure product were combined and concentrated to dryness to give 42.7 g of pure product (quantitative). ¹H NMR (300 MHz, CDCl₃) δ 3.38 (s, 3H), 3.73 (d, 1H), 3.85 (s, 3H), 4.75 (d, 1H), 6.9 (m, 2H), 7.31 (m, 2H), 7.48-7.58 (m, 3H).

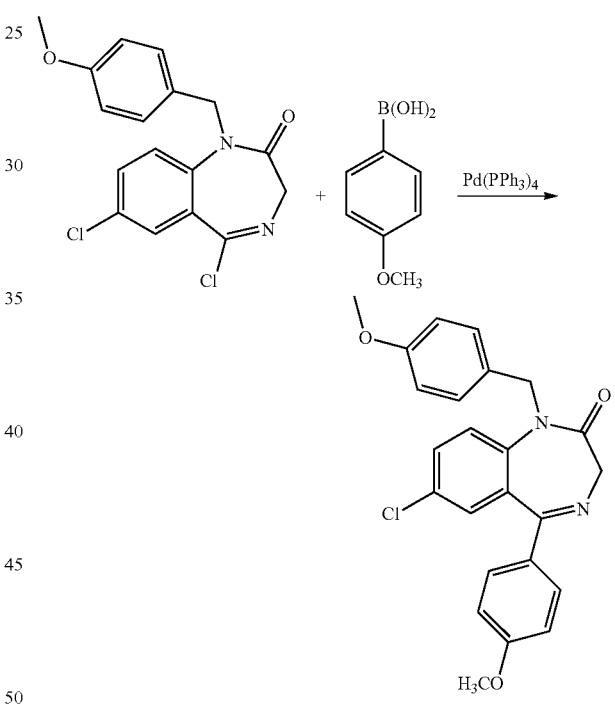

(Z)-7-Chloro-1-(4-methoxybenzyl)-5-(4-methoxyphenyl)-1H-benzo[e][1,4]diazepin-2(3H)-one. In a 1 L 3 neck RBF equipped with magnetic stir bar, condenser, thermocouple, and N₂ inlet, crude (E)-5,7-dichloro-1-(4-methoxybenzyl)-1H-benzo[e][1,4]diazepin-2(3H)-one (54 g) was dissolved into 360 mL of DME. To this was added a solution of Na₂CO₃ (23 g, 0.15 mol, in 250 ml, of H₂O) followed by the addition of 4-methoxyphenyl boronic acid (22.7 g, 0.15 mol) and Pd(PPh₃)₄ (1.4 g, 1.2 mmol). The reaction mixture was heated in a 85° C. oil bath for 2 h and then cooled (RT). To this was added 200 mL of EtOAc and the mixture stirred for 5 min. Organic layer was separated and washed with 200 mL H₂O and then brine. Organic layer was concentrated to dryness to give 68 g of crude product. This was subjected to column chromatography using 550 g of silica gel and 25/75 to 60/40 EtOAc/heptane. Fractions containing pure product were combined to give 21 g of pure product and other fractions containing a small amount of impurity (by TLC) gave another 20 g of product, albeit less pure. However NMR of both lots was identical. Total of 41 g of product was obtained. Yield 72% over two steps. $^1$H NMR (300 MHz, CDCl$_3$) δ 3.7 (s, 3H), 3.80 (d, 1H), 3.85 (s, 3H), 4.57 (d, 1H), 4.85 (d, 1H), 5.57 (d, 1H), 6.63 (d, 2H), 6.85-6.95 (m, 4H), 7.16 (d, 1H), 7.3-7.44 (m, 4H).

Example 7

Representative General Procedures for Installation of a C3-Substituent onto C5-Aryl-benzo[e][1,4]diazepin-2(3H)-ones

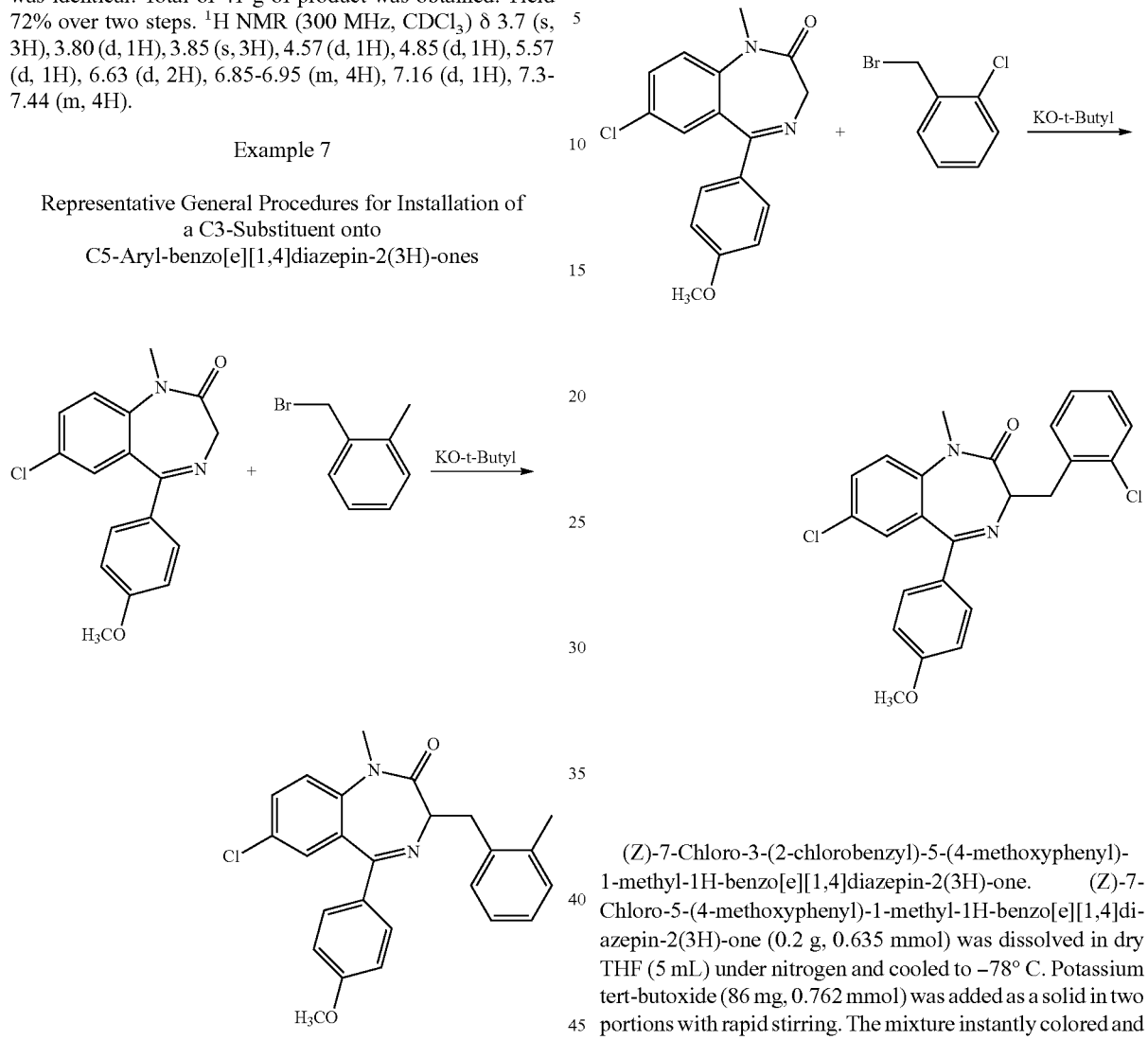

(Z)-7-Chloro-5-(4-methoxyphenyl)-1-methyl-3-(2-methylbenzyl)-1H-benzo[e][1,4]diazepin-2(3H)-one. To a stirred and cooled (dry ice/acetone bath) solution of (Z)-7-chloro-5-(4-methoxyphenyl)-1-methyl-1H-benzo[e][1,4]diazepin-2(3H)-one (0.50 g, 1.59 mmol) in THF (8 mL) was slowly added 1 M KO$^t$Bu (2.4 mL, 2.4 mmol, 1.5 eq). The resulting deep red mixture was stirred over dry ice/acetone bath ~10 min followed by the slow addition of a solution of 2-methylbenzyl bromide (0.46 g, 2.5 mmol, 1.5 eq) in THF (2 mL). After stirring another ~35 min at −78° C., the reaction mixture was quenched with water and diluted with EtOAc. The organic layer was dried (Na$_2$SO$_4$), filtered and evaporated (rotovap, then high vacuum). Chromatography over silica gel using 20-40% EtOAc/heptane gave 0.56 g (yield of 84%) of the title product [Note: when using benzyl chlorides as alkylating agents, tetrabutyl ammonium iodide was added along with the alkylating agent at the low temperature]. $^1$H NMR (300 MHz, CDCl$_3$) δ 2.38 (s, 3H), 3.41 (s, 3H), 3.5-3.65 (m, 2H), 3.74 (dd, 1H), 3.84 (s, 3H), 6.89 (dt, 2 H), 7.05-7.15 (m, 3H), 7.25-7.35 (m, 3H), 7.45-7.5 (m, 3H).

(Z)-7-Chloro-3-(2-chlorobenzyl)-5-(4-methoxyphenyl)-1-methyl-1H-benzo[e][1,4]diazepin-2(3H)-one. (Z)-7-Chloro-5-(4-methoxyphenyl)-1-methyl-1H-benzo[e][1,4]diazepin-2(3H)-one (0.2 g, 0.635 mmol) was dissolved in dry THF (5 mL) under nitrogen and cooled to −78° C. Potassium tert-butoxide (86 mg, 0.762 mmol) was added as a solid in two portions with rapid stirring. The mixture instantly colored and rapidly turned deep red. After 5 min, 2-chlorobenzyl bromide (107 µL, 0.836 mmol) was added dropwise by syringe. The mixture was allowed to stir at −78° C. for 1 h under nitrogen. It turned a light brown color. TLC (1:1 hexanes:ethyl acetate) indicated no starting material remained with a major less polar product and a minor more polar product plus some residual 2-chlorobenzylbromide. The reaction was quenched cold by adding ~2 mL 1:1 methanol:water. A yellow precipitate formed. The cold bath was removed and the mixture was allowed to warm to room temperature. Water and ethyl acetate were added. The organic layer was separated and washed one time with brine then dried over magnesium sulfate, filtered and the solvent evaporated. Chromatography on a 10 g silica gel eluting with a gradient of 30-50% ethyl acetate in hexanes gave (Z)-7-chloro-3-(2-chlorobenzyl)-5-(4-methoxyphenyl)-1-methyl-1H-benzo[e][1,4]diazepin-2(3H)-one as a yellow oil (232 mg, 0.528 mmol, 83%). $^1$H NMR (300 MHz, CDCl$_3$) δ 3.37 (s, 3H), 3.6-3.75 (m, 2H), 3.79-3.86 (m, 1H), 3.81 (s, 3H), 6.85 (d, J=9 Hz, 2H), 7.1-7.6 (m, 9H); ESI m/z 439.6 [M+H$^+$].

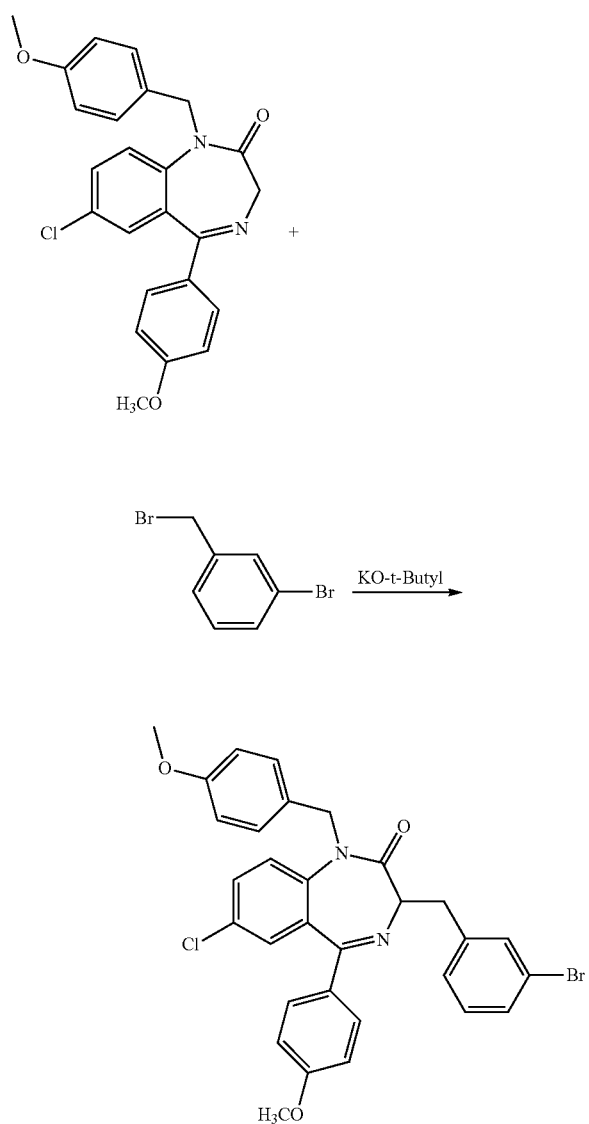

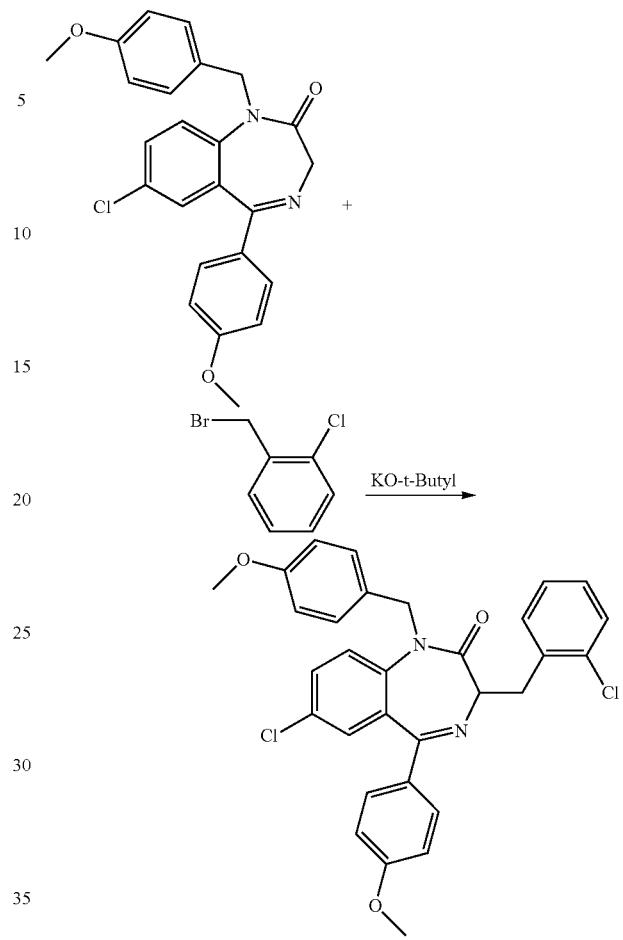

(Z)-3-(3-Bromobenzyl)-1-(4-methoxybenzyl)-7-chloro-5-(4-methoxyphenyl)-1H-benzo[e][1,4]-diazepin-2(3H)-one. To a stirred and cooled (dry ice/acetone bath) solution of (Z)-7-chloro-1-(4-methoxybenzyl)-5-(4-methoxyphenyl)-1H-benzo[e][1,4]diazepin-2(3H)-one (6.00 g, 14.2 mmol) in THF (80 mL) was slowly added 1 M KO$^t$Bu (21 mL, 21 mmol, 1.5 eq). The resulting deep red mixture was stirred over dry ice/acetone bath ~10 min followed by the slow addition of a solution of 3-bromobenzyl bromide (5.10 g, 21.4 mmol, 1.5 eq) in THF (15 mL). After stirring another ~45 min at −78° C., the reaction mixture was quenched with saturated brine and diluted with EtOAc. The organic layer was dried (Na$_2$SO$_4$), filtered and evaporated (rotovap, then high vacuum). Chromatography over silica gel using 10-30% EtOAc/heptane gave 7.08 g (yield of 84%) of the title product. [Note: when using benzyl chlorides as alkylating agents, tetrabutyl ammonium iodide was added along with the alkylating agent at the low temperature]. $^1$H NMR (300 MHz, CDCl$_3$) δ 3.57 (d, 2H), 3.70 (s, 3H), 3.73 (t, 1H), 3.83 (s, 3H), 4.59 (d, 1H), 5.62 (d, 1H), 6.61 (d, 2H), 6.8-6.9 (m, 4H), 7.2-7.45 (m, 8H), 7.63 (fine d, 1H).

(Z)-7-Chloro-3-(2-chlorobenzyl)-1-(4-methoxybenzyl)-5-(4-methoxyphenyl)-1H-benzo[e][1,4]diazepin-2(3H)-one. (Z)-7-Chloro-1-(4-methoxybenzyl)-5-(4-methoxyphenyl)-1H-benzo[e][1,4]diazepin-2(3H)-one (0.344 g, 0.817 mmol) was dissolved in dry THF (8 mL) and cooled to −78° C. under nitrogen. Potassium tert-butoxide (0.119 g, 1.063 mmol) was added in one portion. The reaction mixture was stirred for 5 min. turning deep red. 2-chlorobenzylbromide (0.128 mL, 0.981 mmol) was added by syringe. The mixture was stirred at −78° C. for 1.5 h then the cold bath was removed. After 1 h, the reaction was quenched with methanol and diluted with ethyl acetate. The organic layer was washed with water (2×) then brine and dried (MgSO$_4$). Chromatography on silica gel eluting with 25-30% ethyl acetate in hexanes gave (Z)-7-chloro-3-(2-chlorobenzyl)-1-(4-methoxybenzyl)-5-(4-methoxyphenyl)-1H-benzo[e][1,4]diazepin-2(3H)-one (128 mg, 29%). $^1$H NMR (300 MHz, CDCl$_3$) δ 3.6-3.8 (m, 2H), 3.7 (s, 3H), 3.8 (s, 3H), 3.9-4.0 (m, 1H), 4.55 (d, 1H), 5.7 (d, 1H), 6.6 (d, 2H), 6.8-6.9 (m, 4H), 7.1-7.4 (m, 8H), 7.6 (dd, 1H); ESI m/z.

The following compounds were prepared based on the above procedures:

(Z)-7-Chloro-5-(4-methoxyphenyl)-3-(3-bromobenzyl)-1-methyl-1H-benzo[e][1,4]diazepin-2(3H)-one. $^1$H NMR (300 MHz, CDCl$_3$) δ 3.40 (s, 3H), 3.45-3.55 (m, 2H), 3.67 (dd, 1H), 3.86 (s, 3H), 6.91 (d, 2H), 7.14 (t, 1H), 7.25-7.3 (m, 3H), 7.33 (ddd, 1H), 7.45-7.55 (m, 4H).

(Z)-7-Chloro-5-(4-methoxyphenyl)-3-(3-methylbenzyl)-1-methyl-1H-benzo[e][1,4]diazepin-2(3H)-one. $^1$H NMR (300 MHz, CDCl$_3$) δ 2.31 (s, 3H), 3.38 (s, 3H), 3.5-3.6 (m, 2H), 3.68 (dd, 1H), 3.82 (s, 3H), 6.88 (d, 2H), 6.99 (m, 1H), 7.1-7.2 (m, 3H), 7.2-7.3 (m, 3H+CHCl$_3$), 7.4-7.53 (m, 3H).

(Z)-7-Chloro-3-(3-isopropylbenzyl)-5-(4-methoxyphenyl)-1-methyl-1H-benzo[e][1,4]diazepin-2(3H)-one. $^1$H NMR (300 MHz, CDCl$_3$) δ 1.24/1.25 (2 overlapping doublets, 6H), 2.88 (heptet, 1H), 3.38 (s, 3H), 3.5-3.6 (m, 2H), 3.69 (t, 1H), 3.84 (s, 3H), 6.89 (d, 2H), 7.07 (dt, 1H), 7.13 (dt, 1H), 7.15-7.3 (m, 4H; includes CHCl$_3$ singlet), 7.47 (dd, 1H), 7.52 (d, 2H).

(Z)-3-(4-Isopropylbenzyl)-7-chloro-5-(4-methoxyphenyl)-1-methyl-1H-benzo[e][1,4]diazepin-2(3H)-one. $^1$H NMR (300 MHz, CDCl$_3$) δ 1.23 (d, 6H), 2.84 (septet, 1 H), 3.39 (s, 3H), 3.51 (m, 2H), 3.69 (dd, 1H), 3.85 (s, 1H), 6.89 (m, 2H), 7.12 (m, 2H), 7.26 (m, 4H), 7.44-7.54 (m, 3H).

(Z)-3-(4-Isopropylbenzyl)-7-chloro-1-(4-methoxybenzyl)-5-(4-hydroxyphenyl)-1H-benzo[e][1,4]diazepin-2(3H)-one. $^1$H NMR (300 MHz, DMSO-d$_6$) δ 1.15 (d, 6H), 2.85 (septet, 1H), 3.25-3.45 (m, 3H), 3.65 (s, 3H), 3.75-3.85 (m, 4H), 4.80 (d, 1H), 5.45 (d, 1H), 6.60 (m, 2H), 6.85 (m, 2H), 6.95 (m, 2H), 7.0-7.3 (m, 6H), 7.63 (dd, 1H), 7.74 (d, 1H).

Example 8

Representative General Procedure for Synthesis of C3-Alkylaralkyl Compounds from C3-Haloaralkyl Compounds

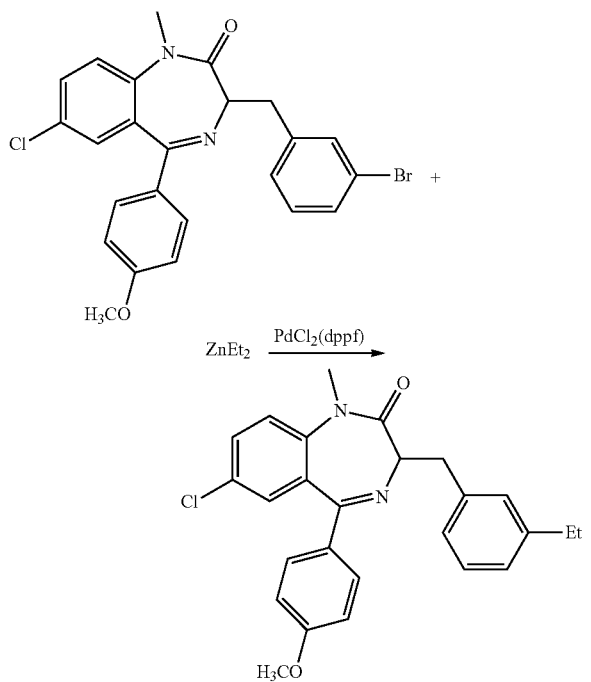

(Z)-7-Chloro-3-(3-ethylbenzyl)-5-(4-methoxyphenyl)-1-methyl-1H-benzo[e][1,4]diazepin-2(3H)-one. To a stirred and cooled (dry ice-acetone bath) solution of (Z)-3-(3-bromobenzyl)-7-chloro-5-(4-methoxyphenyl)-1-methyl-1H-benzo[e][1,4]diazepin-2(3H)-one (1.21 g, 2.5 mmol) and PdCl$_2$(dppf) [0.22 g] in dry THF (10 mL) was added 1 M Et$_2$Zn (9.3 mL, 10 mmol, 4 eq). After warming to RT, the reaction mixture was stirred at 50° C. until HPLC indicated reaction to be complete. After aqueous workup, chromatography gave 0.95 g (yield of 88%) of title product. $^1$H NMR (300 MHz, CDCl$_3$) δ 1.22 (t, 3H), 2.62 (q, 2H), 3.55 (d, 2H), 3.70 (t, 1H), 3.84 (s, 3H), 6.89 (d, 2H), 7.03 (m, 1H), 7.1-7.3 (m, 5H), 7.4-7.55 (m, 3H).

The following compound was prepared based on the above procedure:

(Z)-7-Chloro-3-(3-ethylbenzyl)-1-(4-methoxybenzyl)-5-(4-methoxyphenyl)-1H-benzo[e][1,4]diazepin-2(3H)-one. $^1$H NMR (300 MHz, CDCl$_3$) δ 1.23 (t, 3H), 2.63 (q, 2H), 3.55-3.65 (m, 2H), 3.68 (s, 3H), 3.80 (dd, 1H), 3.83 (s, 3H), 4.59 (d, 1H), 5.63 (d, 1H), 6.61 (d, 2H), 6.85 (d, 2H), 6.88 (d, 2H), 7.04 (dt, 1H), 7.10 (fine d, 1H), 7.13-7.26 (m, 5H), 7.30 (d, 1H), 7.37 (dd, 1H).

Example 9

Representative General Procedures for Deprotection of Amide Nitrogen Atom

Method A:

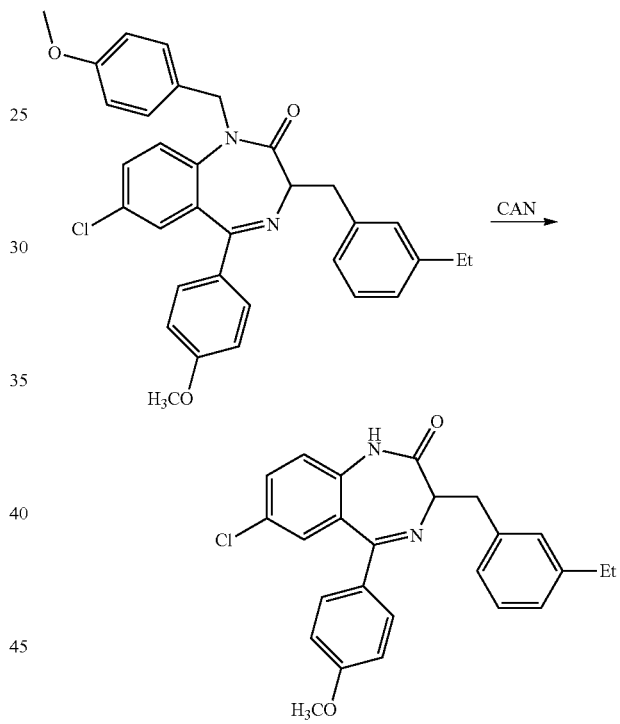

(Z)-3-(3-Ethylbenzyl)-7-chloro-5-(4-methoxyphenyl)-1H-benzo[e][1,4]diazepin-2(3H)-one. To a solution of PMB-protected benzodiazepinone (1 g) in MeCN (17 mL) and H$_2$O (3 mL) was added cerium(IV)ammonium nitrate (CAN) (7 g). The resulting mixture was stirred until TLC showed reaction to be complete and was then diluted with water, EtOAc and heptane. The organic layer was dried (Na$_2$SO$_4$), filtered and evaporated to a crude solid. Chromatography using increasing amounts of DCM/EtOAc (1:1) in heptane (up to 25:25:50 DCM/EtOAc/heptane) gave 0.55 g (yield of 57%) of the title product. $^1$H NMR (300 MHz, DMSO-d$_6$) δ 1.19 (t, 3H), 2.57 (q, 2H), 3.2-3.4 (m, 2H), 3.7-3.8 (m, 4H; contains OMe singlet at 3.79), 7.0-7.1 (m, 3H), 7.1-7.35 (m, 5H), 7.39 (d, 2H), 7.71 (dd, 1H), 10.9 (br s, 1H).

The following compound was prepared based on the above procedure:

(Z)-3-(4-Isopropylbenzyl)-7-chloro-5-(4-methoxyphenyl)-1H-benzo[e][1,4]diazepin-2(3H)-one. $^1$H NMR (300

MHz, DMSO-$d_6$) δ 1.15 (d, 6H), 2.85 (septet, 1H), 3.25-3.38 (m, 2H), 3.8 (br s, 4H), 6.95-7.50 (m, 10H), 7.73 (dd, 1H), 10.9 (s, 1H).
Method B:

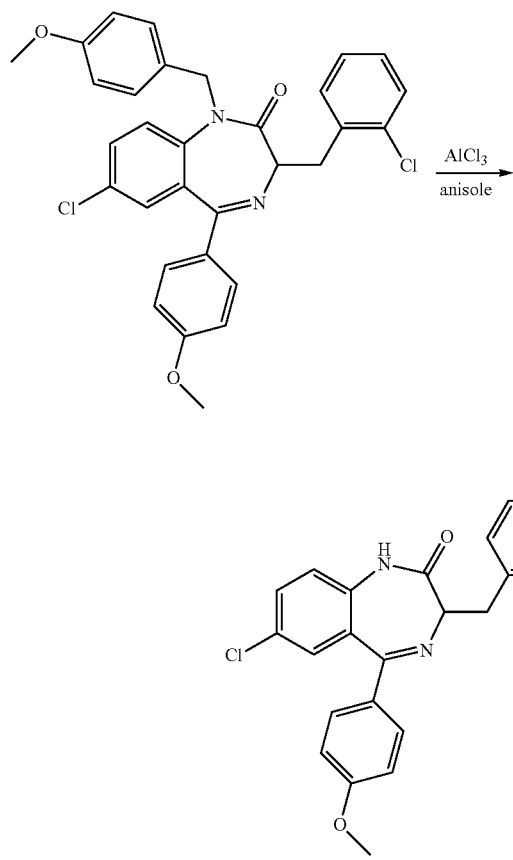

(Z)-7-Chloro-3-(2-chlorobenzyl)-5-(4-methoxyphenyl)-1H-benzo[e][1,4]diazepin-2(3H)-one. (Z)-7-Chloro-3-(2-chlorobenzyl)-5-(4-methoxyphenyl)-1-(4-methoxybenzyl)-1H-benzo[e][1,4]diazepin-2(3H)-one (128 mg, 0.235 mmol) was dissolved in anisole (1 mL) under nitrogen and $AlCl_3$ (125 mg, 0.939 mmol) was added in one portion. The resulting orange solution was heated to 85° C. for 2 h. After the mixture was cooled to room temperature, ice and ethyl acetate were added and the mixture was stirred for 30 min. The layers were partitioned and the organic layer was washed with water then brine. The combined aqueous layers were back-extracted with ethyl acetate and the combined organic layers were dried ($MgSO_4$), filtered and evaporated. The residue was chromatographed on silica gel, eluting with 5%, then 30% ethyl acetate in hexanes to give (Z)-7-chloro-3-(2-chlorobenzyl)-5-(4-methoxyphenyl)-1H-benzo[e][1,4]diazepin-2(3H)-one as a white solid (99 mg, 99%). $^1$H NMR (300 MHz, $CDCl_3$) δ 3.60-3.77 (m, 2H), 3.84 (s, 3H), 3.84-3.86 (m, 1H), 6.88 (dd, J=7, 2 Hz, 2H), 7.08 (d, J=9 Hz, 1H), 7.15-7.33 (m, 3H), 7.38 (dd, J=7, 2 Hz, 2H), 7.45 (dd, J=9, 2 Hz, 1H), 7.60 (dd, J=8, 2 Hz, 1H), 8.59 (s, 1H); ESI m/z 425.1.

Example 10

Representative General Procedures for Removal of a Methoxy Protecting Group

Method A:

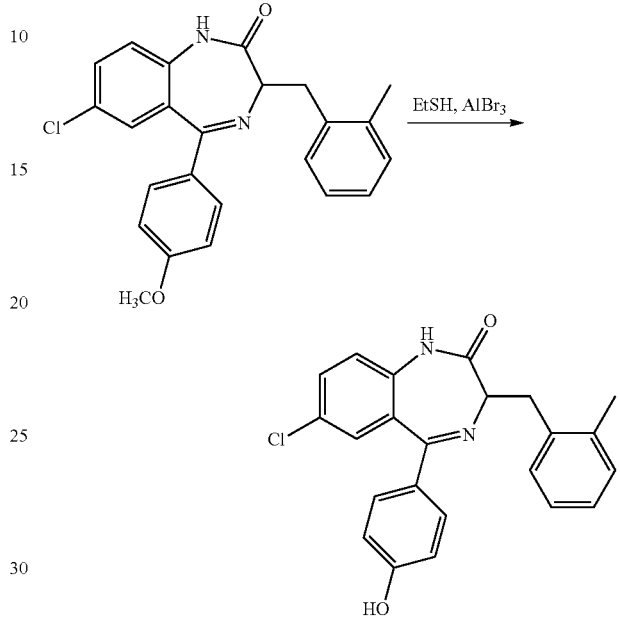

(Z)-7-Chloro-5-(4-hydroxyphenyl)-3-(2-methylbenzyl)-1H-benzo[e][1,4]diazepin-2(3H)-one. To a solution of (Z)-7-chloro-5-(4-methoxyphenyl)-3-(2-methylbenzyl)-1H-benzo[e][1,4]diazepin-2(3H)-one precursor (0.6 g, 1.4 mmol) in $CH_2Br_2$ (20 mL) was added EtSH (7 mL) and then $AlBr_3$ (1.7 g, 6.3 mmol, 4.5 eq). The resulting mixture was stirred overnight and then treated with ice (20 g) and after one hour filtered. The resulting solid was triturated with 50% DCM/heptane and then vacuum dried to give 445 mg (yield of 80%) of (Z)-7-chloro-5-(4-hydroxyphenyl)-3-(2-methylbenzyl)-1H-benzo[e][1,4]diazepin-2(3H)-one as a light yellow solid. $^1$H NMR (300 MHz, DMSO-$d_6$) δ 2.31 (s, 3H), 3.25-3.45 (m, 2H), 3.73 (dd, 1H), 6.80 (d, 2H), 7.02-7.18 (m, 3H), 7.2-7.3 (m, 5H), 7.64 (dd, 1H), 10.0 (br s, 1H), 10.7 (br s, 1H). MS, m/z 391.7 [M+1]

The following compounds were prepared based on the above procedure:

(Z)-7-Chloro-5-(4-hydroxyphenyl)-3-(2-methylbenzyl)-1-methyl-1H-benzo[e][1,4]diazepin-2(3H)-one. $^1$H NMR (300 MHz, DMSO-$d_6$) δ 2.32 (s, 3H), 3.3-3.5 (m, 5H; contains singlet for NMe at 3.36), 3.90 (t, 1H), 6.87 (d, 2H), 7.05-7.15 (m, 3H), 7.20 (m, 1H), 7.29 (fine d, 1H), 7.35 (d, 2H), 7.65 (d, 1H), 7.78 (dd, 1H), 9-11 (br s, 1H). MS, m/z 405.3 [M+1].

(Z)-7-Chloro-5-(4-hydroxyphenyl)-3-(3-methylbenzyl)-1H-benzo[e][1,4]diazepin-2(3H)-one. $^1$H NMR (300 MHz, DMSO-$d_6$) δ 2.28 (s, 3H), 3.2-3.4 (m, 2H; contains water signal), 3.63 (t, 1H), 6.79 (d, 2H), 7.00 (d, 1H), 7.05-7.15 (m, 3H), 7.20 (m, 1H), 7.29 (fine d, 1H), 7.31 (d, 2 H), 7.62 (dd, 1H), 9.95 (s, 1H), 10.61 (s, 1H). MS, m/z 391.7 [M+1].

(Z)-7-Chloro-5-(4-hydroxyphenyl)-3-(3-methylbenzyl)-1-methyl-1H-benzo[e][1,4]diazepin-2(3H)-one. $^1$H NMR (300 MHz, DMSO-$d_6$) δ 2.25 (s, 3H), 3.25-3.45 (m, 5H; contains singlet for NMe at 3.35), 3.83 (t, 1H), 6.87 (d, 2H), 6.99 (d, 1H), 7.05-7.2 (m, 3H), 7.28 (fine d, 1H), 7.38 (d, 2H), 7.63 (d, 1H), 7.77 (dd, 1H), 10.2 (br s, 1H). MS, m/z 405.3 [M+1].

(Z)-7-Chloro-5-(4-hydroxyphenyl)-3-(4-methylbenzyl)-1H-benzo[e][1,4]diazepin-2(3H)-one. $^1$H NMR (300 MHz, DMSO-d$_6$) δ 2.23 (s, 3H), 3.2-3.4 (m, 3H), 3.80 (m, 1H), 6.86 (d, 2H), 7.09 (d, 2H), 7.23 (d, 2H), 7.25-7.35 (m, 4H), 7.71 (dd, 1H), 10.3 (br s, 1H), 10.9 (br s, 1H). MS, m/z 391.8 [M+1].

(Z)-7-Chloro-5-(4-hydroxyphenyl)-3-(4-methylbenzyl)-1-methyl-1H-benzo[e][1,4]diazepin-2(3H)-one. $^1$H NMR (300 MHz, DMSO-d$_6$) δ 2.24 (s, 3H), 3.25-3.4 (m, 5H; contains singlet for NMe at 3.34), 3.82 (t, 1H), 6.87 (d, 2H), 7.07 (d, 2H), 7.19 (d, 2H), 7.28 (fine d, 1H), 7.37 (d, 2H), 7.63 (d, 1H), 7.76 (dd, 1H), 9.5-11 (br s, 1H). MS, m/z 405.3 [M+1].

(Z)-7-Chloro-3-(2-ethylbenzyl)-5-(4-hydroxyphenyl)-1H-benzo[e][1,4]diazepin-2(3H)-one. $^1$H NMR (300 MHz, DMSO-d$_6$) δ 1.14 (t, 3H), 2.72 (q, 2H), 3.30-3.40 (m, 2H), 3.66 (m, 1H), 6.77 (m, 2H), 7.08-7.26 (m, 8H), 7.60 (d, 1H), 9.93 (s, 1H), 10.66 (s, 1H). MS, m/z 405.6 [M+1].

(Z)-7-Chloro-3-(2-ethylbenzyl)-5-(4-hydroxyphenyl)-1-methyl-1H-benzo[e][1,4]diazepin-2(3H)-one. $^1$H NMR (300 MHz, DMSO-d$_6$), δ 1.11 (t, 3H), 2.69 (q, 2H), 3.34 (m, 2H), 3.74 (m, 1H), 6.78 (m, 2H), 7.08-7.32 (m, 7H), 7.58 (d, 1H), 7.67 (dd, 1H), 9.98 (s, 1H). MS, m/z 419.3 [M+1].

(Z)-3-(3-Ethylbenzyl)-7-chloro-5-(4-hydroxyphenyl)-1H-benzo[e][1,4]diazepin-2(3H)-one. $^1$H NMR (300 MHz, DMSO-d$_6$) δ 1.16 (t, 3H), 2.57 (q, 2H), 3.2-3.35 (m, contains signals for benzylic protons and H$_2$O), 3.60 (t, 1H), 6.79 (d, 2H), 7.02 (dt, 1H), 7.07-7.31 (m, 7H), 7.61 (dd, 1H), 9.94 (s, 1H), 10.62 (s, 1H). MS, m/z 405.2 [M+1].

(Z)-3-(3-Ethylbenzyl)-7-chloro-5-(4-hydroxyphenyl)-1-methyl-1H-benzo[e][1,4]diazepin-2(3H)-one. $^1$H NMR (300 MHz, DMSO-d$_6$) δ 1.17 (t, 3H), 2.57 (q, 2H), 3.3-3.4 (m, contains signals for benzylic protons and NMe, 5H), 3.81 (t, 1H), 6.86 (d, 2H), 7.02 (dt, 1H), 7.08-7.20 (m, 3H), 7.27 (fine d, 1H), 7.38 (d, 2H), 7.63 (d, 1H), 7.73 (dd, 1H), 9.5-11 (br s). MS, m/z 419.2 [M+1].

(Z)-3-(4-Ethylbenzyl)-7-chloro-5-(4-hydroxyphenyl)-1-methyl-1H-benzo[e][1,4]diazepin-2(3H)-one. $^1$H NMR (300 MHz, DMSO-d$_6$) δ 1.14 (t, 3H), 2.58 (q, 2H), 3.36-3.41 (m, 5H), 3.95 (m, 1H), 6.90 (m, 2H), 7.10-7.42 (m, 7H), 7.66 (d, 1H), 7.83 (dd, 1H), ~10.0 (br s, 1H). MS, m/z 419.3 [M+1].

(Z)-3-(4-Ethylbenzyl)-7-chloro-5-(4-hydroxyphenyl)-1H-benzo[e][1,4]diazepin-2(3H)-one. $^1$H NMR (300 MHz, DMSO-d$_6$) δ 1.14 (t, 3H), 2.55 (q, 2H), 3.21-3.68 (m, 2H), 3.60 (m, 1H), 6.79 (m, 2H), 7.07-7.29 (m, 8H), 7.60 (dd, 1H), 9.94 (s, 1H), 10.61 (s, 1H). MS, m/z 405.3 [M+1].

(Z)-3-(3-Isopropylbenzyl)-7-chloro-5-(4-hydroxyphenyl)-1-methyl-1H-benzo[e][1,4]diazepin-2(3H)-one. $^1$H NMR (300 MHz, DMSO-d$_6$) δ 1.18 and 1.21 (two d, 6H), 2.84 (heptet, 1H), 3.3-3.4 (m, 5H; contains NMe singlet at 3.34), 3.82 (t, 1H), 6.85 (d, 2H), 7.0-7.3 (m, 5H), 7.38 (d, 2H), 7.64 (d, 1H), 7.77 (dd, 1H), 9-11 (br s, 1H). MS, m/z 433.2 [M+1].

(Z)-3-(4-Isopropylbenzyl)-7-chloro-5-(4-hydroxyphenyl)-1H-benzo[e][1,4]diazepin-2(3H)-one. $^1$H NMR (300 MHz, DMSO-d$_6$) 1.15 (d, 6H), 2.82 (septet, 1H), 3.24-3.38 (m, 2H), 3.63 (m, 1H), 6.79 (m, 2H), 7.10-7.30 (m, 8H), 7.59 (dd, 1H), 9.45 (s, 1H), 10.61 (s, 1H). MS, m/z 419.3 [M+1].

(Z)-3-(4-Isopropylbenzyl)-7-chloro-5-(4-hydroxyphenyl)-1-methyl-1H-benzo[e][1,4]diazepin-2(3H)-one. $^1$H NMR (300 MHz, DMSO-d$_6$) δ 1.15 (d, 6H), 2.84 (septet, 1H), 3.26-3.41 (m, 5H), 3.77 (m, 1H), 6.84 (m, 2H), 7.10-7.40 (m, 7H), 7.63 (d, 1H), 7.73 (dd, 1H), 10.2 (br s, 1H). MS, m/z 433.3 [M+1].

Method B:

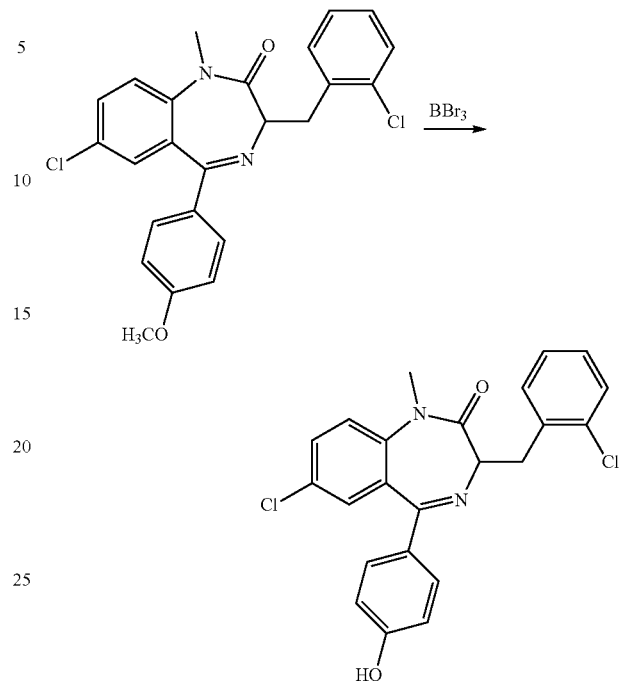

(Z)-7-Chloro-3-(2-chlorobenzyl)-5-(4-hydroxyphenyl)-1-methyl-1H-benzo[e][1,4]diazepin-2(3H)-one. (Z)-7-chloro-3-(2-chlorobenzyl)-5-(4-methoxyphenyl)-1-methyl-1H-benzo[e][1,4]diazepin-2(3H)-one (230 mg, 0.524 mmol) was dissolved in methylene chloride (5 mL) and cooled to −78° C. under nitrogen. Boron tribromide (54 µL 0.576 mmol) was added dropwise. The mixture turned orange. It was kept at −78° C. for 2 h then allowed to warm to RT. Tlc indicated no reaction after 6 hr. An additional equivalent of boron tribromide was added. The mixture was left stirring overnight at RT. Carefully added water (2 mL) then brine (2 mL). The aqueous layer was extracted twice with methylene chloride. The combined organic layers were dried over magnesium sulfate then filtered and the solvent evaporated. The residue was chromatographed on silica gel eluting with 30-50% ethyl acetate in hexanes to give (Z)-7-chloro-3-(2-chlorobenzyl)-5-(4-hydroxyphenyl)-1-methyl-1H-benzo[e][1,4]diazepin-2 (3H)-one as a yellow solid (18 mg). $^1$H NMR (300 MHz, CDCl$_3$) δ 3.4 (s, 3H), 3.6-3.8 (m, 2H), 3.8-3.9 (m, 1H), 6.8 (d, 2H), 7.1-7.6 (m, 9H); ESI m/z measured 425.0828 [M+H$^+$], calculated 425.0824.

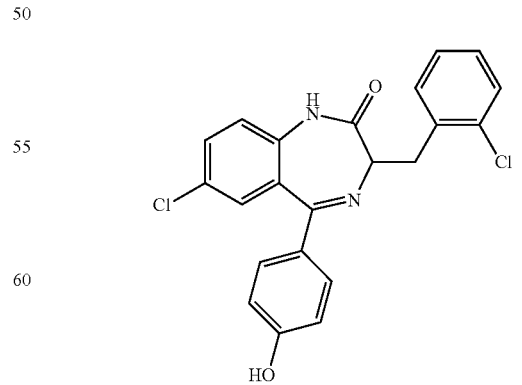

(Z)-7-Chloro-3-(2-chlorobenzyl)-5-(4-hydroxyphenyl)-1H-benzo[e][1,4]diazepin-2(3H)-one. (Z)-7-Chloro-3-(2- chlorobenzyl)-5-(4-methoxyphenyl)-1H-benzo[e][1,4]diazepin-2(3H)-one (74 mg, 0.174 mmol) was dissolved in dichloroethane (1 mL) under nitrogen and BBr₃ (1M in dichloromethane, 0.348 mL, 0.348 mmol) was added dropwise at room temperature (there was an immediate color change from colorless to orange). The reaction mixture was stirred at room temperature for approximately 5 hours. Two more equivalents of BBr₃ in dichloromethane were added (0.348 mL, 0.348 mmol) and the mixture was left stirring for another approximately 18 hours. The reaction was carefully quenched with methanol (exothermic) then diluted with dichloromethane and washed twice with water then once with brine (the last wash gelled so some methanol was added to separate the layers). The organic layer was dried (MgSO₄). Chromatography eluting with 20-40% ethyl acetate in hexanes gave some starting material plus (Z)-7-chloro-3-(2-chlorobenzyl)-5-(4-hydroxyphenyl)-1H-benzo[e][1,4]diazepin-2(3H)-one as a yellow solid (40 mg, 56%). $^1$H NMR (300 MHz, CDCl₃) δ 3.59-3.89 (m, 3H), 6.30 (br s, 1H), 6.71 (d, J=8 Hz, 2H), 7.09-7.32 (m, 4H), 7.44 (dd, J=9, 2 Hz, 1H), 7.58 (d, J=7 Hz, 1H), 9.13 (s, 1H); ESI m/z 411.0.

Example 11

Representative General Procedures for Synthesis of C5-Hydroxyphenyl Substituted Benzodiazepines via Palladium Coupling of a Bromo-4-(alkoxyaralkyloxy)aryl Group and a 5-Chlorobenzo[e][1,4]diazepin-2(3H)-one Part I:

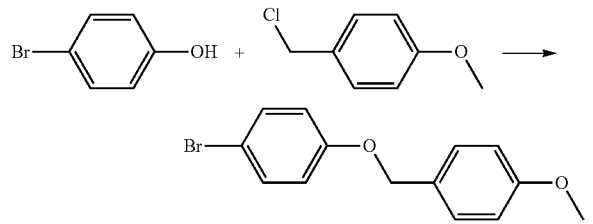

1-Bromo-4-(4-methoxybenzyloxy)benzene. 4-Bromophenol (25.00 g, 145 mmol), para-methoxybenzyl chloride (24.89 g, 159 mmol), potassium iodide (2.17 g, 14.45 mmol), and potassium carbonate (39.9 g, 289 mmol) in acetone (600 mL) was heated to reflux for 18 h. The crude reaction mixture was then cooled to room temperature and filtered through a sintered glass funnel. The filtrate was concentrated in vacuo, and the white solid was recrystallized from ethanol yielding the product as a white solid (33.44 g, 79%). $^1$H NMR (300 MHz, CDCl₃) δ 3.80 (s, 3H), 4.95 (s, 2H), 6.85 (d, 2H), 6.92 (d, 2H), 7.32-7.40 (m, 4H).

Part II:

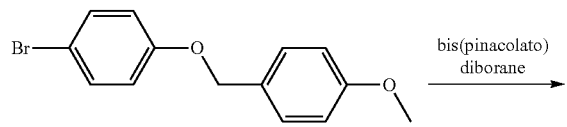

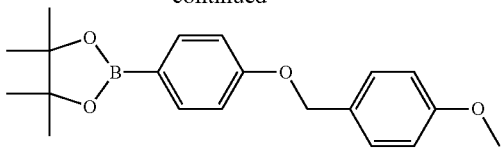

2-(4-(4-Methoxybenzyloxy)phenyl)-4,4,5,5-tetramethyl-1,3,2-dioxaborolane. 1-Bromo-4-(4-methoxybenzyloxy)benzene (10.00 g, 34.1 mmol) was dissolved in dioxane (250 mL), and bis(pinacolato)diborane (11.26 g, 44.3 mmol), and potassium acetate (10.04 g, 102 mmol) were added. The mixture was subjected to vacuum until bubbling occurred, and then nitrogen gas was introduced. The degassing procedure was repeated twice, and then tetrakis(triphenylphosphine) palladium (0) (512 mg, 0.44 mmol) was added, and the reaction was heated to 90° C. for 3 hours. The crude reaction mixture was then cooled to room temperature, and then diluted with ethyl acetate, and the organic solution was washed with water, then brine, then dried over sodium sulfate, and concentrated. The crude residue was filtered through a silica plug eluting with 6:4 ethyl acetate:hexanes. The filtrate was then concentrated, and washed with isopropyl alcohol (30 mL), and the solid product was collected by filtration yielding the product as a dull yellow solid (9.85 g, 85%). $^1$H NMR (300 MHz, CDCl₃) δ 1.34 (s, 12H), 3.81 (s, 3H), 5.02 (s, 2H), 6.91 (d, 2H), 6.96 (d, 2H), 7.36 (d, 2H), 7.74 (d, 2H).

Part III:

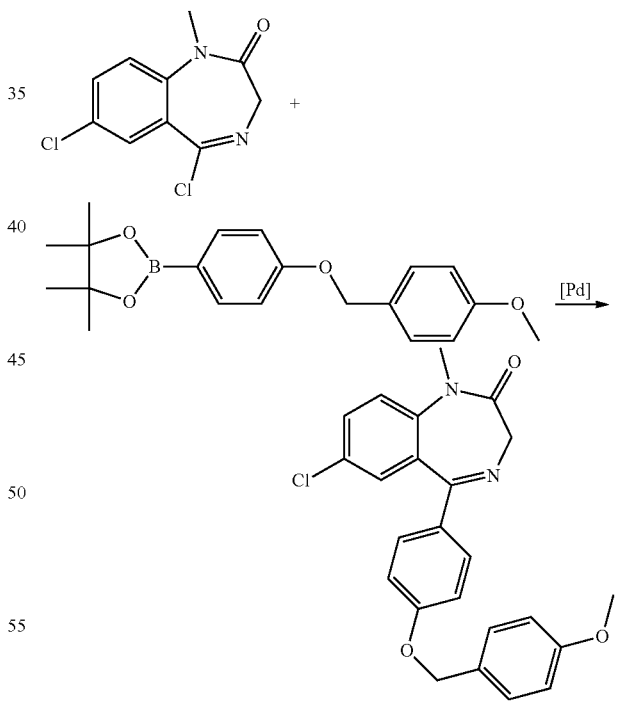

(Z)-7-Chloro-5-(4-(4-methoxybenzyloxy)phenyl)-1-methyl-1H-benzo[e][1,4]diazepin-2(3H)-one. (E)-5,7-Dichloro-1-methyl-1H-benzo[e][1,4]diazepin-2(3H)-one (5.00 g, 20.57 mmol), cesium hydroxide (6.91 g, 41.1 mmol), and 2-(4-(4-methoxybenzyloxy)phenyl)-4,4,5,5-tetramethyl-1,3,2-dioxaborolane (9.10 g, 26.7 mmol) were dissolved in dioxane/water (100 mL/30 mL), and the mixture was subjected to vacuum followed by nitrogen gas. The degassing was repeated twice, and then tetrakis(triphenylphosphine)palladium (0) (475 mg, 0.41 mmol) was added. The reaction was then heated to 90° C. for 18 hours, and then cooled to room temperature. The crude mixture was diluted with ethyl acetate, and the organic solution was washed with water, then brine, and then dried over sodium sulfate, and concentrated. The crude product was vacuum pulled through a silica plug eluting with 6:4 ethyl acetate:hexanes. The filtrate was concentrated and then washed with methyl-tert-butyl ether. The product was collected as a light yellow solid by filtration (5.13 g, 59%). ¹H NMR (300 MHz, CDCl₃) δ 3.36 (s, 3H), 3.73 (d, 1H), 3.81 (s, 3H), 4.77 (d, 1H), 5.03 (s, 2H), 6.91 (d, 2H), 6.98 (d, 2H), 7.27 (d, 1H), 7.32 (d, 1H), 7.36 (d, 2H), 7.49 (dd, 1H), 7.55 (d, 2H).

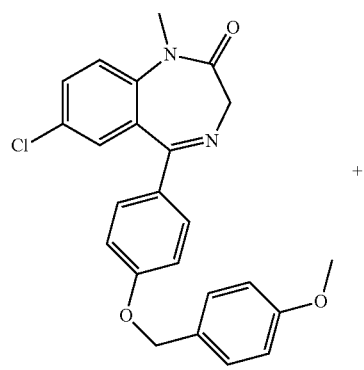

+

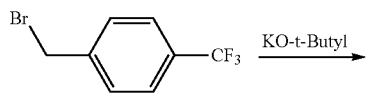

KO-t-Butyl

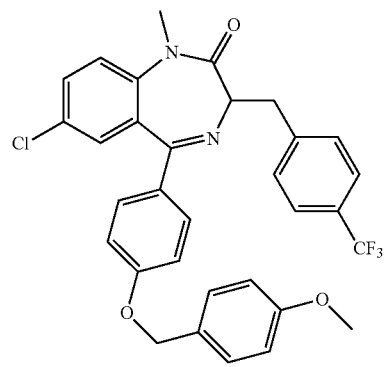

(Z)-7-Chloro-5-(4-(4-methoxybenzyloxy)phenyl)-1-methyl-3-(4-(trifluoromethyl)benzyl)-1H-benzo[e][1,4]diazepin-2(3H)-one. (Z)-7-Chloro-5-(4-(4-methoxybenzyloxy)phenyl)-1-methyl-1H-benzo[e][1,4]diazepin-2(3H)-one (75 mg, 0.18 mmol) was dissolved in tetrahydrofuran (4 mL), and the solution was cooled to −78° C. under a nitrogen atmosphere. A 1 M solution of potassium tert-butoxide in tetrahydrofuran (267 µL, 0.267 mmol) was added dropwise, and the solution was stirred for 10 minutes. 4-(trifluoromethyl)benzyl bromide (64 mg, 0.267 mmol, solution in 1 mL tetrahydrofuran) was then added dropwise, and the cooling bath was then removed. The reaction was stirred at room temperature for 2 hours, and it was then quenched with water, and the mixture was portioned between water and ethyl acetate. The aqueous portion was extracted into ethyl acetate again, and the combined organic extracts were dried over sodium sulfate, and then concentrated, and purified by chromatography (gradient; 9:1 hexanes:ethyl acetate to 6:4 hexanes:ethyl acetate, then isocratic) yielding the product as a clear residue (50 mg, 49%).

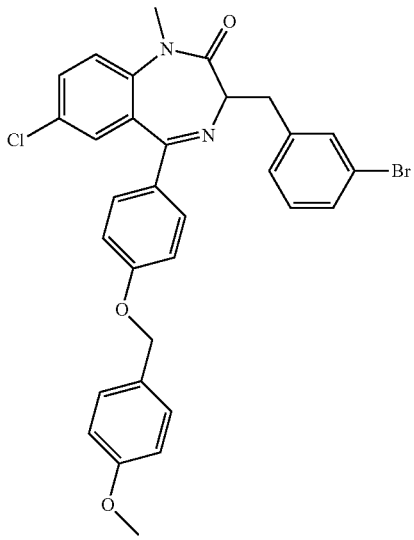

(Z)-3-(3-Bromobenzyl)-7-chloro-5-(4-(4-methoxybenzyloxy)phenyl)-1-methyl-1H-benzo[e][1,4]diazepin-2(3H)-one. Following the procedure described above, (Z)-3-(3-bromobenzyl)-7-chloro-5-(4-(4-methoxybenzyloxy)phenyl)-1-methyl-1H-benzo[e][1,4]diazepin-2(3H)-one was obtained from 3-bromobenzylbromide as a colorless solid (47 mg, 45%).

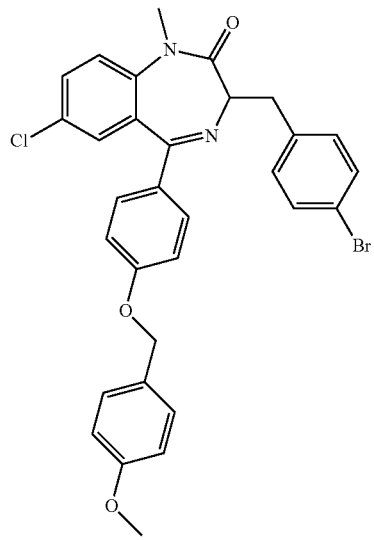

(Z)-3-(4-Bromobenzyl)-7-chloro-5-(4-(4-methoxybenzyloxy)phenyl)-1-methyl-1H-benzo[e][1,4]diazepin-2(3H)-one. Following the procedure described above, (Z)-3-(4-bromobenzyl)-7-chloro-5-(4-(4-methoxybenzyloxy)phenyl)-1-methyl-1H-benzo[e][1,4]diazepin-2(3H)-one was obtained from 4-bromobenzylbromide as a colorless solid (22 mg, 21%).

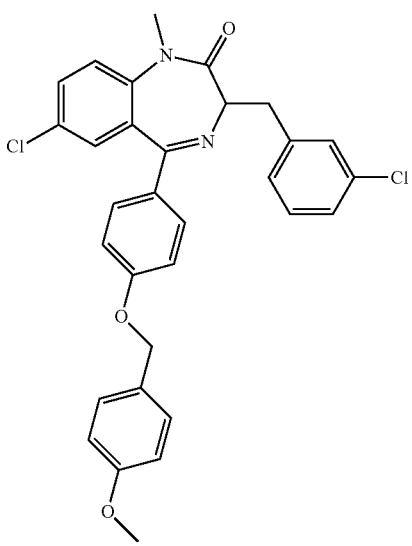

(Z)-7-Chloro-3-(3-chlorobenzyl)-5-(4-(4-methoxybenzyloxy)phenyl)-1-methyl-1H-benzo[e][1,4]diazepin-2(3H)-one. Following the procedure described above, (Z)-7-chloro-3-(3-chlorobenzyl)-5-(4-(4-methoxybenzyloxy)phenyl)-1-methyl-1H-benzo[e][1,4]diazepin-2(3H)-one was obtained from 3-chlorobenzylbromide as a colorless solid (24 mg, 25%).

Part IV:

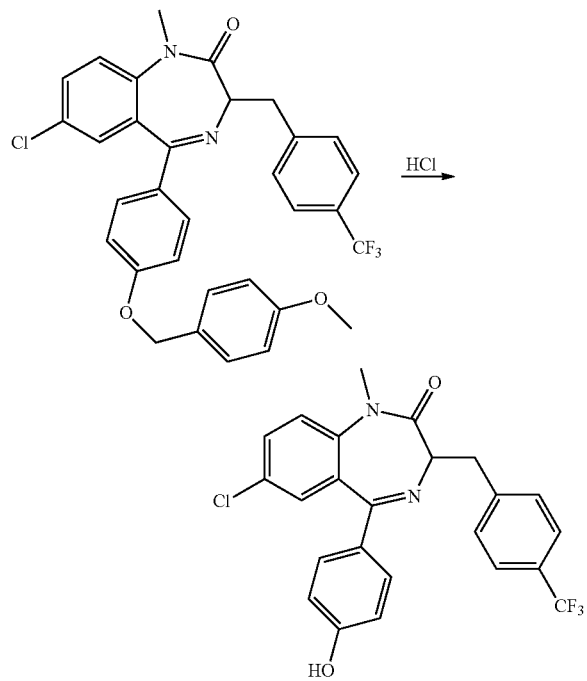

(Z)-7-Chloro-5-(4-hydroxyphenyl)-1-methyl-3-(4-(trifluoromethyl)benzyl)-1H-benzo[e][1,4]diazepin-2(3H)-one. (Z)-7-chloro-5-(4-(4-methoxybenzyloxy)phenyl)-1-methyl-3-(4-(trifluoromethyl)benzyl)-1H-benzo[e][1,4]diazepin-2(3H)-one (50 mg, 0.086 mmol) was dissolved in 4 N HCl in dioxane (3 mL) and stirred for 3 h. The solution was then concentrated, and sonicated in 5 mL of diethyl ether. The product was collected by filtration as a bright yellow solid (24.2 mg, 61%). $^1$H NMR (300 MHz, DMSO-d$_6$) δ 3.30 (s, 3H), 3.32-3.43 (m, 3H), 6.80 (d, 2H), 7.22 (d, 1H), 7.30-7.40 (m, 2H), 7.50-7.78 (m, 6H); ESI m/z measured 459.1078 [M+H$^+$], calculated 459.1087.

The following compounds were prepared based on the above procedures:

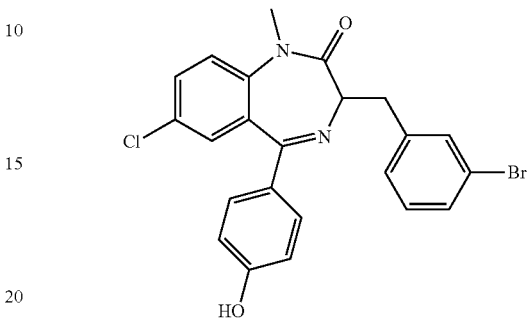

(Z)-3-(3-Bromobenzyl)-7-chloro-5-(4-hydroxyphenyl)-1-methyl-1H-benzo[e][1,4]diazepin-2(3H)-one. The product was obtained as a yellow solid (28.2 mg, 75%). $^1$H NMR (300 MHz, DMSO-d$_6$) δ 3.30-3.35 (m, 5H), 3.82 (t, 1H), 4.30-4.80 (bs, 5H), 6.82 (d, 2H), 7.18-7.26 (m, 2H), 7.30-7.39 (m, 4H), 7.55-7.63 (m, 2H), 7.72 (dd, 1H); ESI m/z measured 469.0314 [M+H$^+$], calculated 469.0318.

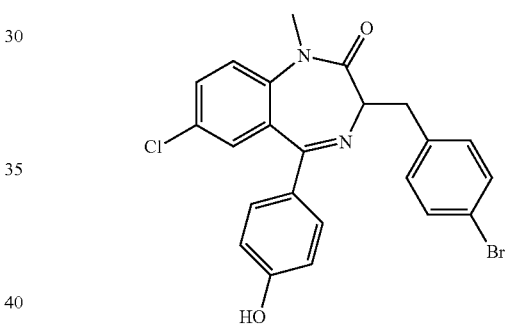

(Z)-3-(4-Bromobenzyl)-7-chloro-5-(4-hydroxyphenyl)-1-methyl-1H-benzo[e][1,4]diazepin-2(3H)-one. The product was obtained as a yellow solid (7 mg, 40%). $^1$H NMR (300 MHz, DMSO-d$_6$) δ 3.27-3.38 (m, 5H), 6.80 (d, 2H), 7.21-7.36 (m, 5H), 7.42 (d, 2H), 7.58 (d, 1H), 7.70 (dd, 1H); ESI m/z measured 469.0318 [M+H$^+$], calculated 469.0318.

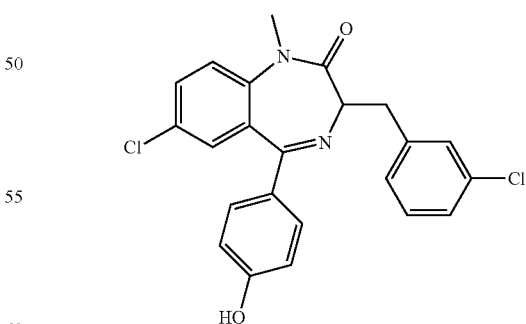

(Z)-7-Chloro-3-(3-chlorobenzyl)-5-(4-hydroxyphenyl)-1-methyl-1H-benzo[e][1,4]diazepin-2(3H)-one. The product was obtained as a yellow solid (4.5 mg, 24%). $^1$H NMR (300 MHz, DMSO-d$_6$) δ 3.30-3.40 (m, 5H), 4.70 (q, 2H), 4.85 (s, 1H), 6.82 (d, 2H), 7.10-7.22 (m, 2H), 7.29-7.50 (m, 5H), 7.60 (d, 1H), 7.70-7.80 (m, 2H). ESI m/z measured 425.1062 [M+H$^+$], calculated 425.0824.

Example 12

Representative General Procedures for Synthesis of Benzimidazolones

Part I:

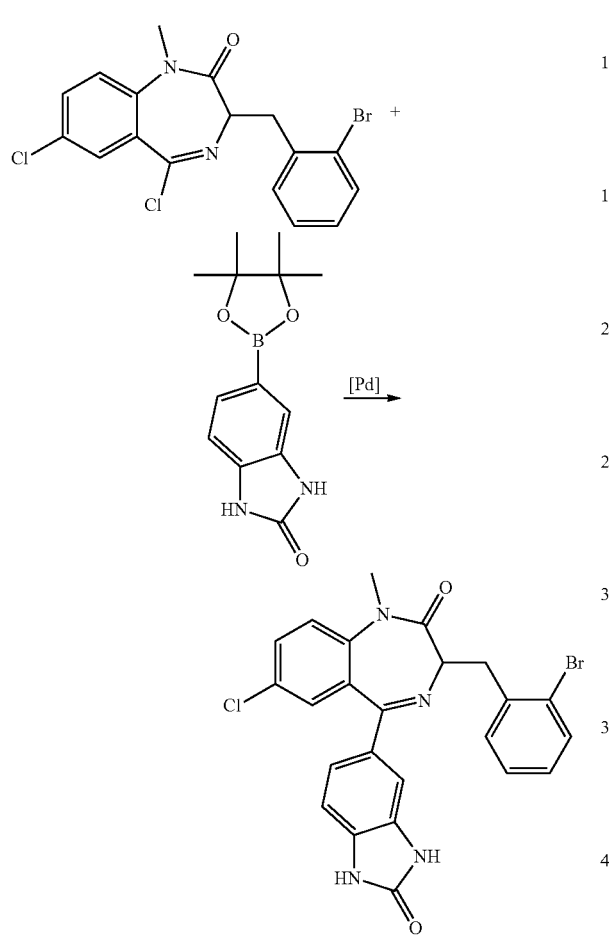

(Z)-3-(2-Bromobenzyl)-7-chloro-1-methyl-5-(2-oxo-2,3-dihydro-1H-benzo[d]imidazol-5-yl)-1H-benzo[e][1,4]diazepin-2(3H)-one. (E)-3-(2-Bromobenzyl)-5,7-dichloro-1-methyl-1H-benzo[e][1,4]diazepin-2(3H)-one (150 mg, 0.364 mmol), 5-(4,4,5,5-tetramethyl-1,3,2-dioxaborolan-2-yl)-1H-benzo[d]imidazol-2(3H)-one (95 mg, 0.364 mmol) and lithium chloride (46 mg, 1.09 mmol) were added to 1,4-dioxane (3 mL). Nitrogen was bubbled into the solution as reagents were added. Tetrakis(triphenylphosphine) palladium(0) (42 mg, 0.036 mmol) was added followed by cesium hydroxide monohydrate (183 mg, 1.09 mmol) and water (1 mL). After bubbling nitrogen through for 5 minutes, the reaction mixture was heated to 100° C. under a nitrogen atmosphere. After heating for 1 hour, the mixture was cooled to ambient temperature, diluted with ethyl acetate (25 mL), washed with water (2×20 mL), then brine (20 mL), dried with sodium sulfate, decanted then concentrated in the presence of silica. The dried silica-bound residue was dry loaded onto a silica gel column and eluted with a gradient of 60-100% ethyl acetate in hexanes then a gradient of 0-25% methanol in ethyl acetate to yield (Z)-3-(2-bromobenzyl)-7-chloro-1-methyl-5-(2-oxo-2,3-dihydro-1H-benzo[d]imidazol-5-yl)-1H-benzo[e][1,4]diazepin-2(3H)-one (35 mg, 19%). $^1$H NMR (300 MHz, DMSO-$d_6$) δ 3.32 (s, 3H) 3.49 (m, 2H), 3.82 (t, 1H), 6.89-7.17 (m, 3H), 7.28-7.71 (m, 7H), 10.70 (s, 1H), 10.87 (s, 1H); ESI m/z measured 509.0359 [M+H]$^+$, calculated 509.0380.

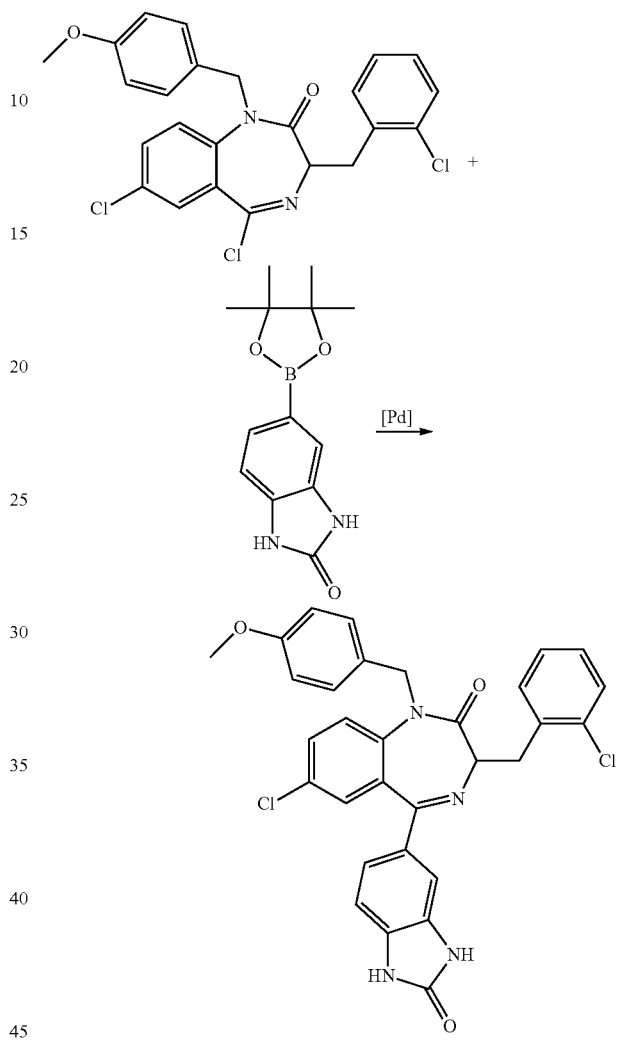

(Z)-7-Chloro-3-(2-chlorobenzyl)-1-(4-methoxybenzyl)-5-(2-oxo-2,3-dihydro-1H-benzo[d]imidazol-5-yl)-1H-benzo[e][1,4]diazepin-2(3H)-one. (E)-5,7-Dichloro-3-(2-chlorobenzyl)-1-(4-methoxybenzyl)-1H-benzo[e][1,4]diazepin-2(3H)-one (0.68 g, 1.44 mmol), 2-oxo-2,3-dihydro-1H-benzoimidazole-5-boronic acid pinacol ester (0.37 g, 1.44 mmol) and lithium chloride (0.183 g, 4.31 mmol) were added to 1,4-dioxane (12 mL). Nitrogen was bubbled into the solution as reagents were added. Tetrakis(triphenylphosphine) palladium(0) (166 mg, 0.144 mmol) was added followed by cesium hydroxide monohydrate (723 mg, 4.31 mmol) and water (1 mL). After bubbling nitrogen through the mixture for 5 minutes it was heated to 100° C. under a nitrogen atmosphere. Following heating for 2 hours, the mixture was cooled to ambient temperature, diluted with ethyl acetate (50 mL), washed with water (2×40 mL), then brine (40 mL), dried with sodium sulfate, decanted, then concentrated in the presence of silica. The resulting silica gel-bound crude product was loaded onto a silica gel column and eluted with a gradient of 0-100% ethyl acetate in hexanes to yield (Z)-7- chloro-3-(2-chlorobenzyl)-1-(4-methoxybenzyl)-5-(2-oxo-2,3-dihydro-1H-benzo[d]imidazol-5-yl)-1H-benzo[e][1,4]diazepin-2(3H)-one as a 2:1 mixture of product:2-oxo-2,3-dihydro-1H-benzoimidazole-5-boronic acid pinacol ester (200 mg, 24%). ESI m/z 571.1, 573.1.

Part II:

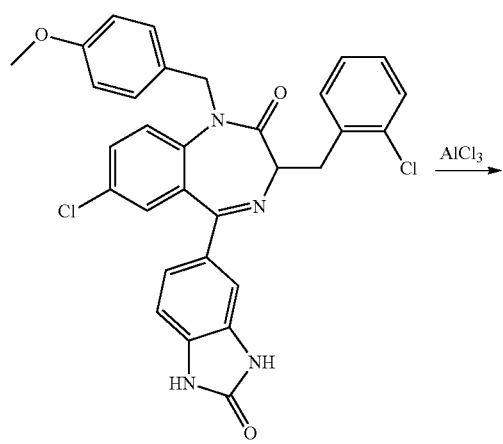

(Z)-7-Chloro-3-(2-chlorobenzyl)-5-(2-oxo-2,3-dihydro-1H-benzo[d]imidazol-5-yl)-1H-benzo[e][1,4]diazepin-2(3H)-one. (Z)-7-Chloro-3-(2-chlorobenzyl)-1-(4-methoxybenzyl)-5-(2-oxo-2,3-dihydro-1H-benzo[d]imidazol-5-yl)-1H-benzo[e][1,4]diazepin-2(3H)-one (200 mg, 0.35 mmol) was dissolved in anhydrous anisole (4 mL) under a nitrogen atmosphere, aluminum chloride (280 mg, 2.1 mmol) was added and the mixture was heated to 85° C. for 1 hour. The solution was cooled to ambient temperature, poured onto ice, rinsing the flask with ethyl acetate and water. The mixture was slurried for 10 minutes. The layers were separated and the aqueous layer was extracted with ethyl acetate. The combined organic layers were washed with brine, dried with sodium sulfate, decanted and concentrated in the presence of silica gel. The residue was chromatographed on silica gel eluting with 70-100% ethyl acetate in hexanes switching to a gradient of 0-10% methanol in ethyl acetate to give (Z)-7-chloro-3-(2-chlorobenzyl)-5-(2-oxo-2,3-dihydro-1H-benzo[d]imidazol-5-yl)-1H-benzo[e][1,4]diazepin-2(3H)-one (70 mg, 44%). $^1$H NMR (300 MHz, DMSO-$d_6$) δ 3.46 (d, 2H) 3.76 (t, 1H), 6.90 (m, 2H), 7.01 (s, 1H) 7.21-7.64 (m, 7H), 10.70 (s, 1H), 10.74 (s, 1H), 10.85 (s, 1H); ESI m/z measured 451.0736 [M+H$^+$], calculated 451.0729.

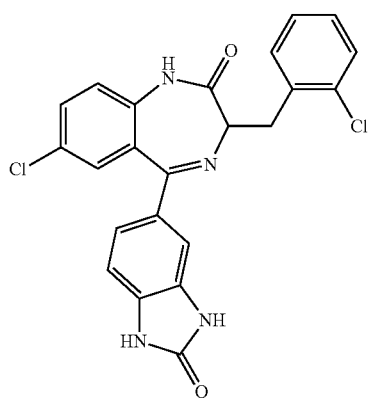

Example 13

The compounds listed in Table 4 were tested for activity against $F_1F_0$-ATPase and cytotoxicity in Ramos cells. Inhibition of ATP synthesis and hydrolysis by the $F_1F_0$-ATPase was measured as described in K. M. Johnson et al., *Chemistry & Biology* 2005, 12, 485-496. Cytotoxicity in Ramos cells was measured as described in K. M. Johnson et al., *Chemistry & Biology* 2005, 12, 485-496, or using the alamarBlue™ Assay with fluorescence detection (U.S. Pat. No. 5,501,959) as supplied and described by Invitrogen (Carlsbad, Calif.).

TABLE 4

| No. | Compound Name | Compound Structure | ATPase IC$_{50}$ | Ramos Cell EC$_{50}$ |
|---|---|---|---|---|
| 1 | (Z)-1-(4-(3-(2-bromobenzyl)-7-chloro-2-oxo-2,3-dihydro-1H-benzo[e][1,4]diazepin-5-yl)phenyl)-3-isopropylurea | | ++ | +++ |

TABLE 4-continued

| No. | Compound Name | Compound Stucture | ATPase IC$_{50}$ | Ramos Cell EC$_{50}$ |
|---|---|---|---|---|
| 2 | (Z)-1-(4-(7-chloro-2-oxo-3-(2-(trifluoromethyl)benzyl)-2,3-dihydro-1H-benzo[e][1,4]diazepin-5-yl)phenyl)-3-isopropylurea | | ++ | +++ |
| 3 | (Z)-1-(4-(7-chloro-3-(2-fluorobenzyl)-2-oxo-2,3-dihydro-1H-benzo[e][1,4]diazepin-5-yl)phenyl)-3-isopropylurea | | ++ | ++ |
| 4 | (Z)-1-(4-(7-chloro-3-(2-chlorobenzyl)-2-oxo-2,3-dihydro-1H-benzo[e][1,4]diazepin-5-yl)phenyl)-3-isopropylurea | | ++ | +++ |
| 5 | (Z)-1-(4-(7-chloro-3-(2-chlorobenzyl)-2-oxo-2,3-dihydro-1H-benzo[e][1,4]diazepin-5-yl)phenyl)-3-methylurea | | ++ | ++ |

TABLE 4-continued

| No. | Compound Name | Compound Structure | ATPase IC$_{50}$ | Ramos Cell EC$_{50}$ |
|---|---|---|---|---|
| 6 | (Z)-1-(4-(7-chloro-3-(2-chlorobenzyl)-2-oxo-2,3-dihydro-1H-benzo[e][1,4]diazepin-5-yl)phenyl)-3-(2-(dimethylamino)ethyl)urea | | + | +++ |
| 7 | (Z)-1-(4-(7-chloro-3-(2-chlorobenzyl)-2-oxo-2,3-dihydro-1H-benzo[e][1,4]diazepin-5-yl)phenyl)-3-(2,2,2-trifluoroethyl)urea | | +++ | +++ |
| 8 | (Z)-1-(4-(7-chloro-3-(2-chlorobenzyl)-2-oxo-2,3-dihydro-1H-benzo[e][1,4]diazepin-5-yl)phenyl)-3-cyclopropylurea | | ++ | +++ |
| 9 | (Z)-1-(4-(7-chloro-3-(2-chlorobenzyl)-2-oxo-2,3-dihydro-1H-benzo[e][1,4]diazepin-5-yl)phenyl)-3-(2-methoxyethyl)urea | | ++ | +++ |

TABLE 4-continued

| No. | Compound Name | Compound Structure | ATPase IC$_{50}$ | Ramos Cell EC$_{50}$ |
|-----|---------------|--------------------|-----------------|---------------------|
| 10 | (Z)-1-(4-(7-chloro-3-(2-chlorobenzyl)-2-oxo-2,3-dihydro-1H-benzo[e][1,4]diazepin-5-yl)phenyl)-3-(2-ethoxyethyl)urea | | ++ | +++ |
| 11 | (Z)-1-(4-(3-(2-bromobenzyl)-7-chloro-2-oxo-2,3-dihydro-1H-benzo[e][1,4]diazepin-5-yl)phenyl)-3-methylurea | | ++ | +++ |
| 12 | (Z)-1-(4-(3-(2-bromobenzyl)-7-chloro-2-oxo-2,3-dihydro-1H-benzo[e][1,4]diazepin-5-yl)phenyl)-3-(2-(dimethylamino)ethyl)urea | | ++ | +++ |
| 13 | (Z)-1-(4-(3-(2-bromobenzyl)-7-chloro-2-oxo-2,3-dihydro-1H-benzo[e][1,4]diazepin-5-yl)phenyl)-3-(2,2,2-trifluoroethyl)urea | | +++ | +++ |

TABLE 4-continued

| No. | Compound Name | Compound Structure | ATPase IC$_{50}$ | Ramos Cell EC$_{50}$ |
|---|---|---|---|---|
| 14 | (Z)-1-(4-(3-(2-bromobenzyl)-7-chloro-2-oxo-2,3-dihydro-1H-benzo[e][1,4]diazepin-5-yl)phenyl)-3-cyclopropylurea | | ++ | +++ |
| 15 | (Z)-1-(4-(3-(2-bromobenzyl)-7-chloro-2-oxo-2,3-dihydro-1H-benzo[e][1,4]diazepin-5-yl)phenyl)-3-(2-methoxyethyl)urea | | ++ | +++ |
| 16 | (Z)-1-(4-(3-(2-bromobenzyl)-7-chloro-2-oxo-2,3-dihydro-1H-benzo[e][1,4]diazepin-5-yl)phenyl)-3-(2-ethoxyethyl)urea | | ++ | +++ |
| 17 | (Z)-7-chloro-5-(4-hydroxyphenyl)-3-(2-methylbenzyl)-1H-benzo[e][1,4]diazepin-2(3H)-one | | ++ | ++ |

TABLE 4-continued

| No. | Compound Name | Compound Stucture | ATPase IC$_{50}$ | Ramos Cell EC$_{50}$ |
|---|---|---|---|---|
| 18 | (Z)-7-chloro-5-(4-hydroxyphenyl)-1-methyl-3-(2-methylbenzyl)-1H-benzo[e][1,4]diazepin-2(3H)-one | | + | + |
| 19 | (Z)-7-chloro-5-(4-hydroxyphenyl)-3-(3-methylbenzyl)-1H-benzo[e][1,4]diazepin-2(3H)-one | | ++ | ++ |
| 20 | (Z)-7-chloro-5-(4-hydroxyphenyl)-1-methyl-3-(3-methylbenzyl)-1H-benzo[e][1,4]diazepin-2(3H)-one | | + | + |
| 21 | (Z)-7-chloro-5-(4-hydroxyphenyl)-3-(4-methylbenzyl)-1H-benzo[e][1,4]diazepin-2(3H)-one | | ++ | ++ |
| 22 | (Z)-7-chloro-5-(4-hydroxyphenyl)-1-methyl-3-(4-methylbenzyl)-1H-benzo[e][1,4]diazepin-2(3H)-one | | + | + |

TABLE 4-continued

| No. | Compound Name | Compound Structure | ATPase IC$_{50}$ | Ramos Cell EC$_{50}$ |
|-----|---------------|--------------------|------------------|----------------------|
| 23 | (Z)-7-chloro-3-(2-ethylbenzyl)-5-(4-hydroxyphenyl)-1H-benzo[e][1,4]diazepin-2(3H)-one | | ++ | ++ |
| 24 | (Z)-7-chloro-3-(2-ethylbenzyl)-5-(4-hydroxyphenyl)-1-methyl-1H-benzo[e][1,4]diazepin-2(3H)-one | | ++ | + |
| 25 | (Z)-7-chloro-3-(3-ethylbenzyl)-5-(4-hydroxyphenyl)-1H-benzo[e][1,4]diazepin-2(3H)-one | | ++ | ++ |
| 26 | (Z)-7-chloro-3-(3-ethylbenzyl)-5-(4-hydroxyphenyl)-1-methyl-1H-benzo[e][1,4]diazepin-2(3H)-one | | ++ | ++ |
| 27 | (Z)-7-chloro-3-(4-ethylbenzyl)-5-(4-hydroxyphenyl)-1-methyl-1H-benzo[e][1,4]diazepin-2(3H)-one | | ++ | ++ |

TABLE 4-continued

| No. | Compound Name | Compound Stucture | ATPase IC$_{50}$ | Ramos Cell EC$_{50}$ |
|---|---|---|---|---|
| 28 | (Z)-7-chloro-3-(4-ethylbenzyl)-5-(4-hydroxyphenyl)-1H-benzo[e][1,4]diazepin-2(3H)-one | | ++ | ++ |
| 29 | (Z)-7-chloro-5-(4-hydroxyphenyl)-3-(3-isopropylbenzyl)-1-methyl-1H-benzo[e][1,4]diazepin-2(3H)-one | | ++ | ++ |
| 30 | (Z)-7-chloro-5-(4-hydroxyphenyl)-3-(4-isopropylbenzyl)-1H-benzo[e][1,4]diazepin-2(3H)-one | | ++ | ++ |
| 31 | (Z)-7-chloro-5-(4-hydroxyphenyl)-3-(4-isopropylbenzyl)-1-methyl-1H-benzo[e][1,4]diazepin-2(3H)-one | | ++ | ++ |
| 32 | (Z)-7-chloro-5-(4-hydroxyphenyl)-1-methyl-3-(2-(trifluoromethyl)benzyl)-1H-benzo[e][1,4]diazepin-2(3H)-one | | ++ | ++ |

TABLE 4-continued

| No. | Compound Name | Compound Structure | ATPase IC$_{50}$ | Ramos Cell EC$_{50}$ |
|---|---|---|---|---|
| 33 | (Z)-3-(2-bromobenzyl)-7-chloro-5-(4-hydroxyphenyl)-1H-benzo[e][1,4]diazepin-2(3H)-one | | ++ | +++ |
| 34 | (Z)-7-chloro-3-(2-chlorobenzyl)-5-(4-hydroxyphenyl)-1-methyl-1H-benzo[e][1,4]diazepin-2(3H)-one | | +++ | ++ |
| 35 | (Z)-3-(2-bromobenzyl)-7-chloro-1-methyl-5-(2-oxo-2,3-dihydro-1H-benzo[d]imidazol-5-yl)-1H-benzo[e][1,4]diazepin-2(3H)-one | | NA | ++ |
| 36 | (Z)-7-chloro-5-(4-hydroxyphenyl)-1-methyl-3-(4-(trifluoromethyl)benzyl)-1H-benzo[e][1,4]diazepin-2(3H)-one | | +++ | ++ |
| 37 | (Z)-3-(3-bromobenzyl)-7-chloro-5-(4-hydroxyphenyl)-1-methyl-1H-benzo[e][1,4]diazepin-2(3H)-one | | +++ | ++ |

TABLE 4-continued

| No. | Compound Name | Compound Structure | ATPase IC$_{50}$ | Ramos Cell EC$_{50}$ |
|---|---|---|---|---|
| 38 | (Z)-3-(4-bromobenzyl)-7-chloro-5-(4-hydroxyphenyl)-1-methyl-1H-benzo[e][1,4]diazepin-2(3H)-one | | +++ | ++ |
| 39 | (Z)-7-chloro-3-(3-chlorobenzyl)-5-(4-hydroxyphenyl)-1-methyl-1H-benzo[e][1,4]diazepin-2(3H)-one | | + | + |
| 40 | (Z)-7-chloro-3-(2-chlorobenzyl)-5-(4-hydroxyphenyl)-1H-benzo[e][1,4]diazepin-2(3H)-one | | +++ | ++ |
| 41 | (Z)-7-chloro-3-(2-chlorobenzyl)-5-(2-oxo-2,3-dihydro-1H-benzo[d]imidazol-5-yl)-1H-benzo[e][1,4]diazepin-2(3H)-one | | +++ | +++ |

+++ corresponds to <5 μM, ++ corresponds to 5-10 μM, + corresponds to >10 μM, NA means that no data was available

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

I claim:

1. A method of treating a disorder selected from the group consisting of graft versus host disease, psoriasis, and leukemia, comprising administering an effective amount of a benzodiazepine compound of Formula I or II to a subject in need thereof to treat said disorder, wherein Formula I is represented by:

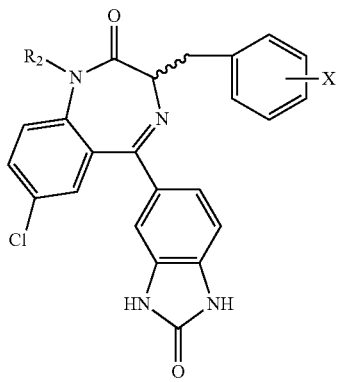

(I)

or a pharmaceutically acceptable salt thereof; and
including both R and S enantiomeric forms and racemic mixtures thereof; wherein:

X is selected from the group consisting of halogen, alkyl, and an alkyl group substituted by one or more substituents selected from the group consisting of halogen, hydroxyl, alkylcarbonyloxy, alkylaminocarbonyl, alkoxyl, cyano, amino, and acylamino; and $R_2$ is selected from the group consisting of hydrogen and a linear or branched alkyl; and wherein Formula II is represented by:

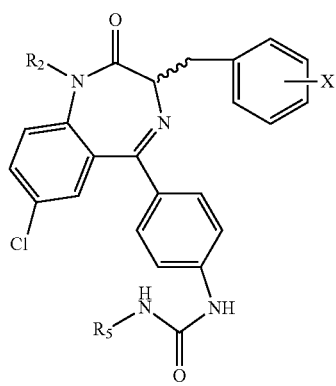

(II)

or a pharmaceutically acceptable salt thereof; and
including both R and S enantiomeric forms and racemic mixtures thereof; wherein:

X is selected from the group consisting of halogen, alkyl, and an alkyl group substituted by one or more substituents selected from the group consisting of halogen, hydroxyl, alkylcarbonyloxy, alkylaminocarbonyl, alkoxyl, cyano, amino, and acylamino;

$R_2$ is selected from the group consisting of hydrogen and a linear or branched alkyl; and $R_5$ is alkyl optionally substituted by one or more substituents selected from the group consisting of halogen, hydroxyl, alkoxyl, cyano, and amino.

2. The method of claim 1, wherein said disorder is graft versus host disease.

3. The method of claim 1, wherein said disorder is leukemia.

4. The method of claim 1, wherein said disorder is psoriasis.

5. The method of claim 4, further comprising administering an additional agent for treating said psoriasis.

6. The method of claim 1, wherein the subject is a human.

7. The method of claim 2, wherein the benzodiazepine compound is a compound of Formula I.

8. The method of claim 7, wherein X is halogen, and $R_2$ is hydrogen.

9. The method of claim 4, wherein the benzodiazepine compound is a compound of Formula I.

10. The method of claim 9, wherein X is halogen, and $R_2$ is hydrogen.

11. The method of claim 2, wherein the benzodiazepine compound is

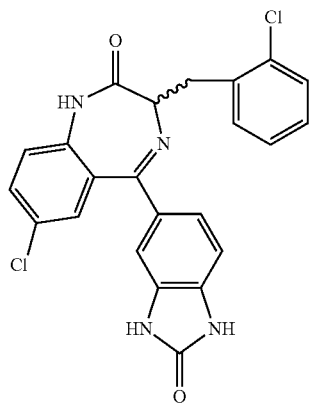

or a pharmaceutically acceptable salt thereof.

12. The method of claim 3, wherein the benzodiazepine compound is

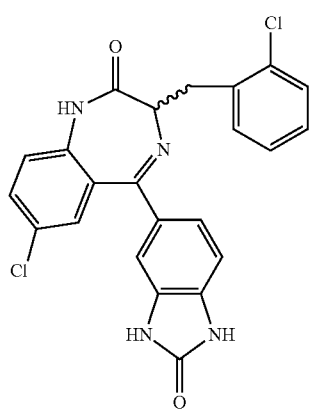

or a pharmaceutically acceptable salt thereof.

13. The method of claim 4, wherein the benzodiazepine compound is

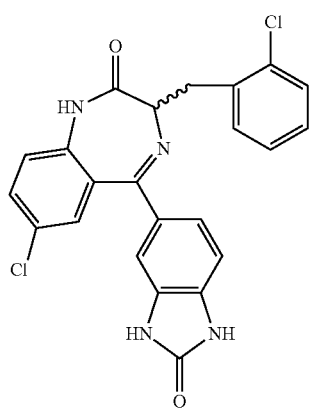

or a pharmaceutically acceptable salt thereof.

14. The method of claim 2, wherein the benzodiazepine compound is
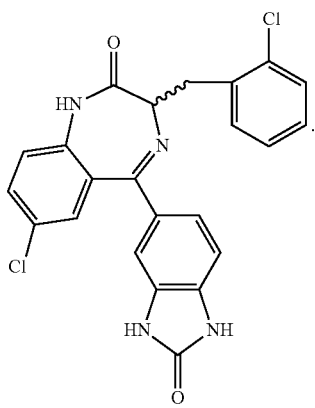
15. The method of claim 4, wherein the benzodiazepine compound is
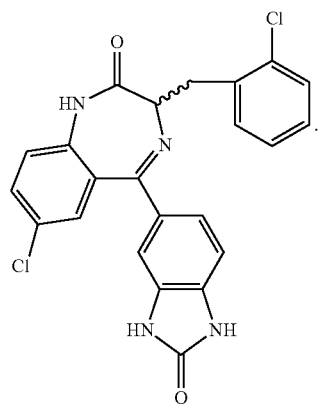
* * * * *